United States Patent
Aimone et al.

(10) Patent No.: US 10,365,716 B2
(45) Date of Patent: Jul. 30, 2019

(54) WEARABLE COMPUTING APPARATUS AND METHOD

(71) Applicant: INTERAXON INC., Toronto (CA)

(72) Inventors: Christopher Allen Aimone, Toronto (CA); Ariel Stephanie Garten, Toronto (CA); Trevor Coleman, Toronto (CA); Locillo (Lou) Giuseppe Pino, Cambridge (CA); Kapil Jay Mishra Vidyarthi, Toronto (CA); Paul Harrison Baranowski, Toronto (CA); Michael Apollo Chabior, Oakville (CA); Tracy Chong, Toronto (CA); Raul Rajiv Rupsingh, Brampton (CA); Madeline Ashby, Toronto (CA); Paul V. Tadich, Toronto (CA)

(73) Assignee: INTERAXON INC., Toronto (CA)

( * ) Notice: Subject to any disclaimer, the term of this patent is extended or adjusted under 35 U.S.C. 154(b) by 0 days.

(21) Appl. No.: 14/216,925

(22) Filed: Mar. 17, 2014

(65) Prior Publication Data
US 2014/0347265 A1    Nov. 27, 2014

Related U.S. Application Data

(60) Provisional application No. 61/792,585, filed on Mar. 15, 2013.

(51) Int. Cl.
*G06F 3/01* (2006.01)
*A61B 5/0496* (2006.01)
(Continued)

(52) U.S. Cl.
CPC ............ *G06F 3/015* (2013.01); *A61B 5/0496* (2013.01); *A61B 5/04842* (2013.01);
(Continued)

(58) Field of Classification Search
CPC . G06F 3/01; G06F 3/011; G06F 3/013; G06F 3/015; G06F 3/048; G06F 3/0482; G06F 3/04842
(Continued)

(56) References Cited

U.S. PATENT DOCUMENTS 5,052,401 A * 10/1991 Sherwin ............... A61B 3/02
                                                             329/358
5,360,971 A * 11/1994 Kaufman .............. A61B 3/113
                                                             250/221
(Continued)

FOREIGN PATENT DOCUMENTS

WO    2012071545    5/2012

OTHER PUBLICATIONS

WIPO, International Search Report dated Jul. 3. 2014, issued in corresponding International Patent Application No. PCT/CA2014/000256.
(Continued)

*Primary Examiner* — Jason M Mandeville
(74) *Attorney, Agent, or Firm* — Norton Rose Fulbright Canada LLP; Tamara O'Connell

(57) ABSTRACT

A method is provided, performed by a wearable computing device comprising at least one bio-signal measuring sensor, the at least one bio-signal measuring sensor including at least one brainwave sensor, comprising: acquiring at least one bio-signal measurement from a user using the at least one bio-signal measuring sensor, the at least one bio-signal measurement comprising at least one brainwave state measurement; processing the at least one bio-signal measurement, including at least the at least one brainwave state measurement, in accordance with a profile associated with the user; determining a correspondence between the processed at least one bio-signal measurement and at least one
(Continued)

predefined device control action; and in accordance with the correspondence determination, controlling operation of at least one component of the wearable computing device, such as modifying content displayed on a display of the wearable computing device. Various types of bio-signals, including brainwaves, may be measured and used to control the device in various ways.

15 Claims, 40 Drawing Sheets

(51) Int. Cl.

| | | |
|---|---|---|
| *G06F 3/0487* | (2013.01) | |
| *H04W 4/04* | (2009.01) | |
| *A61B 5/0484* | (2006.01) | |
| *A61B 5/16* | (2006.01) | |
| *A61B 5/00* | (2006.01) | |
| *A61M 21/00* | (2006.01) | |
| *G02B 27/01* | (2006.01) | |
| *G09G 3/00* | (2006.01) | |
| *G06F 3/048* | (2013.01) | |
| *G02C 11/00* | (2006.01) | |
| *G06F 16/90* | (2019.01) | |
| *A61B 5/024* | (2006.01) | |
| *A61B 5/026* | (2006.01) | |
| *A61B 5/0482* | (2006.01) | |
| *A61B 5/0488* | (2006.01) | |
| *H04L 29/08* | (2006.01) | |
| *H04M 1/05* | (2006.01) | |

(52) U.S. Cl.
CPC .......... *A61B 5/04845* (2013.01); *A61B 5/165* (2013.01); *A61B 5/4064* (2013.01); *A61B 5/6803* (2013.01); *A61M 21/00* (2013.01); *G02B 27/017* (2013.01); *G02C 11/10* (2013.01); *G06F 3/013* (2013.01); *G06F 3/048* (2013.01); *G06F 3/0487* (2013.01); *G06F 16/90* (2019.01); *G09G 3/003* (2013.01); *H04W 4/04* (2013.01); *A61B 5/0024* (2013.01); *A61B 5/0261* (2013.01); *A61B 5/02416* (2013.01); *A61B 5/02438* (2013.01); *A61B 5/0482* (2013.01); *A61B 5/0488* (2013.01); *A61B 5/7267* (2013.01); *A61B 5/744* (2013.01); *A61B 2560/0493* (2013.01); *A61M 2021/0022* (2013.01); *A61M 2021/0027* (2013.01); *A61M 2021/0044* (2013.01); *A61M 2021/0066* (2013.01); *A61M 2230/10* (2013.01); *A61M 2230/14* (2013.01); *G02B 2027/0187* (2013.01); *H04L 67/12* (2013.01); *H04M 1/05* (2013.01); *H04M 2250/12* (2013.01)

(58) Field of Classification Search
USPC .......................................................... 345/156
See application file for complete search history.

(56) References Cited

U.S. PATENT DOCUMENTS

| | | | | |
|---|---|---|---|---|
| 5,649,061 | A * | 7/1997 | Smyth | A61B 3/113 |
| | | | | 250/221 |
| 5,726,916 | A * | 3/1998 | Smyth | A61B 5/6814 |
| | | | | 351/210 |
| 6,167,298 | A | 12/2000 | Levin | |
| 6,349,231 | B1 | 2/2002 | Musha | |
| 7,206,022 | B2 * | 4/2007 | Miller | G02B 27/0093 |
| | | | | 348/231.3 |
| 7,546,158 | B2 | 6/2009 | Allison et al. | |
| 8,473,045 | B2 * | 6/2013 | Terada | A61B 5/04842 |
| | | | | 600/544 |
| 9,092,055 | B2 * | 7/2015 | Chen | G06F 3/015 |
| 9,489,574 | B2 * | 11/2016 | Lee | G06K 9/00268 |
| 2005/0088617 | A1 | 4/2005 | Hsieh | G06F 3/015 |
| | | | | 351/205 |
| 2006/0061544 | A1 * | 3/2006 | Min | G02B 27/0093 |
| | | | | 345/156 |
| 2008/0065468 | A1 * | 3/2008 | Berg | G06Q 30/02 |
| | | | | 705/7.32 |
| 2008/0177197 | A1 | 7/2008 | Lee et al. | |
| 2009/0289895 | A1 * | 11/2009 | Nakada | G06F 3/013 |
| | | | | 345/157 |
| 2010/0191140 | A1 * | 7/2010 | Terada | A61B 5/04842 |
| | | | | 600/544 |
| 2011/0105909 | A1 * | 5/2011 | Sun | G06F 3/013 |
| | | | | 600/473 |
| 2012/0236030 | A1 | 9/2012 | Border et al. | |
| 2012/0242678 | A1 * | 9/2012 | Border | G02B 27/0093 |
| | | | | 345/589 |
| 2012/0245713 | A1 * | 9/2012 | Chen | G06F 3/015 |
| | | | | 700/83 |
| 2012/0257035 | A1 * | 10/2012 | Larsen | G06F 3/017 |
| | | | | 348/78 |
| 2013/0091515 | A1 * | 4/2013 | Sakata | H04N 17/04 |
| | | | | 725/10 |
| 2013/0131535 | A1 * | 5/2013 | Sun | G06F 3/015 |
| | | | | 600/544 |
| 2014/0223462 | A1 * | 8/2014 | Aimone | H04N 21/42201 |
| | | | | 725/10 |
| 2014/0267005 | A1 * | 9/2014 | Urbach | G06F 3/016 |
| | | | | 345/156 |

OTHER PUBLICATIONS

European Patent Office, Supplementary European Search Report for EP Application No. 14762241.9 dated Sep. 26, 2016.

* cited by examiner

WEARABLE COMPUTING APPARATUS AND METHOD

CROSS-REFERENCE TO RELATED APPLICATION(S)

This application claims all benefit, including priority, of U.S. Provisional Patent Application Ser. No. 61/792,585, filed 15 Mar. 2013 and entitled WEARABLE COMPUTING APPARATUS AND METHOD, the entire contents of which is incorporated herein by reference, in its entirety.

FIELD OF THE INVENTION

The present invention relates generally to wearable computing. The present invention further relates to apparatuses and methods applying sensors to wearable computing devices.

BACKGROUND OF THE INVENTION

A user may interact with a computing device for example using a keyboard, mouse, track pad, touch screen, or motion-capture devices. As the ways in which humans interact with computing devices change, computers may become usable for new purposes, or more efficient in performing existing tasks. A user command to a computing device that may require several commands on a keyboard may be instead associated with a single hand gesture captured and processed by a motion-capture input device. As the human body has many parts which may be controlled through voluntary movement, there are opportunities for capturing and interpreting other movements for interacting with a computing device.

SUMMARY OF THE INVENTION

A method is provided, performed by a wearable computing device comprising a display, and at least one bio-signal measuring sensor, comprising: acquiring at least one bio-signal measurement from a user using the at least one bio-signal measuring sensor; processing the at least one bio-signal measurement in accordance with a profile associated with the user; determining a correspondence between the processed at least one bio-signal measurement and a predefined display control action; and in accordance with the correspondence determination, modifying an image displayed on the display.

In accordance with an aspect of the present invention, there is provided a method, performed by a wearable computing device comprising at least one bio-signal measuring sensor, the at least one bio-signal measuring sensor including at least one brainwave sensor, comprising: acquiring at least one bio-signal measurement from a user using the at least one bio-signal measuring sensor, the at least one bio-signal measurement comprising at least one brainwave state measurement; processing the at least one bio-signal measurement, including at least the at least one brainwave state measurement, in accordance with a profile associated with the user; determining a correspondence between the processed at least one bio-signal measurement and at least one predefined device control action; and in accordance with the correspondence determination, controlling operation of at least one component of the wearable computing device.

In accordance with an aspect of the present invention, there is provided a non-transitory computer program product tangibly embodying code that, when executed by a processor, causes the processor to carry out the method of the present invention.

In accordance with an aspect of the present invention, there is provided a wearable computing device comprising: at least one bio-signal measuring sensor, the at least one bio-signal measuring sensor including at least one brainwave sensor; at least one processor coupled to the at least one bio-signal measuring sensor; and a non-transitory computer-readable medium or media comprising computer-executable instructions configured to cause the at least one data processor to: acquire at least one bio-signal measurement from a user using the at least one bio-signal measuring sensor, the at least one bio-signal measurement comprising at least one brainwave state measurement; process the at least one bio-signal measurement, including at least the at least one brainwave state measurement, in accordance with a profile associated with the user; determine a correspondence between the processed at least one bio-signal measurement and at least one predefined device control action; and in accordance with the correspondence determination, control operation of at least one component of the wearable computing device.

In this respect, before explaining at least one embodiment of the invention in detail, it is to be understood that the invention is not limited in its application to the details of construction and to the arrangements of the components set forth in the following description or the examples provided therein, or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

Figure 1A:
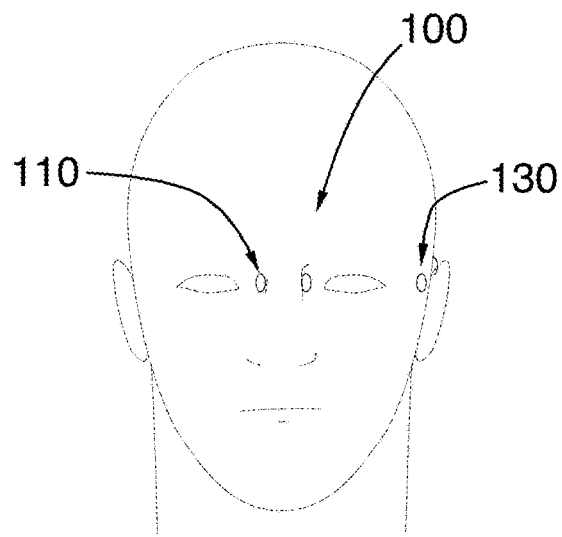
FIGS. 1A to 1C illustrate front elevation, side elevation, and perspective views, respectively, of a possible implementation of the invention.

This invention describes a method, performed by a wearable computing device comprising a display, and at least one bio-signal measuring sensor, comprising: acquiring at least one bio-signal measurement from a user using the at least one bio-signal measuring sensor; processing the at least one bio-signal measurement in accordance with a profile associated with the user; determining a correspondence between the processed at least one bio-signal measurement and a predefined display control action; and in accordance with the correspondence determination, modifying an image displayed on the display. Optionally, the display may be part of the wearable computing device itself, or it may be provided on a separate computing device that is connected to or otherwise in communication with the wearable computing device. The separate computing device may also be a wearable device worn by the user.

In a particular aspect of the invention, a wearable computing device is provided including a camera, a display, and bio-signal measuring means to sample a user's environment as well as the user's bio-signals, determining the user's state and context through sensors and user input.

In a particular aspect of the invention, the bio-signal measuring system may include at least one of (1) an electrical bio-signal sensor in electrical contact with the user's skin; (2) a capacitive bio-signal sensor in capacitive contact with the user's skin; (3) a blood flow sensor measuring properties of the user's blood flow; and (4) a wireless communication sensor placed sub-dermally underneath the user's skin.

In another aspect of the invention, the wearable computing device may include at least one user-facing camera to track eye movement. In a particular aspect of the invention, the wearable computing device may be in a form resembling eyeglasses wearable on the user's face. Optionally, at least one camera may be oriented to generally align with the user's field of view.

In another aspect of the invention, the wearable computing device may be in a form of at least one sensor adapted to being placed at or adhered to the user's head or face. Each sensor may optionally communicate with one another either through wires or wirelessly. Each sensor may optionally communicate with a controller device either through wires or wirelessly. The controller device may be mounted to the wearable computing device in order to reside at or near the user's head or face. Alternatively, the controller device may be located elsewhere on the user's body, such as in a bag or pocket of the user's clothing. The controller device may also be disposed somewhere outside the user's body. For example, the sensors may monitor the user, storing data in local storage mounted to the wearable computing device, and once moving into proximity with the controller device, the sensors, or a transmitter of the wearable computing device may transmit stored data to the controller device for processing. In this implementation, the wearable computing device would be predominantly usable by the user when located nearby the controller device.

The wearable computing device may include a camera, a display and bio-signal measuring means. At least one of the bio-signal measuring means may employ at least one sensor in order to measure brain activity. Brain activity may be measured through electroencephalography ("EEG") techniques electrically, or through functional near-infrared spectroscopy ("fNIR") techniques measuring relative changes in hemoglobin concentration through the use of near infrared light attenuation. A sensor employing pulse oximetry techniques may also be employed in the wearable computing device. Optionally, the wearable computing device may include at least one sensor measuring eye activity using electrooculography ("EOG") techniques. Other sensors tracking other types of eye movement may also be employed.

In various implementations, the wearable computing device may include a variety of other sensors and input means. For example, the wearable computing device may comprise at least one audio transducer such as a single microphone, a microphone array, a speaker, and headphones. The wearable computing device may comprise at least one inertial sensor for measuring movement of the wearable computing device. The wearable computing device may comprise at least one touch sensor for receiving touch input from the user.

The wearable computing device may sample from both the user's environment and bio-signals simultaneously or generally contemporaneously to produce sampled data. The sampled data may be analyzed by the wearable computing device in real-time or at a future predetermined time when not being worn by the user.

The wearable computing device may comprise user input detection methods that are adaptive and improve with use over time. Where the user attempts to command the wearable computing device, and the wearable computing device responds in an unexpected way, the user may attempt to correct the previous input by indicating that the wearable computing device response was incorrect, and retrying the initial command again. Over time, the wearable computing device may refine its understanding of particular user inputs that are corrected. Some user inputs may be easier to successfully measure with a high degree of accuracy than others. It may be preferable to assign a high-accuracy input to command the wearable computing device that the previous input was incorrect. For example, tapping the wearable computing device in a particular spot may indicate that the previous input response was incorrect. Explicit training such as with voice recognition may also be used to configure and command the wearable computing device.

In one implementation, the wearable computing device may be in a glasses-like form factor. Glasses, with or without eyeglass elements, may be well-suited on which to mount sensors as glasses may be easily mounted to the user's face, and are easily removed. Glasses may also be relatively stable in position with respect to the user's head when resting on parts of the user's nose and ears. In order to further reduce movement of the glasses, arm-portions of the glasses may grip sides or rear portions of the user's head. Resilient arm-portions may be particularly useful for achieving a suitable gripping strength, thereby minimizing movement of the glasses and any sensors mounted thereupon.

Optionally, the wearable computing device may itself only provide bio-signal sensors and a processor for processing measurements from the sensors. The wearable computing device may communicate these measurements or data derived from processing the measurements to one or more secondary devices, such as a Google Glass™-style device. In any of the implementations, embodiments, or applications discussed herein, it should be understood that some actions may be carried out by a plurality of interconnected devices, or just one of the wearable computing devices of the present invention. For example, the wearable computing device may not include a display. In such an example, the wearable computing device may communicate visual information to the user through the use of a second device, such as a Google Glass-style device, which does include a display.

Sensors usable with the wearable computing device may come in various shapes and be made of various materials. For example, the sensors may be made of a conductive material, including a conductive composite like rubber or conductive metal. The sensors may also be made of metal plated or coated materials such as stainless steel, silver-silver chloride, and other materials.

The sensors may include one more bio-signal sensors, such as electroencephalogram (EEG) sensors, galvanometer sensors, electrocardiograph sensors, heart rate sensors, eye-tracking sensors, blood pressure sensors, pedometers, gyroscopes, and any other type of sensor. The sensors may be connected to the wearable computing device, such as a wearable headset or headband computer worn by the user. The sensors may be connected to the wearable computing device by wires or wirelessly.

In accordance with an aspect of the present invention, there may be provided a method, performed by a wearable computing device comprising at least one bio-signal measuring sensor, the at least one bio-signal measuring sensor including at least one brainwave sensor. The method may include acquiring at least one bio-signal measurement from a user using the at least one bio-signal measuring sensor. The at least one bio-signal measurement may include at least one brainwave state measurement. The wearable computing device may process the at least one bio-signal measurement, including at least the at least one brainwave state measurement, in accordance with a profile associated with the user. The wearable computing device may determine a correspondence between the processed at least one bio-signal measurement and at least one predefined device control action. In accordance with the correspondence determination, the wearable computing device may control operation of at least one component of the wearable computing device.

The wearable computing device may include a display component, and the controlling operation of the at least one component may comprise modifying or initiating the modification of an image displayed on the display.

The wearable computing device comprises at least one eye-tracking sensor, and the wearable computing device may perform the steps of displaying at least one item on the display, acquiring at least one eye-tracking measurement from the user using the at least one eye-tracking sensor, determining a correspondence between the eye-tracking measurement and the displayed location of one of the at least one displayed item, and in accordance with the eye-tracking correspondence determination and the bio-signal correspondence determination, modifying or initiating the modification of at least one displayed item by the at least one predefined device control action. The at least one item may comprise a search result item, and the at least one predefined device control action may comprise selecting the one of the at least one displayed item. The at least one predefined control action may comprise for example narrowing the search results by at least one property associated with the one at least one displayed item. The processed at least one bio-signal measurement may identify a user-interest in the one at least one displayed item by comparing the bio-signal measurement to a predefined bio-signal measurement stored in the user profile, the bio-signal correspondence determination based at least partly on the identified user-interest.

The bio-signal correspondence determination may determine a correspondence between the at least one bio-signal measurement and a predefined bio-signal measurement stored in the user profile, the predefined bio-signal measurement associated with at least one emotional response type. The at least one predefined display control action may comprise tagging the one at least one displayed item with the corresponding at least one emotional response type. The at least one predefined display control action may comprise displaying a predefined message associated with at least one emotional response type.

The wearable computing device may be configured to display at least one item on the display, each of the at least one displayed item displayed at a distinct display frequency with respect to the other at least one displayed item, wherein the correspondence determining comprises determining a correspondence between the at least one brainwave state measurement and the display frequency of the at least one displayed item.

The wearable computing device may be configured to display at least one item on the display, the at least one item associated with an item sequence; wherein the processed at least one bio-signal measurement identifies a user-interest in the one at least one displayed item by comparing the bio-signal measurement to a predefined bio-signal measurement stored in the user profile associated with a predetermined user-interest level, and wherein the correspondence determining comprises determining a correspondence between the processed at least one bio-signal measurement and the at least one predefined device control action based at least partly on the identified user interest. The at least one predefined device control action may comprise modifying a rate of advancement in displaying a subsequent at least one display item in the item sequence in accordance with a determined level of the identified user-interest. The wearable computing device may be configured to display an indication of the rate of advancement on the display. The at least one component being controlled may comprise a camera, and the controlling operation of the at least one component may comprise initiating a change in an operation state of the camera. The at least one component being controlled may comprise a microphone, and the controlling operation of the at least one component may comprise initiating a change in an operation state of the microphone. The wearable computing device may use analysis and interpretation of brainwaves and brain physiology to control device functions and components, such as camera, microphone, camera including video camera, and onscreen display, etc.

The interpretation of brainwaves and brain physiology can include but not limited to: EEG—electroencephalography; fNIRS—Functional near-infrared spectroscopy; fMRI—Functional Magnetic Resonance Imaging; and Ultrasound. The wearable computing device may be used for therapy for interventions by applying one or more of the following: EEG—electroencephalography in the form of neurofeedback; fNIRS—Functional near-infrared spectroscopy as Hemoencephalography based neurofeedback; fMRI—Functional Magnetic Resonance Imaging based neurofeedback; TCMS—Transcranial magnetic stimulation; Electroconvulsive therapy; tDCS—Transcranial direct-current stimulation; and Ultrasound based neurofeedback.

The device may provide the user with private audio, visual and or haptic feedback about their biological and or physiological state which is only observable by the wearer.

The computing device may comprise a human-wearable eyeglass frame, each of the display and bio-signal measuring sensor being connected to the eyeglass frame.

The at least one bio-signal measuring sensor may comprise an electrical bio-signal sensor in electrical contact with the user.

The at least one bio-signal measuring sensor may comprise a capacitive bio-signal sensor in capacitive contact with the user.

The at least one bio-signal measuring sensor may comprise a blood flow sensor measuring properties of the user's blood flow.

The at least one bio-signal measuring sensor may comprise a wireless communication sensor placed subdermally with respect to the user's skin.

The at least one bio-signal measurement acquiring may comprise at least one of electroencephalography ("EEG"), functional near-infrared spectroscopy ("fNIR"), and electrooculography ("EOG").

The at least one brainwave state measurement may comprise p300 wave data.

The wearable computing device may comprise at least one camera, and the wearable computing device may be configured to, in accordance with a determined correspondence between the processed at least one bio-signal measurement and a predetermined bio-signal state, control the at least one camera to take visual input of a current field of view of the wearer user of the wearable computing device. The wearable computing device may be configured to receive input from the wearer user indicating at least one object viewable in the field of view; and associate the at least one bio-signal measurement with the indicated at least one object; wherein the controlling operation comprises modifying or initiating the modification of an image displayed on the display based at least partly on the indicated at least one object. The wearable computing device may comprise at least one eye-tracking sensor, the wearable computing device may be configured to acquire at least one eye-tracking measurement from the user using the at least one eye-tracking sensor; and determine the indicated at least one object at least partly by determining at least one eye focal area in the field of view based at least partly on the at least one eye-tracking measurement. The wearable computing device may be configured to identify at least one object in the field of view at least partly by applying at least one image recognition process to the visual input from the camera; and the controlling operation may comprise modifying or initiating the modification of an image displayed on the display is based at least partly on the identified at least one object. The modifying or initiating the modification of an image displayed on the display may comprise displaying information associated with the identified object retrieved from a database. The database may be stored on at least one computer server, the at least one wearable computing device in communication with the at least one computer server over a communications network.

The wearable computing device may comprise: at least one location-determining component; and at least one orientation-determining component. The wearable computing device may be configured to determine a field of view of a wearer user of the wearable computing device based at least partly on: a determined location of the wearable computing device; and a determined orientation of the wearable computing device, the determined location and the determined orientation based at least partly on data received from the at least one location-determining component and the at least one orientation-determining component; and the wearable computing device may determine at least one object that is viewable based at least partly on the determined field of view and a database of objects associated with at least one location determined to be viewable in the determined field of view. The modifying or initiating the modification of an image displayed on the display may comprise displaying information associated with the identified object retrieved from a database.

The wearable computing device may be configured to identify at least one object in the field of view at least partly by applying at least one image recognition process to the visual input from the camera. The controlling operation may comprise modifying or initiating the modification of an image displayed on the display is based at least partly on the identified at least one object.

In combination with GPS (latitude and longitude), digital compass, and accelerometer (angle above plane of the ground) the wearable computing device may include an algorithm to tell what is in a person's field of view. Eye trackers can also be used to fine tune the direction of where a person is looking after an estimate using digital compass, GPS, and accelerometer. Knowing what a person is looking at in combination with analysis and interpretation of their brainwaves can enable useful applications such as: advertisers knowing brain state response (e.g. like/dislike/emotional etc.) response to their fixed billboard ads, knowing who the person is looking and their emotional reaction (e.g. like/dislike/emotional etc.) to that person (assuming the location of the other person is known), how often objects in a city are looked at and people's brain state response.

The wearable computing device may be configured to associate the visual input with the at least one brainwave state measurement and update the profile with the associated visual input. The identified at least one object may comprise at least one food item. The associating the visual input may comprise updating the profile with an identification of the at least one food item associated with the at least one brainwave state measurement. The wearable computing device may be configured to determine a quantity of the at least one food item consumed. The associating the visual input may comprise updating the profile with the determined quantity associated with the at least one brainwave state measurement.

The controlling operation of at least one component of the wearable computing device may comprise sharing the processed at least one brainwave state measurement with at least one computing device over a communications network. The at least one computing device may comprise at least one second wearable computing device. The wearable computing device may comprise at least one camera; wherein controlling operation of at least one component of the wearable computing device comprises sharing visual input received from the at least one camera with the at least one computing device; the method comprising receiving directions from the at least one computing device in response to the shared visual input and at least one brainwave state measurement. Accordingly, people can know the brain state reactions of others to them if permissions allow the sharing of this information (e.g. use social media to find a dating partner by sharing bio-signal measurement information towards a respective person). The wearable computing device may comprise a camera, and the wearable computing device may be configured to identify at least one person viewable in visual input from the camera by applying at least one image recognition process to the visual input; and modify or initiate the modification of the image displayed on the display with information associated with the identified at least one person.

The wearable computing device may be configured to receive the information associated with the identified at least one person from at least one computer server, the information comprising at least the identified person's name.

The wearable computing device may be configured to determine at least one emotional state of the at least one person viewable in the visual input from the camera based at least partly on at least one voice stress analysis, facial expression, body language, and changes in skin colour as analyzed by the wearable computing device.

The wearable computing device may be configured to receive at least one brainwave state measurement of the at least one person from at least one second wearable computing device over a communications network; and modify or initiate the modification of the image displayed on the display based at least partly on the received at least one brainwave state measurement of the at least one person.

The processed at least one brainwave state measurement may be indicative of error-related negativity and the at least one predefined device control action may comprise displaying information on the display related to modify application of a previously applied predefined device control action.

Thresholds of brain state can be learned from a user. When a person exceeds these thresholds these can be used to video-record scenes that a person is looking at. Patterns of the user's video record can be analyzed to help determine brain state associations with different locations and situations. For example, a therapist can help determine emotional triggers in a patient's environment. Another example is using history of a person's emotional reaction to categories of locations where they have been to suggest mood driven tourism. This is event driven video, labeling video with brain states. The wearable computing device may be configured to always record video, storing at least the previous five minutes to the present time. In this way, the wearable computing device may also maintain a record for five minutes prior to a salient brain event. The device may display and go back in scenes to allow the users to select exact images or section of video that triggered the salient response. The device can generate an ERN to help select the image the user is looking for.

Another application is if the user experiences a stress response then the input can be scrambled to reduce the stress. For instance, a stressful can be altered to break the association. The system can also log when user was grateful for something and then play that back to reinforce because gratitude is highly correlated with happiness.

The wearable computing device has potential to be a companion and help process our negative emotions and turn frustration and anger into humor by altering stressful stimuli into humorous situations displayed on the device.

Analysis of EEG brainwaves of the wearer in combination with facial recognition of people can be used to inform conversations by providing private feedback to the wearer of the device by private bone conduction audio and private visual display. Identification of the other person can be used to get publicly available information from social media or other sources to help inform interaction. In addition, the emotional state of the other person can be inferred by using other information such as voice stress analysis, facial expression, body language, and through amplification of colour changes in skin related to heart beat. In other cases, other users may be willing to share their information with others to enhance the level of communication. The wearable computing device can provide other helpful information to its wearer to help with challenging (or not so challenging) interactions with other people.

Using brainwaves such as error-related negativity (ERN) can be used to determine when a wearer of the device has made a conscious or unconscious error. The detection of an error can be used in combination with a person is looking at or listening to help provide mechanisms such as video image in the device display to provide private information to the user to correct the error.

A supervisor or operations control centre can see what the wearer of muse is seeing and hearing. This information in combination with the wearer's brain state (e.g. stress, frustration, anger etc.) can be used by the wearer or by the operations control centre to help guide the wearer through a difficult situation. This can be used in police work, for example.

Using brainwaves such as P300 wave can be used to determine when a wearer of the wearable computing device of the present invention has recognized something novel or unusual. The detection of novelty or recognition can be used in combination with what a person is looking at or listening to help provide guidance to what additional actions to take. This can be used by law enforcement to pursue a suspect or missing person that has created a recognition brain state even if it is below the conscious awareness of the wearer.

Using the wearable computing device with functionality that is able to determine the type and quantity of food consumed can be used in combination with a wearer's brain state to identify episodes that are based on emotional eating. This knowledge can help with strategies to help prevent emotional eating or at least to healthier alternatives.

Brain state can be used to drive augmented reality in a user's private display or audio speaker. For example, a user's peripheral vision is darkened and noise cancellation can be used to prevent visual and audio distractions to allow them to focus on a task. In another use case, a person can be rewarded by exhibiting a positive frame of mind when learning or doing a task in addition to augmented reality of how to do the task. For example, learning to play golf requires simultaneous being relaxed and focused. This state can be rewarded while augmented reality shows the golfer where to place their feet relative to the ball.

The wearable computing device may use brain state information in combination with a digital personal assistant that helps keep a person organized and provide timely and relevant information without extraneous information (e.g. a commercial example is Google Now). The digital assistant needs to learn the user's preferences. Brain states such as like/dislike, error perception, etc. can be used to train a personal assistant's understanding of the user's preferences. These brain states can also be used to help the digital assistant provide advice aligned with the brain state of the user.

Processing Bio-Signal Measurements

In addition to or instead of processing bio-signal measurements on the wearable computing device, the wearable computing device may communicate with one or more computing devices in order to distribute, enhance, or offload the processing of the bio-signal measurements taken or received by the wearable computing device. In particular, the one or more computing devices may maintain or have access to one or more databases maintaining bio-signal processing data, instructions, algorithms, associations, or any other information which may be used or leveraged in the processing of the bio-signal measurements obtained by the wearable computing device. The computing devices may include one or more client or server computers in communication with one another over a near-field, local, wireless, wired, or wide-area computer network, such as the Internet, and at least one of the computers may be configured to receive signals from sensors of the wearable computing device.

The wearable computing device may further be in communication with another computing device, such as a laptop, tablet, or mobile phone such that data sensed by the headset through the sensors may be communicated to the other computing device for processing at the computing device, or at one or more computer servers, or as input to the other computing device or to another computing device. The one or more computer servers may include local, remote, cloud based or software as a service platform (SAAS) servers. Embodiments of the system may provide for the collection, analysis, and association of particular bio-signal and non-bio-signal data with specific mental states for both individual users and user groups. The collected data, analyzed data or functionality of the systems and methods may be shared with others, such as third party applications and other users. Connections between any of the computing devices, internal sensors (contained within the wearable computing device), external sensors (contained outside the wearable computing device), user effectors (components used to trigger a user response), and any servers may be encrypted. Collected and analyzed data may be used to build a user profile that is specific to a user. The user profile data may be analyzed, such as by machine learning algorithms, either individually or in the aggregate to function as a BCI, or to improve the algorithms used in the analysis. Optionally, the data, analyzed results, and functionality associated with the system can be shared with third party applications and other organizations through an API. One or more user effectors may also be provided at the wearable computing device or other local computing device for providing feedback to the user, for example, to vibrate or provide some audio or visual indication to assist the user in achieving a particular mental state, such as a meditative state.

A cloud-based implementation for processing and analyzing the sensor data may provide one or more advantages including: openness, flexibility, and extendibility; manageable centrally; reliability; scalability; being optimized for computing resources; having an ability to aggregate information across a number of users; and ability to connect across a number of users and find matching sub-groups of interest. While embodiments and implementations of the present invention may be discussed in particular non-limiting examples with respect to use of the cloud to implement aspects of the system platform, a local server, a single remote server, a SAAS platform, or any other computing device may be used instead of the cloud.

In one implementation of the system of the present invention, a Multi-modal EEG Data-Collection and Adaptive Signal Processing System (MED-CASP System) for enabling single or multi-user mobile brainwave applications may be provided for enabling BCI applications. This system platform may be implemented as a hardware and software solution that is comprised of an EEG headset such as the wearable computing device of the present invention, a client side application and a cloud service component. The client side application may be operating on a mobile or desktop computing device. The system may provide for: estimation of hemispheric asymmetries and thus facilitate measurements of emotional valence (e.g. positive vs. negative emotions); and better signal-t-noise ratio (SNR) for global measurements and thus improved access to high-beta and gamma bands, which may be particularly important for analyzing cognitive tasks such as memory, learning, and perception. It has also been found that gamma bands are an important neural correlate of mediation expertise.

In the same or another non-limiting exemplary implementation, possible MED-CASP system features may include: uploading brainwaves and associated sensor and application state data to the cloud from mobile application; downloading brainwave & associated data from the cloud; real-time brain-state classification to enable BCI in games or other applications; transmitting real-time brain-state data to other users when playing a game to enable multi-user games; sharing brainwave data with other users to enable asynchronous comparisons of results; sharing brainwave data to other organizations or third party applications and systems; and support of cloud based user profiles for storing personal information, settings and pipeline parameters that have been tuned to optimize a specific user's experience. In this way, usage of the system platform can be device independent.

Each time analysis or processing of user bio-signal data (such as brainwave data) is performed, an instance of aspects of the software implementing the analysis functionality of the present invention may be generated by the wearable computing device, initiated at either the device or the cloud, in order to analyze the user's private bio-signal data using particular analysis or processing parameters applied during the analysis or processing. For simplicity, such an instance may be referred to as an algorithm "pipeline". Each instance of the pipeline may have an associated pipeline identifier ("ID"). Each pipeline may be associated with a particular activity type, user, bio-signal type of a particular user, application, or any other system platform-related data. Each pipeline may maintain particular pipeline parameters determined to analyze the user's bio-signal data in a particular way, consistent either with previous analysis of the particular user's bio-signal data, consistent with previous analysis of one or more other user's bio-signal data, or consistent with updated data at the cloud server derived from new or updated scientific research pertaining to the analysis of bio-signal data. Pipelines and/or pipeline parameters may be saved for future use at the client computing device or at the cloud. When a new pipeline is created for the user, the wearable computing device or the cloud may provide a new algorithm pipeline ID to be associated with the new pipeline at the cloud and at the device.

Each person's brainwaves are different, therefore requiring slightly different tunings for each user. Each person's brain may also learn over time, requiring the system platform to change algorithm parameters over time in order to continue to analyze the person's brainwaves. New parameters may be calculated based on collected data, and may form part of a user's dynamic profile (which may be called bio-signal interaction profile). This profile may be stored in the cloud, allowing each user to maintain a single profile across multiple computing devices. Other features of the same or another non-limiting exemplary implementation may include: improving algorithms through machine learning applied to collected data either on-board the client device or on the server; saving EEG data along with application state to allow a machine learning algorithm to optimize the methods that transform the user's brainwaves into usable control signals; sharing brainwave data with other applications on mobile device through a cloud services web interface; sharing brainwave data with other applications running on client devices or other devices in the trusted network to provide for the user's brainwave data to control or effect other devices; integration of data from other devices and synchronization of events with brainwave data aid in context aware analysis as well as storage and future analysis; performing time locked stimulation and analysis to support stimulus entrainment event-related potential ("ERP") analysis; and data prioritization that maximizes the amount of useful information obtainable from an incomplete data download (i.e. data is transmitted in order of information salience). The core functionality of the MED-GASP system may be wrapped as an externally-usable library and API so that another developer may use the platform's features in the developer's application(s). The library may be a static library and API for Unity3D, iOS, Android, OSX, Windows, or any other operating system platform. The system platform may also be configured to use a pre-compiled algorithm supplied by a third party within the library, including the ability for a third party developer using the library, to use the developer's own algorithms with the library. The system platform may also support headsets from a variety of vendors; personal data security through encryption; and sharing of un-curated data (optionally using time-limited and fidelity limited access) though the sharing of encryption keys.

Optionally, the wearable computing device of the present invention may be used to implement aspects of the systems and methods described in PCT Patent Application No. PCT/CA2013/000785, filed Sep. 16, 2013, the entirety of which is incorporated by reference herein. Accordingly, the wearable computing device may be used with a computer network implemented system for improving the operation of one or more biofeedback computer systems. The system may include an intelligent bio-signal processing system that is operable to: capture bio-signal data and in addition optionally non-bio-signal data; and analyze the bio-signal data and non-bio-signal data, if any, so as to: extract one or more features related to at least one individual interacting with the biofeedback computer system; classify the individual based on the features by establishing one or more brainwave interaction profiles for the individual for improving the interaction of the individual with the one or more biofeedback computer systems, and initiate the storage of the brain waive interaction profiles to a database; and access one or more machine learning components or processes for further improving the interaction of the individual with the one or more biofeedback computer systems by updating automatically the brainwave interaction profiles based on detecting one or more defined interactions between the individual and the one or more of the biofeedback computer systems.

Optionally, the wearable computing device may be used to implement aspects of the systems and methods described in PCT Patent Application No. PCT/CA2013/001009, filed Dec. 4, 2013, the entirety of which is incorporated by reference herein. Accordingly, the wearable computing device may be used with a computer system or method for modulating content based on a person's brainwave data, obtained by the sensors of the wearable apparatus of the present invention, including modifying presentation of digital content at at least one computing device. The content may also be modulated based on a set of rules maintained by or accessible to the computer system. The content may also be modulated based on user input, including through receipt of a presentation control command that may be processed by the computer system of the present invention to modify presentation of content. Content may also be shared with associated brain state information.

Optionally, the wearable computing device may be used to implement aspects of the systems and methods described in PCT Patent Application No. PCT/CA2014/000004, filed Jan. 6, 2014 the entirety of which is incorporated by reference herein. Accordingly, the wearable computing device may be used with a computer system or method for guiding one or more users through a brain state guidance exercise or routine, such as a meditation exercise. The system may execute at least one brain state guidance routine comprising at least one brain state guidance objective; present at least one brain state guidance indication at the at least one computing device for presentation to at least one user, in accordance with the executed at least one brain state guidance routine; receive bio-signal data of the at least one user from the at least one bio-signal sensor, at least one of the at least one bio-signal sensor comprising at least one brainwave sensor, and the received bio-signal data comprising at least brainwave data of the at least one user; measure performance of the at least one user relative to at least one brain state guidance objective corresponding to the at least one brain state guidance routine at least partly by analyzing the received bio-signal data; and update the presented at least one brain state guidance indication based at least partly on the measured performance. The system may recognize, score, and reward states of meditation, thereby optionally gamifying the experience for the user. The system, using bio-signal data measurements measured by the wearable computing device, and in particular brainwave state measurements, may change the state of what is displayed on the display of the wearable computing device. For example, in response to a determination that the user has achieved a particular brain state, or maintained a particular brain state for a period of time, the wearable computing device may update the display to provide an indication of the determination (e.g. indicating to the user what brain state has been achieved, and, optionally for how long) and may further display an indication of a particular reward assigned to the user in response to the determination.

EMBODIMENTS

FIGS. 1A to 14C each show various non-limiting arrangements of bio-signal sensors mounted, attached, adhered, or otherwise disposed on a user's face or head. While certain exemplary combinations and positions of bio-signal sensors are shown in the figures, the skilled person will understand that other combinations and positions are possible without departing from the scope of the present invention.

Figure 5:
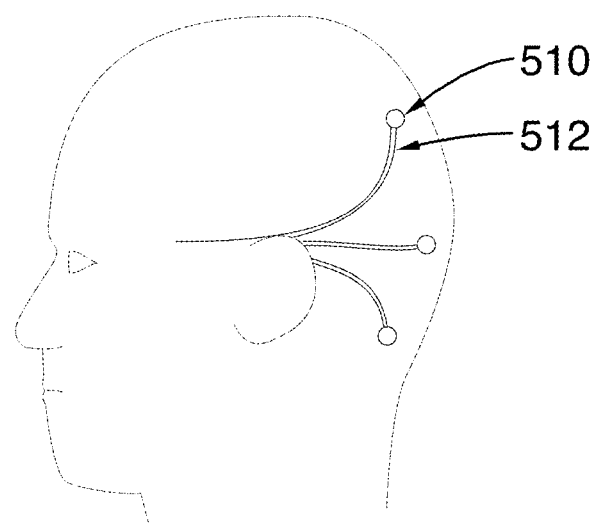
FIG. 5 illustrates a side elevation view of another possible implementation of the invention.
Figure 6A:
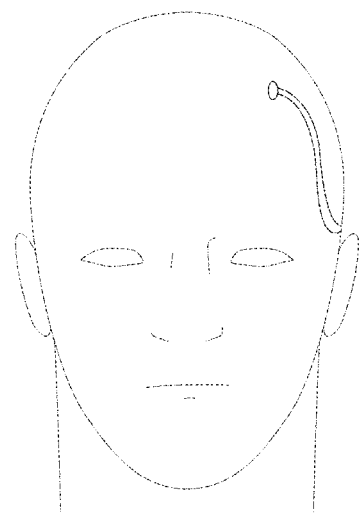
FIGS. 6A to 6C illustrate front elevation, side elevation, and perspective views, respectively, of another possible implementation of the invention.
Figure 6B:
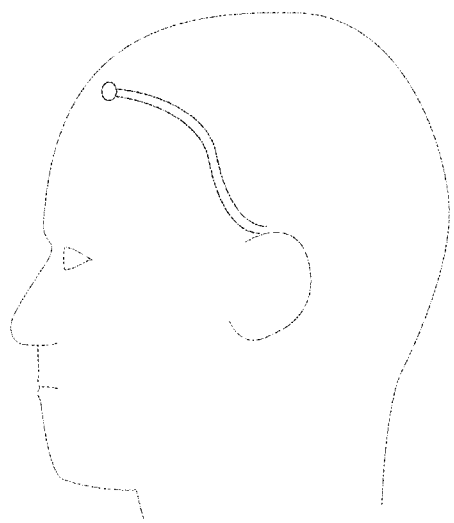
Figure 6C:
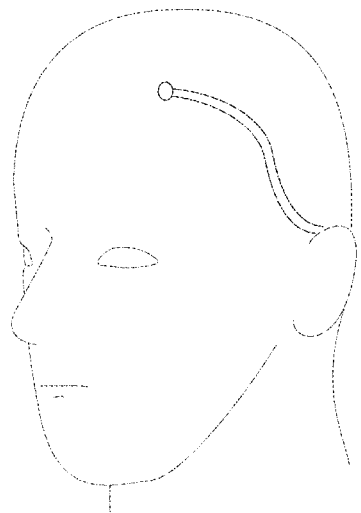
Figure 7A:
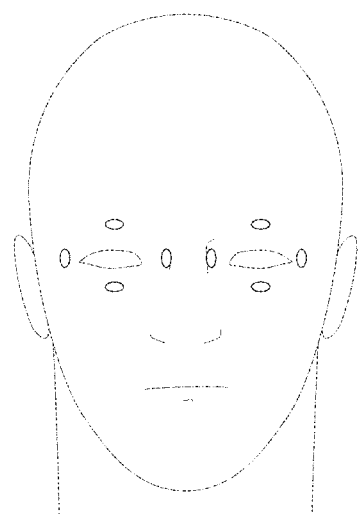
FIGS. 7A to 7C illustrate front elevation, side elevation, and perspective views, respectively, of a possible implementation of the invention.
Figure 7B:
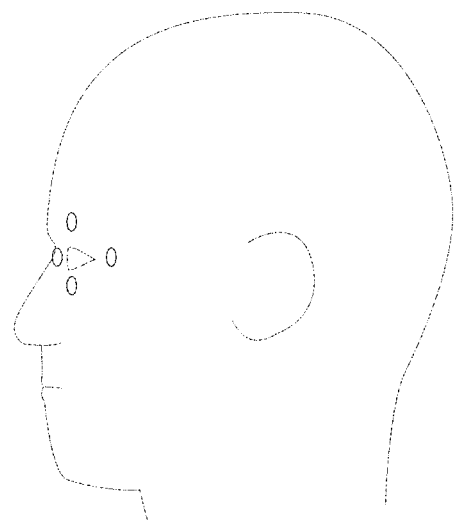
Figure 7C:
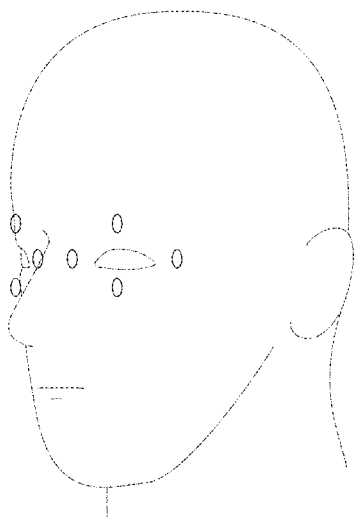
Figure 8A:
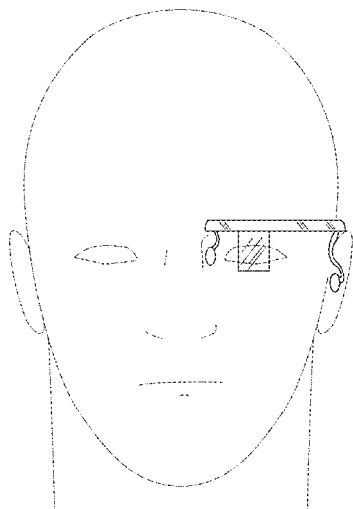
FIGS. 8A to 8C illustrate front elevation, side elevation, and perspective views, respectively, of another possible implementation of the invention.
Figure 8B:
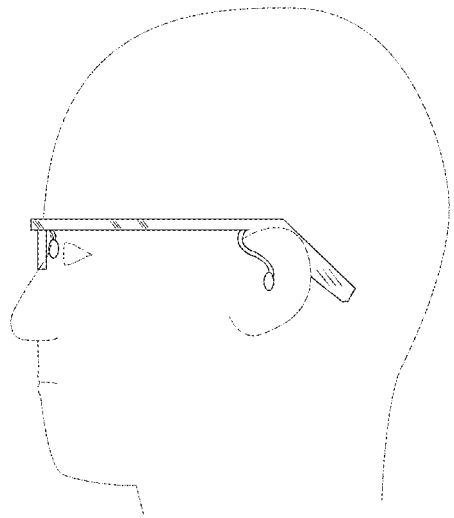
Figure 8C:
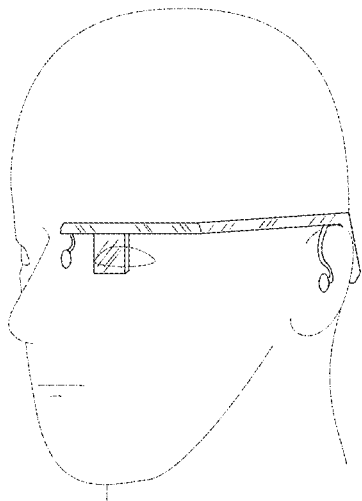
Figure 9A:
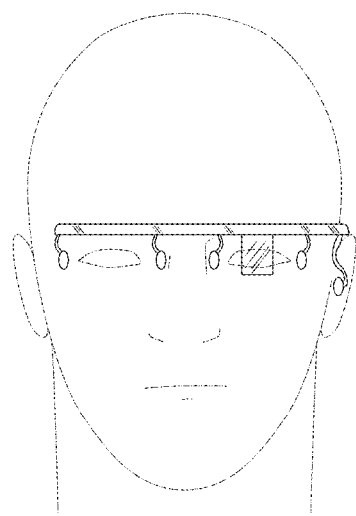
FIGS. 9A to 9C illustrate front elevation, side elevation, and perspective views, respectively, of another possible implementation of the invention.
Figure 9B:
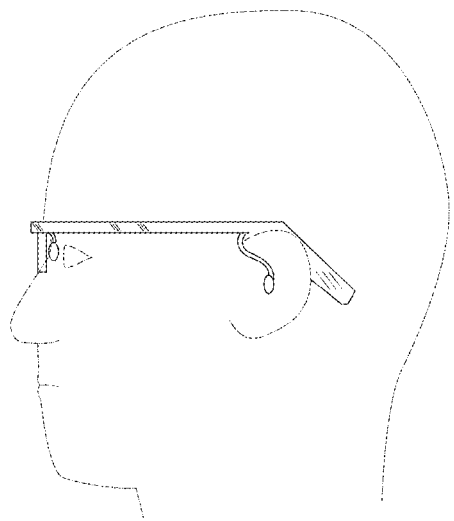
Figure 9C:
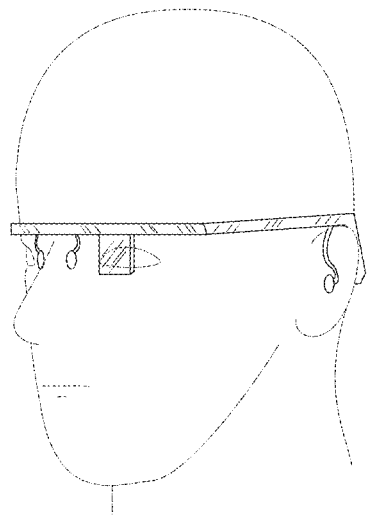

FIG. 5 shows three bio-signal sensors 510 positioned at the back or near the back of the head. The sensors 510 may be attached, as shown, via a cord or band 512 in order to relatively secure the position of the sensors 510. Each sensor 510 may monitor p300 waves to obtain p300 wave data, described in more detail later.

Figure 1B:
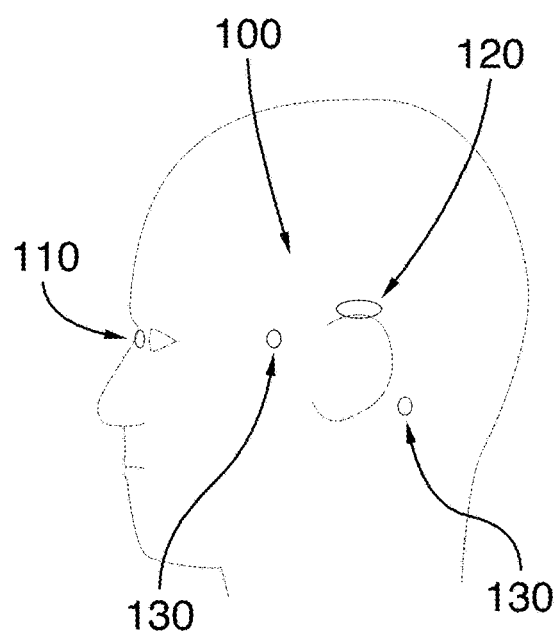
Figure 1C:
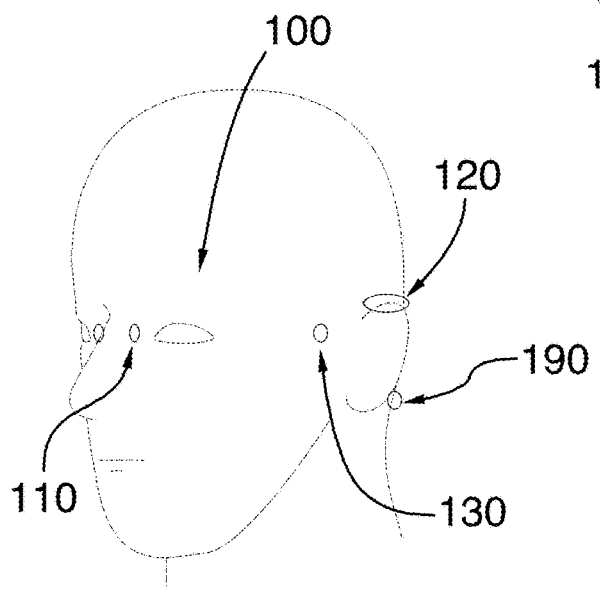
Figure 10A:
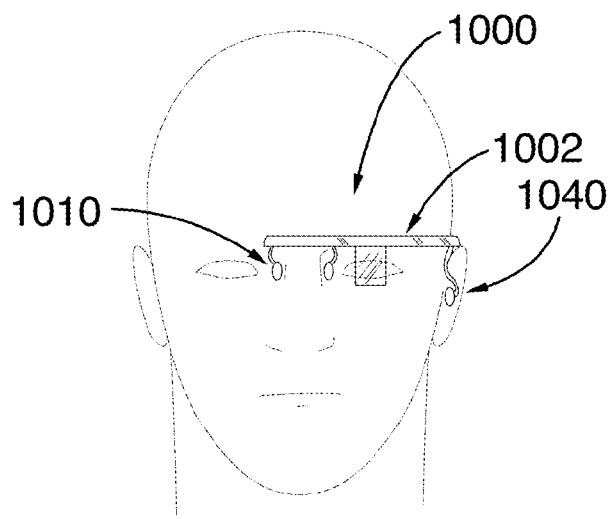
FIGS. 10A to 10C illustrate front elevation, side elevation, and perspective views, respectively, of a possible implementation of the invention.
Figure 10B:
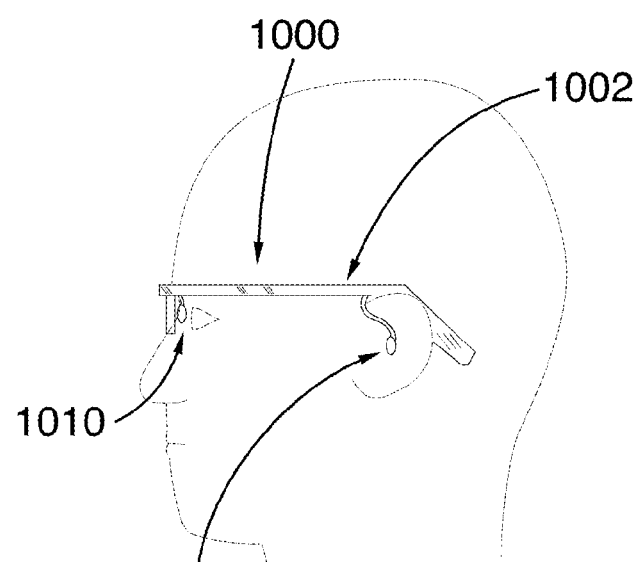
Figure 10C:
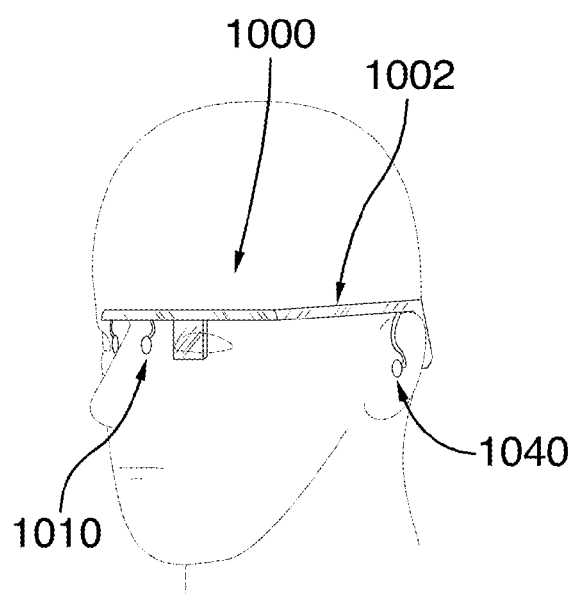
Figure 11A:
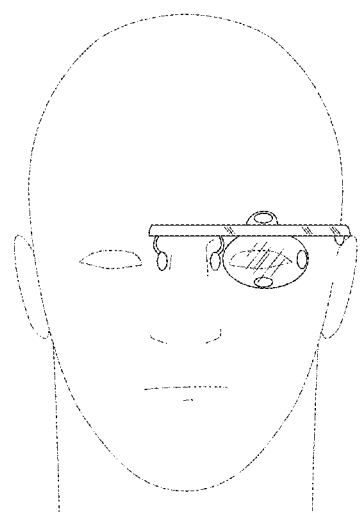
FIGS. 11A to 11C illustrate front elevation, side elevation, and perspective views, respectively, of another possible implementation of the invention.
Figure 11B:
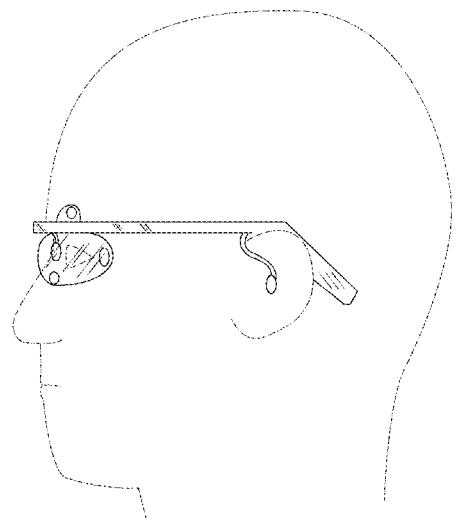
Figure 11C:
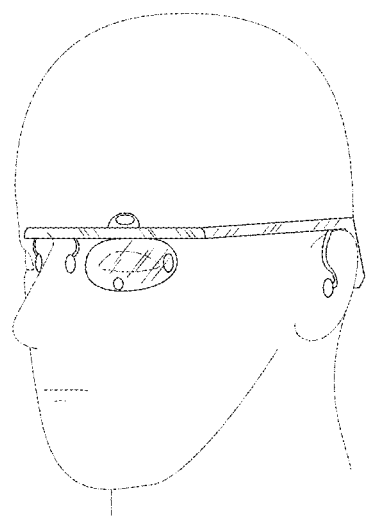
Figure 12A:
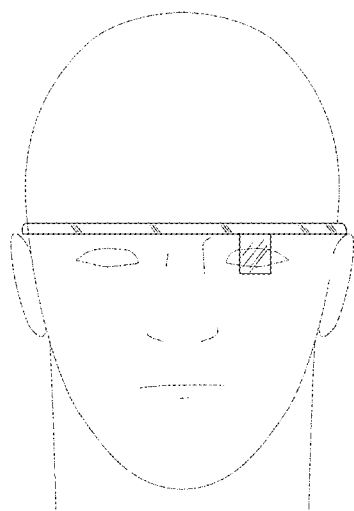
FIGS. 12A to 12C illustrate front elevation, side elevation, and perspective views, respectively, of another possible implementation of the invention.
Figure 12B:
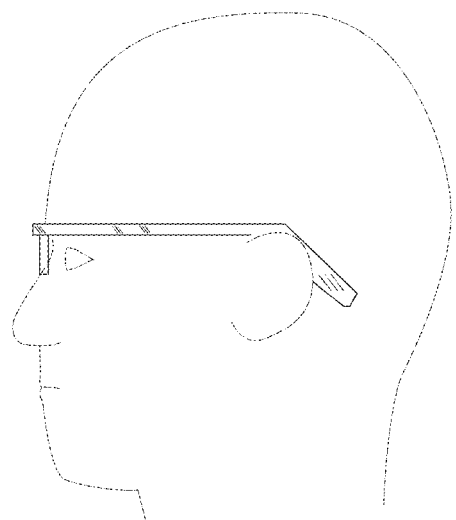
Figure 12C:
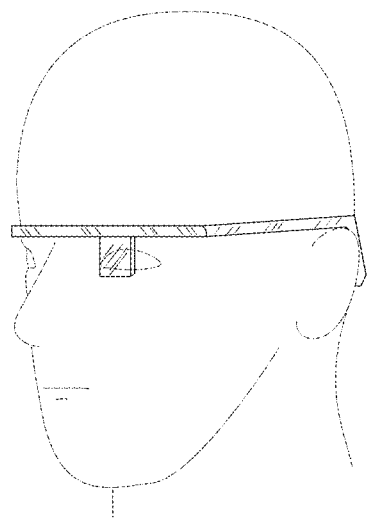
Figure 13A:
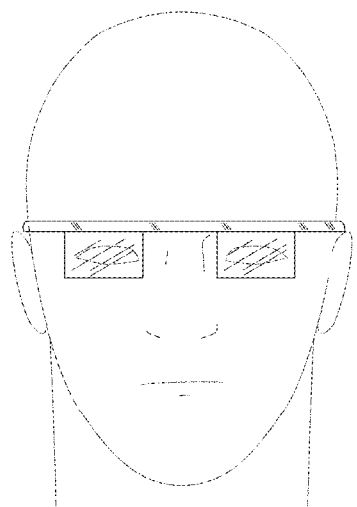
FIGS. 13A to 13C illustrate front elevation, side elevation, and perspective views, respectively, of another possible implementation of the invention.
Figure 13B:
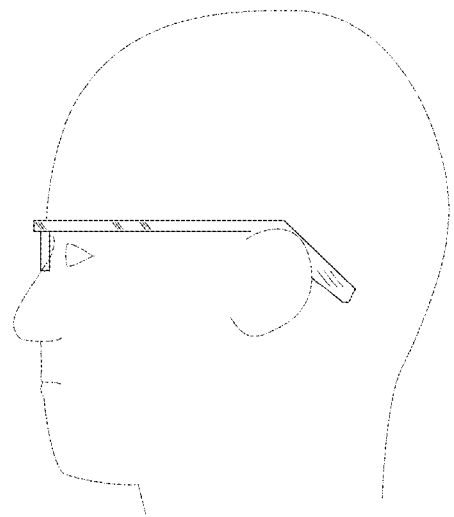
Figure 13C:
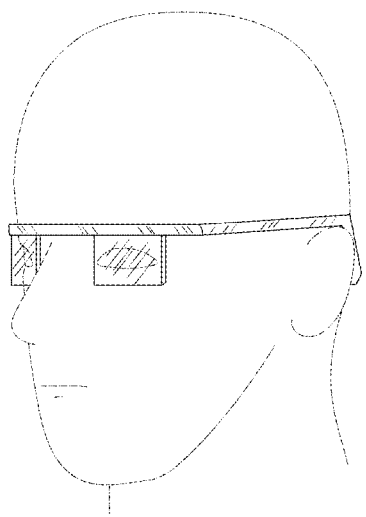
Figure 14A:
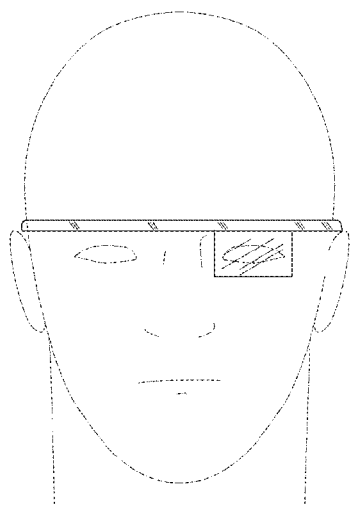
FIGS. 14A to 14C illustrate front elevation, side elevation, and perspective views, respectively, of another possible implementation of the invention.
Figure 14B:
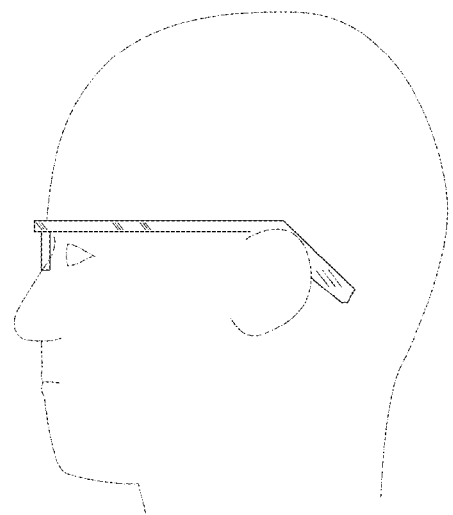
Figure 14C:
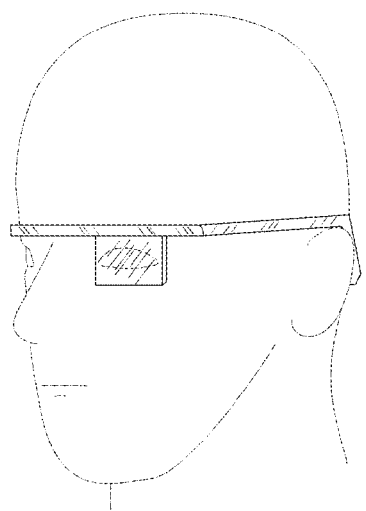

FIGS. 1A-1C show two bio-signal sensors 110 of the wearable computing device 100 positioned on either side of the user's nose bridge. In one example, each sensor 110 may include EOG functionality in order to use EOG to measure eye properties. Optionally, each sensor 110 may measure eye saccades, which may be fast, simultaneous movements of both eyes. Where only one sensor 110 is positioned on either side of the user's nose bridge, mainly eye movement in a relatively horizontal plane may be measured. The sensors 110 may be in the form of pads placed on the nose bridge. Alternatively, as shown in FIGS. 10A-10C, bio-signal sensor 1010 may be attached or built-in to frame 1002 of the wearable computing device 1000. Bio-signal sensors 110 or 1010 may further employ EEG usable by the wearable computing device 100 or 1000 to determine horizontal EOG.

FIGS. 1A-1C further show a bio-signal sensor 130 positioned at the temporalis muscle. In one example, sensor 130 may measure activity in the temporal lobe, such as firing of muscles usable by the wearable computing device 100 to determine muscle activity or muscle movement. In the embodiment shown in FIGS. 10A-10C, a bio-signal sensor, not shown, similar to sensor 130 may be positioned in the arm portion of the frame 1002 along the user's temple and obscured from view underneath the frame 1002. This sensor may be of a continuous shape disposed along an arm portion of the frame 1002 or the sensor may be a discreet shape positioned at a particular spot along the frame 1002.

FIGS. 10A-10C further show bio-signal sensor 1040 positioned inside the ear. Sensor 1040 may be disposed on an earbud-shaped element for inserting in, at, or on the ear. The earbud-shaped element may be connected to frame 1002 by a rigid or flexible arm, cable, or other connection. The sensor 1040 may be wrapped all or partially around the earbud-shaped element, which may provide for a firm contact to be made with the user's ear.

FIGS. 1A-1C show bio-signal sensor 120 positioned above the ear, and bio-signal sensor 150 positioned behind the ear. Each of the sensors 120 and 150 may be further disposed in or along frame 1002, making contact either against the side of the head, or behind the ear, and may be obscured by frame 1002. One or more bio-signal sensors may also be deployed in a band of the wearable computing device disposed behind the user's head, optionally connecting arms of frame 1002.

Figure 2A:
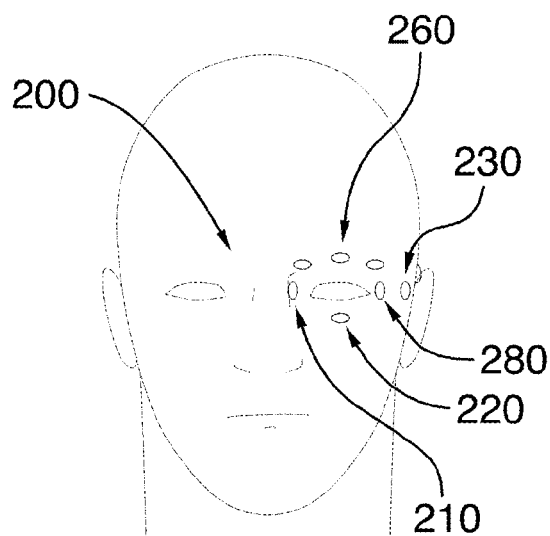
FIGS. 2A to 2C illustrate front elevation, side elevation, and perspective views, respectively, of another possible implementation of the invention.
Figure 2B:
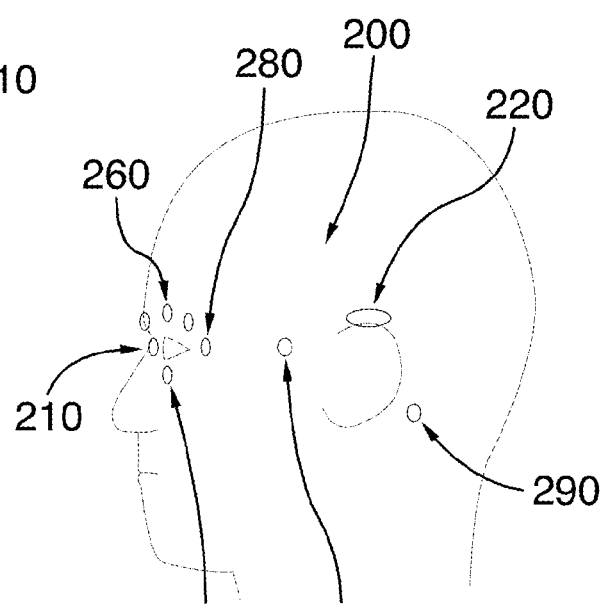
Figure 2C:
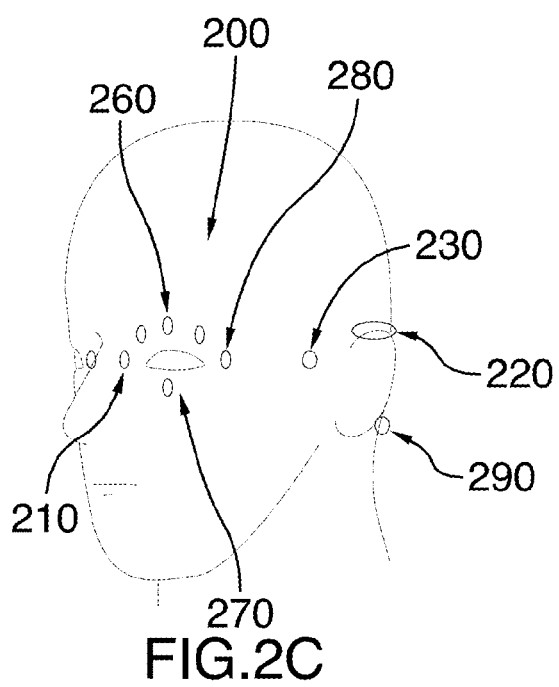
Figure 3A:
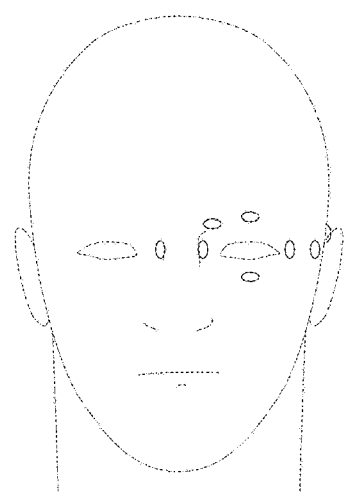
FIGS. 3A to 3C illustrate front elevation, side elevation, and perspective views, respectively, of another possible implementation of the invention.
Figure 3B:
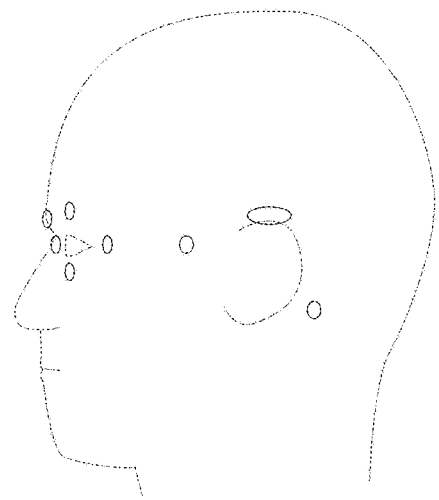
Figure 3C:
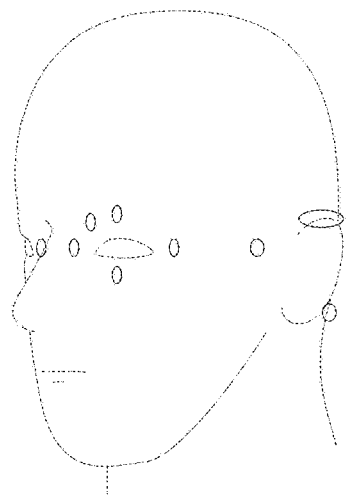
Figure 4A:
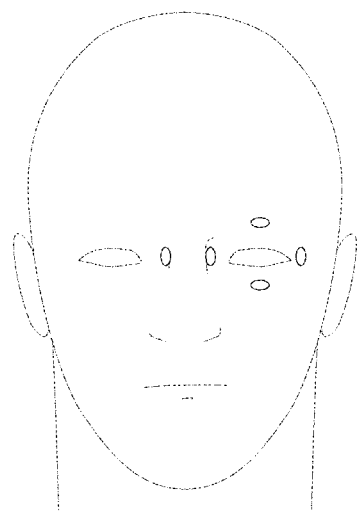
FIGS. 4A to 4C illustrate front elevation, side elevation, and perspective views, respectively, of a possible implementation of the invention.
Figure 4B:
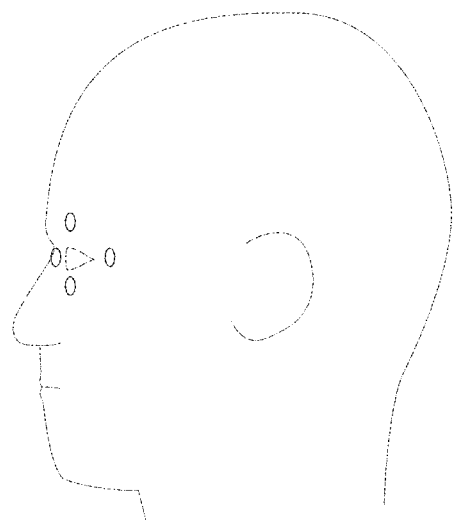
Figure 4C:
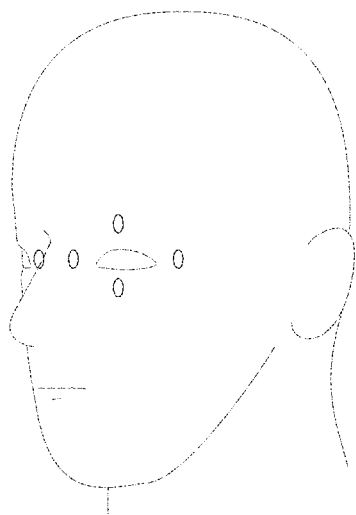

FIGS. 2A-2C shows another possible arrangement of bio-signal sensors in accordance with an aspect of the present invention. Wearable computing device 200 is shown comprising sensors 210, 220, 230, and 250, which may respectively correspond in position and functionality to sensors 110, 120, 130, 1040, and 150 previously described. As shown, wearable computing device 200 may further comprise at least one sensor 260 positioned above one of the user's eyes. In FIGS. 2A-2C, three sensors 260 are shown positioned above the eye. These sensors may be used to measure activity in the user's frontal lobe. Each of the sensors 260 may be further disposed in or along frame 1002. Sensor 260 may rest on a top edge of frame 1002, or on an arm of frame 1002 positioned off the eye bridge or the arm. Sensor 270 is also shown positioned below the eye. Wearable computing device 200 may also further comprise sensor 280 positioned at one edge of the eye. Sensor 280 may be used to measure horizontal eye objective refraction ("EOR").

FIGS. 3A-3C, 4A-4C, 6A-6C, and 7A-7C show other combinations of bio-signal sensors positioned at various locations on the user's head. FIGS. 8A-8C, 9A-9C, 10A-10C, 11A-11C, 12A-12C, 13A-13C, 14A-14C, 40A-40C, 41A-41C, 42A-42C, 43A-43C, 44A-44C, and 45A-45C show implementations of the wearable computing device as part of an eyeglass frame worn on the user's head. Where an eyeglass frame is shown, the display may be at a close proximity to the eye. The display may cover all of or a portion of the eye. When not displaying an image, the display may be substantially clear or transparent.

A variety of brain-computer interface ("BCI") paradigms may be employed in the wearable computing device. As explained previously, p300 wave data may be measured by at least one bio-signal sensor of the wearable computing device. Using p300 wave data, the wearable computing device may determine the salience of a stimulus. For example, when presented with a group of objects to look at, the user may focus on one of the objects more than the others. The wearable computing device may interpret the p300 wave data, optionally in conjunction with other inputs from the user, in order to determine which of the group of objects, the user has selected. For example, if a user searches for the term "apple", by optionally verbally communicating such a search command to the wearable computing device, and a set of images are presented in the display in response (e.g. green apple, apple tree, Apple computer, etc.), the p300 event-related potential ("ERP") may be detected 300 ms after the image that is of interest or salience to the user arises. Using p300 methods, for example, as used in p300 spellers, it is possible to correlate the p300 activity with the image of interest, and determine that the image, or images are the ones that are of interest to the viewer. This allows for a selection or narrowing of search terms. By tracking eye movements in combination with processing p300 wave data for conducting searches, such as internet web searches, it may be possible to refine a search, select search terms, or otherwise navigate graphical interfaces rapidly.

Another BCI paradigm employable by the wearable computing device is EOG. As described previously, EOG measurements may be obtained by sensors positioned on either side of the nose bridge, or sensors positioned on the inside and outside edges of the eyes on the lateral plane. At least some of these sensors may measure EOG to track eye saccades thereby determining where the eyes are looking in the horizontal plane with respect to the user's head. Similarly, sensors above and below the eye may measure EOG to track eye saccades thereby determining where the eyes are looking in the vertical plane. In one example, EOG measurements from lateral and or vertical eye movement could be used by the wearable computing device to determine whether the user has looked at a recent message. If the wearable computing device makes such a determination, an action could be performed such as clearing the message once the user has looked at it. Optionally, the wearable computing device may process EOG measurements together with eye blink detection to allow for further control. For example, the wearable computing device may look for movement of the user's eye up and to the right. If the user looks in this way for a predetermined period of time, then blinks, the wearable computing device may be configured to clear the message from view. A skilled reader will understand that various other implementations are possible.

In another example, p300 wave data may be used by the wearable computing device to determine whether the user has seen a message displayed on the display. The wearable computing device may flash the message until the user produces an ERP. Using both EOG and p300 wave data together to determine where the user's eyes are looking and any image(s) that are of interest to the viewer may have particular applicability in selecting items for search, or using in searching generally. By combining EOG eye tracking with p300 wave data, it may be possible to train the wearable computing device by showing fewer presentations of a stimulus than is required to train a system only with p300 wave data as an input. However, even with both EOG and p300 inputs, false positives may occur. For example, where the user is searching for "apple" looking for a green apple and the user sees a picture of a famous person holding an apple, by the user recognizing the person, an ERP might be detected, and the user might look back at the picture multiple times, but even with false positives, combining both EOG and p300 may still be an improvement for conducting searches. Furthermore, the combination of EOG and p300 detection may be used when one or both eyes are closed or in total darkness. The time of eye movements can also be detected.

Steady state visually evoked potentials (SSVEP) may also be measured by bio-signal sensors employed by the wearable computing device. When an object is flashing at a certain frequency, that frequency can be detected in the head. This can be used to select objects. For example, if several images on the display are flashing at different frequencies from one another, and the user looks at one of the images indicating an interest in that image, the wearable computing device may determine this interest by detecting the frequency at which the object is flashing by measuring the user's EEG. In another example, if there are two images on screen, and image A is flashing at 7 hz and image B at 5 hz, and a steady 5 hz wave is detected in the viewer's EEG, then it can be determined that the viewer was interested in object B. The wearable computing device may therefore be configured to conclude the user wishes to select this image, or that the user is interested in receiving more information about the image. Optionally, upon detecting interest in the 5 hz signal in this example, a selection of predefined actions may be displayed, each also flashing at different frequencies, such as "more info", "next", and "not interested". Measuring the user's EEG again may allow the user to control the display of images and information on the wearable computing device display.

Left and right hemispheric specialization may also be detected by at least two sensors on the user's forehead, one on each side of the forehead. Measurements obtained by these sensors may be used by the wearable computing device to make a determination between two distinct choices, for example opposite choices such as like/dislike or yes/no.

With respect to measured motor imagery, by reading over the electrode positions of c3 and c4, a user may imagine the movement of the user's right or left hand, and use the resulting measured data to navigate in directions such as left or right One method to determine focus is to determining the relative proportion of beta power from frontal electrodes. Other methods look at frontal-midline theta power, as well as EMG to determine muscle activity in the face associated with concentration.

The wearable computing device could be configured to determine particular brain states of the user and then reward the user for achieving this state by displaying an indication on the display, or encourage the user to achieve the desired brain state with other messages or indications on the display. For example, when the user is determined to be engaged with an activity, content on the display may be tailored based on the user's level of engagement. This could be used to train attention or engagement, for example, the user's behaviour could be reinforced or rewarded for maintaining attentive states. Similarly, the wearable computing device could encourage brain states that are associated with learning, so the user could learn content more effectively. For example, if the user reads information from a source such as Wikipedia, that the user wishes to remember, the wearable computing device may reinforce the brainwave state associated with learning by providing an indication of a sound, vibration, colour, etc. where the state is successfully entered. In another example, the wearable computing device may track the user's level of engagement while working and remind the user when the user's mind has wandered away from work. The wearable computing device may further display information to improve your workday and workflow, like when to take a break. Accordingly, the wearable computing device may provide the user with a means of tracking focus/engagement via brainwaves and other waves so the user may better understand the user's own working patterns.

Similarly, the wearable computing device could ameliorate attention deficit disorder ("ADD") symptoms by reinforcing beta waves and down-regulating theta waves, or by reinforcing slow cortical potentials. This could be an alternative to treatment by prescription medication. The wearable computing device could track time corresponding to when the user was paying attention for later review by either the child or parent In accordance with an aspect of the present invention, the wearable computing device may implement any of the bio-signal collection methods and systems using bio-signal data described in U.S. Patent Application Nos. 61/701,002, 61/750,177, 61/733,223, and 61/701,176, the entirety of which are incorporated herein by reference. With respect to each of these references, the wearable computing device, optionally in glasses form, may replace the computer, smartphone or tablet described as being normally used. Processing in accordance with the incorporated references may also occurs on the wearable computing device. The wearable computing device may detect an increase in alpha wave activity (power), or a downshift in the alpha frequency, or an increase in theta activity, and use this input as a trigger for positive feedback in a relaxation or meditation experience, by playing calming or pleasing audio or visuals that reinforce the increased alpha or theta activity and associated relaxation/meditation state.

Optionally, the wearable computing device may include an optical sensor and transmitter placed facing the skin to measure the user's heart rate.

Optionally, measurements of the user's facial expressions or emotional response may be taken by performing ectromyogram ("EMG") measurements, and associated expressions or emotions may be determined by the wearable computing device.

In an implementation, the wearable computing device may be configured to interpret various sensor measurements described previously in order to control navigation and use of a social networking environment. In particular, for the purposes of tagging photos, the wearable computing device may present one image at a time on the display and ask the user to look at each person shown in the photo. Where the wearable computing device determines, using some combination of EEG, EMG, EOG, and p300 that the user recognizes the person, then the wearable computing device might either prompt the user to say the person's name, or a sequence of images each showing an individual person that the wearable computing device determines is known to the user (such as people listed in the user's friends list, or people recently tagged in a photo by the user) may be displayed. Based on the user's measured response to this sequence of images, the wearable computing device may determine which, if any, of the displayed people is to be tagged in the photo. Similar methods may be employed for tagging other data to images such as date, time, and location. Furthermore, the user's measured response may, in addition to sending data to a social network, also prompt the wearable computing device to send some associated data directly to a specified person or someone who is a frequent contact of the user.

Optionally, the wearable computing device may provide for tagging photos, updates and messages shared on a social network, such as Facebook or Google Plus, with the emotions and brain states that were felt when the messages were originally created, when the photo or video was taken or shared, or when the readers/message recipient(s) within the social network read/receive the photo/update/message/video. For example, photos may be tagged with an emotion measured by the wearable computing device when the photo was created, acquired, or looked at by the user. The photos may be tagged with a corresponding emoticon or other proxy for emotion, indicating the user's emotional response at one time associated with the photo, such as a smiling face, perplexed face, laughing face, etc.

Text messages, email, or any other notification including social network notifications could also be tagged in a similar fashion. For example, if a user has a happy emotional response when seeing a photo of a new family member for the first time, the photo could be automatically tagged with a smiling face, smiling emoticon, or other indication of happiness. This tagging could occur next to the photo, in the comment section associated with it, or by adding a filter that indicated "happiness" to part of the photo or associated texts or comments. Both brainwaves and EMG measurements may be used by the wearable computing device to deduce the emotional or cognitive state of the user, and that information may be used to change the way that information generated at the time is stored. For example, if the user is typing, the text may change based on the user's emotional state (e.g. flowery when the user is happy, bold if the user is excited, tight and sans-serifed if the user is focused). The user may write notes to himself/herself, or messages, texts or emails to others. These can be effected by the users state/emotion by changes in font, type, colour, addition of emoticon or tag indicative of state, etc. They can also be automatically sorted and stored based on this mood or state information. Audio or video that is recorded through the wearable computing device, or photos that are taken, could be tagged with emotional or brain state and used to add contextual information about the user's state at the time of initial recording of the media, or upon reviewing.

The wearable computing device may also monitor user fatigue using at least one of monitored brainwave changes, EMG, EEG, and EOG. With respect to brainwave changes, decreased frequencies indicate fatigue as theta is increased and alpha is decreased. With respect to EMG or EOG, measuring eye blink frequency and duration may indicate fatigue where slower eye blinks correspond to a fatigued state. A user may be determined to be fighting to stay awake when there is a measured downshift in the frequency of alpha.

Optionally, the wearable computing device may present biofeedback exercises to the user during the day that entrain brainwaves in the 13-15 hz range, allowing the user to fall asleep faster at night and maintain some declarative memory improvement.

Optionally, the wearable computing device may also track the user's sleep properties during the night. This could be accomplished by a separate band or stick-on patch with sensors on the forehead that monitor sleep quality via EEG, EMG, EOG or a combination thereof, which could send sleep data back to the wearable computing device glasses during the day. The wearable computing device may use this sleep data to automatically set an alarm clock, or to change the way that data is presented to the user in the display or device, based on how much the user slept. The wearable computing device could recommend customized suggestions based on the quality of your sleep, for example "drink more/less coffee", "eat more/less/at different times of day".

Any of the EMG, EEG or EMG mechanisms described could be used in a gaming context where the user could play audio or visual games using the wearable computing device. For example, in a simplified "tetris" type game, pieces could fall from the top of the screen to the bottom, and the blocks flash at different rates. The user could cause the blocks to disappear by staring at a particular one of the flashing blocks, and triggering a SSVEP indicating the user has have seen it. A consequence of this triggering may be that the more blocks that disappear, the longer the user may play, as blocks pile on top of one another. If the user is unable to prevent the blocks from reaching the top of the screen, the user may lose the game.

Advertisements displayed by the wearable computing device may also be customized by using a like/dislike method as described previously, for example by hemispheric specialization to discriminate preference and then serve ad content informed by determined likes.

Sensors positioned on the wearable computing device could determine if the user is moving the user's eyes left or right using EOG eye tracking measurements. This could be used to select content on screen or to measure a user's interest in a portion of on-screen content being viewed by the user. If, for example, the user is presented with written content, the electrodes could track the user reading down the page, and when the reader's eyes reach the end of the page the next page may be presented, having presumed the viewer completed reading the content displayed. Optionally, a confirmation prompt may appear asking for the user's confirmation to proceed to the next page. Any of the methods previously described may be used to determine whether a use confirmation has been indicated. Optionally, movement of the user's eyes may indicate interest in the "real world" content, not the content on the display of the wearable computing device. Where the viewer was looking may indicate that the content in the real world was of interest, therefore more information about it could be displayed on the display, or the data from that part of the world could be automatically recorded or tagged. Eye movement could also be used as a selection tool. For example, the user deliberately looking left at a certain rate (a rate slower than involuntary eye movements) could indicate that the user wished to select content to the left, or scroll to the left.

In other implementations of the present invention, the wearable computing device may be able to determine the activity the user is performing (e.g. reading, writing, thinking, internal dialogue, making things up, remembering, etc.) employing the various methods previously described.

The wearable computing device may include various modes including a "memory jog" mode, or an "inspire me" mode, enabled by verbal commands such as "glass, jog my memory", "glass, inspire me", or "glass what was I doing", or through eye motions that are related to search, or a combination thereof. When a user looks up and to the right, typically the user is trying to recall something. This is a natural fit with the glasses form-factor, which may ask the user to look up and to the right to use it. The device could, in the absence of other stimulus, or in combination with other stimulus, enter a search mode upon measuring a look up and to the right. ERP may be used for selection purposes. The display may display various messages or images and measure when ERPs are created. In doing so, images and other content may be repeated. The content may then be consolidated and re-presented (possibly by blinking to advance and fixating on the image to increase its importance) to the user in another fashion to refine the search.

The wearable computing device may employ a method of continuous recalibration of ERP detection using an initial message presentation to establish a first calibration of ERP. An ERP may be calibrated by a set of events. In this case, the wearable computing device may be configured to calibrate during natural events that occur over the course of usage of the wearable computing device. For example, the calibrating stimulus may be the interface coming to life, which generates a spontaneous ERP. ERP calibration may also occur after a particular trigger causing the wearable computing device interface to activate from verbal command, fixation based selection (e.g. the user stares at a blinking cursor or the like, for example using SSVEP or by fixating on a single point so the user's eyes are relatively motionless), or other determined input. ERP calibration may also come from a flipbook presentation during memory jog mode. ERP detection can be synchronized to message flipping and can be filtered out using robust statistics, such as iteratively re-weighted least squares, or clustering methods. The wearable computing device may display a memory or stimulus rolodex that plays when the device detects that the user is searching for ideas, answers, or inspiration. The wearable computing device could keep track of common images, words, or sequences that result in action or clearing-of-mind blocks. The wearable computing device could also keep track of environment or sequence lead up that relates to action or progress or inspiration to put in the rolodex. The wearable computing device could provide a replay of the preceding environment where the lost memory was first triggered, when the user is searching the user's memory for lost thought. The wearable computing device could also initiate memory job methods by determining any one of the following inputs, or any other assigned input: (1) interpreting a facial recall expression or brain freeze; (2) a combing hand gesture (e.g. look one direction and swipe); (3) a squint and swipe gesture; and (4) the user closes the user's eyes and empties the mind with an optional swiping gesture. These cues could be programmed by the user or be pre-configured in the wearable computing device.

The wearable computing device may further provide for notification management based on cognitive and emotional state tracking. Any conventional user interface may be adapted to be controlled by any of the inputs measured or determined by the wearable computing device as described previously. The user may select for messages to be delivered based on a choice of when the user would like to receive them. For example, the user could choose to have messages delivered when the user is disengaged or daydreaming or the user could choose to have messaged delivered when the user is focused or attentive. The wearable computing device monitoring bio-signals can be used to separate dis-engagement from thinking, and to identify focus and attention. Messages with a particular priority level may be assigned different presentation conditions. High priority messages may cause interruption at all times. Low priority messages may be optimized for the least interruption at the expense of speed. The user may also choose the mental states where the user wants or does not want to be interrupted. In order to not deliver messages during a fleeting momentary change of mental state, the user may also specify a predefined amount of time that must pass while the user is in a particular mental state before the messaging may occur.

Particular emotional content may be delivered or presented to the user in accordance with a correlation to the user's present emotional state. For example, a message may displayed to the user after measuring that the user has smiled or frowned. The wearable computing device may present rewards for measuring smiles on the user by presenting certain kinds of information when the user is smiling (e.g. avatar-based expression feedback). Similarly, the wearable computing device may provide some sort of sensory penalty for frowning to discourage frowning. The sender of a message may also tag the emotional content of the message with natural or mimicked biometric inputs (e.g. such as a smile or frown) or with manual tagging. An emotional condition may be required to be satisfied from the receive before the receiver may open the message, or before the receiver's device presents the message to the receiver optionally depending on a match of emotional state between message content and receiver.

The presentation of messages may also be modified or adapted in real-time order to reduce stress or optimize observability. For example, message presentation may be tuned so as not to overly distract the user. If for example message presentation creates a very strong response in the user assessed using auditory or visual ERP, facial expressions, gross reflex movements, or other measurements, the presentation ramp may be softened. If it takes too long for the user to notice the message, as assessed by considering the user's eye gaze or message clearing dynamic, then the wearable computing device may increase the presentation ramp up. Presentation may be ramped up gradually increasing notification tone, or by changing the opacity of the message or the dynamics of the message presentation such as blinking duty cycle and rate.

Various methods may be employed by the wearable computing device in order to aid the user in achieving a particular mental state. For example, in dedicated relaxation or stress relief applications not exclusive to the wearable computing device, heads up visual feedback may be provided. For relaxation or stress relief methods integrated into the wearable computing device, the user may need to relax in order to receive certain messages. This may be accomplished by monitoring the user's brain signals such as alpha waves, or physical symptoms such as stillness or muscle tension. In one example, the user may need to be in a relaxed state in order to view a particular video or participate in a particular video conference. The video conference image may optionally be tuned out while the user is thinking. The user may need to be engaged in order for the interface to change at quicker rate. Presentation speed may increase when the user is determined to be focused above a predetermined focus amount.

Various methods may also be employed to affect a user interface by user inputs measured by the wearable computing device. For example, presentation time may be tuned based on brain state. Users may be more able to digest complex information when it is presented at times that are optimal for processing. This optimal state can be discerned from the user's brainwave activity, thereby ensuring that the user's neural resources are aligned before complex information is presented. Message presentation may be synchronized to a phase of low frequency brainwaves, such as the EEG phase. Oscillations in measured theta may trigger presentation of particular content on the display. Delta phase may also be used as a trigger, as well as phase locking of alpha in parietal and occipital regions. The continuous flow of information may be paced base on particular measured brainwave states. A coupling between theta phase and beta power may be an indicator of neural excitability. By using combinations of the above measurements, it may be possible to provide the user's brain with little breaks in information consumption in order to increase comprehension. Information may be presented at higher rate as the user tunes into it. Presentation times may be tuned to be in phase with neural readiness. Presentation rate may decrease when the user blinks, and may slow even more with higher blink frequency or elongated blinks. Greater evidence of fatigue or processing could necessitate that the user take a short time-out where a biofeedback element may be used to help the user recharge.

The wearable computing device may modify the delivery of audio or video media to the user based on measured brainwaves. The user's real-time brain state (e.g. attention, joy, synchronization) may be used to modulate or filter the audio to change the experience to enhance the user's brain state. For example the clarity, colour filtering, contrast, or other properties of a video may be modulated. These types of experiences may also be performed in synchronicity with another user to help multiple users share experience. Delivery of the media may concentrate on aspects that both users find to be engaging. For example, if both users find the vocals in a song being delivered to both users to be captivating the audio may be filtered to accentuate this through band pass filtering or by applying a reverb effect. In video if users are responding to similar areas in a frame, the area may be presented with more saturated colour. Both users may be in control of different effects (e.g. user A controls saturation, user B controls the sharpness) and together the final image is created for delivery to both users. Effects may apply to the whole image and may vary only temporally, or effects could be spatial as well if eye-tracking is employed. Channel encoding may also be one way so that a particular user's cognitive or emotional state may not affect the feed allowing the subsequent observers to observe the encoded (e.g. annotated, highlighted, etc.) content without the confounding aspect of subsequent observer's own experience. Shared experiences may be in real-time or may be asynchronous where one user encodes content and then shares it with another user for that user's experience and subsequent addition.

The wearable computing device may also provide for an emotional or cognitive side channel to be encoded where users are participants in a shared audio or video experience in order to attempt to improve the ability of the users to engage with one another in live conversation or shared experience. The side channel may broadcast measured emotional or cognitive information from each respective user as determined by each user's respective wearable computing device. Colors corresponding to particular emotions may be shared between users. An indication of where each user is looking in the video may be shared. An emotional channel for telephone conversations may also be provided. Visual disruption and distraction measurement for mobile conversations may also be provided.

Bio-signals measured by sensors of the wearable computing device may be used for eye responsive UI interaction. For example fixation measurement, where the user's eye looks in a direction and holds that look may control an aspect of a UI. Blink measurement may also be used, optionally to instruct the wearable computing device to know when the user is attending to messages and to know when to advance the interface (e.g. step to the next message). SSVEP fixation point measurement may instruct the wearable computing device that the user wants to see something particular, or tell the system to display messages. SSVEP further may allow the system to recalibrate the eye gaze detection algorithm such as like a blinking cursor in old computer systems.

The wearable computing device may also employ personal Data capture for memory, documentation, annotation, or QS integration. For example, the wearable computing device may take a picture based on facial emotion recognition perhaps 1 or more seconds ago based on ERP shape likely 300 ms ago. The device may also recognize eye movement that a sawtooth movement of the eyes comes from scanning a motion field rather than from stepping through content. The device may also edit a scene replay based on brain state and facial expressions.

When playing audio or video media, the device may measure p300 wave data and use that data to indicate the salience of an event in the media stream. The portion of the video or audio that corresponds to the p300 firing is tagged accordingly. The user may then jump back to the p300 tagged data, which would have represented something that was salient to the user, meaning it is more likely content the user was interested in reviewing. This may be an effective way to manage reviewing long streams of video/audio. Similarly, the wearable computing device may record video or audio at all times, maintaining a buffer thereof up to a predetermined amount of time in the past. if the camera in the wearable computing device is recording video or not, the unit may take a photo when the p300 fires, or take a photo from the video stream that was 300 ms prior to the firing of the p300 (because p300 fires 300 ms after a stimulus). This would require the device to maintain a minimum 8 frame buffer.

Tagging can also take place via emotions as the user may tag photos, video or audio with the emotion experienced while viewing, and then use those emotion tags to recall or organize the photos, videos, or audio media. The same emotion can be used to recall, or the user may search based on the tagged emotions. In one implementation the device could suggest media to the user based on the user's brainstate. For example, if the user previously tagged photos of kittens as happy, when the system detects that the user is sad, it can suggest that the user look at photos of kittens, or automatically retrieves and presents photos of kittens. Similarly, the wearable computing device may track songs that provoke a particular emotional response in the user and organize or tag the songs based on that emotional response. The device may further suggest songs to the user or auto play songs based on the user's measured emotional state or mood, or the mood that the user indicates to the device that the user would like to achieve. The device may then play music that is associated with the target emotional state.

In an implementation, the wearable computing device may also be used for personal user optimization using Quantified Self ("QS") type tracking. For example, at the end of each day, or at predetermined times, the wearable computing device may upload data measured from the user into a QS application to measure daily performance. The wearable computing device may therefore correlate cognitive and emotional states with activities. The data may presented in compressed timelines on the wearable computing device display. The user may annotate the timeline or data with labels to aid in the device's context-aware behaviour and to allow the user to search by tag later. Reviewing the timeline may also be useful for post-day review for memory consolidation, to relive events in a more comfortable context, or to re-live positive events in stressful moments to improve mood. Similarly, the user may be able to re-live stressful events in positive contexts to allow for disempowering of stressors. A causality analysis to help a user find correlations between events and moods, can be used to help reverse or cut the causation cycle by introducing delays or changing presentation, or to enhance other relationships to emphasize certain moods or behaviors (e.g. the phone or email that disappears when the user obsessively looks at it).

The wearable computing device may measure EOG and eye blink properties in order to determine the user's emotional recovery response to natural events. The natural event may be inferred by blink and lag time may be measured post-event. The time lag may be recorded and used as an input into cognitive and emotional state classifiers. Eye blinks may be used as a way of measuring workload as blinks happen when a user's stimulus is less salient. Squinting may reflect discomfort, stress, anger, or doubt. Any of the above may be used to train the wearable computing device to recognize EEG-based emotions in the user. Facial expressions, including micro expressions, may also be detected by the wearable computing device to help annotate the current happenings. For example, an insincere smile, contraction of the zygomatic major alone, sincere duchenne smile, or zygomatic major together with the orbicularis oculi may be measured and equated to an emotional response. Similarly, happiness, sadness, surprise, fear, anger, disgust, or contempt facial expressions may also be determined and equated to an emotional response. A "kiss" expression may also be detected on the face of the user. Where the user is in communication with another user through the wearable computing device, where a "kiss" expression is observed, a "kiss" indication or emoticon may be displayed to the other user on that user's respective wearable computing device display.

Figure 15:
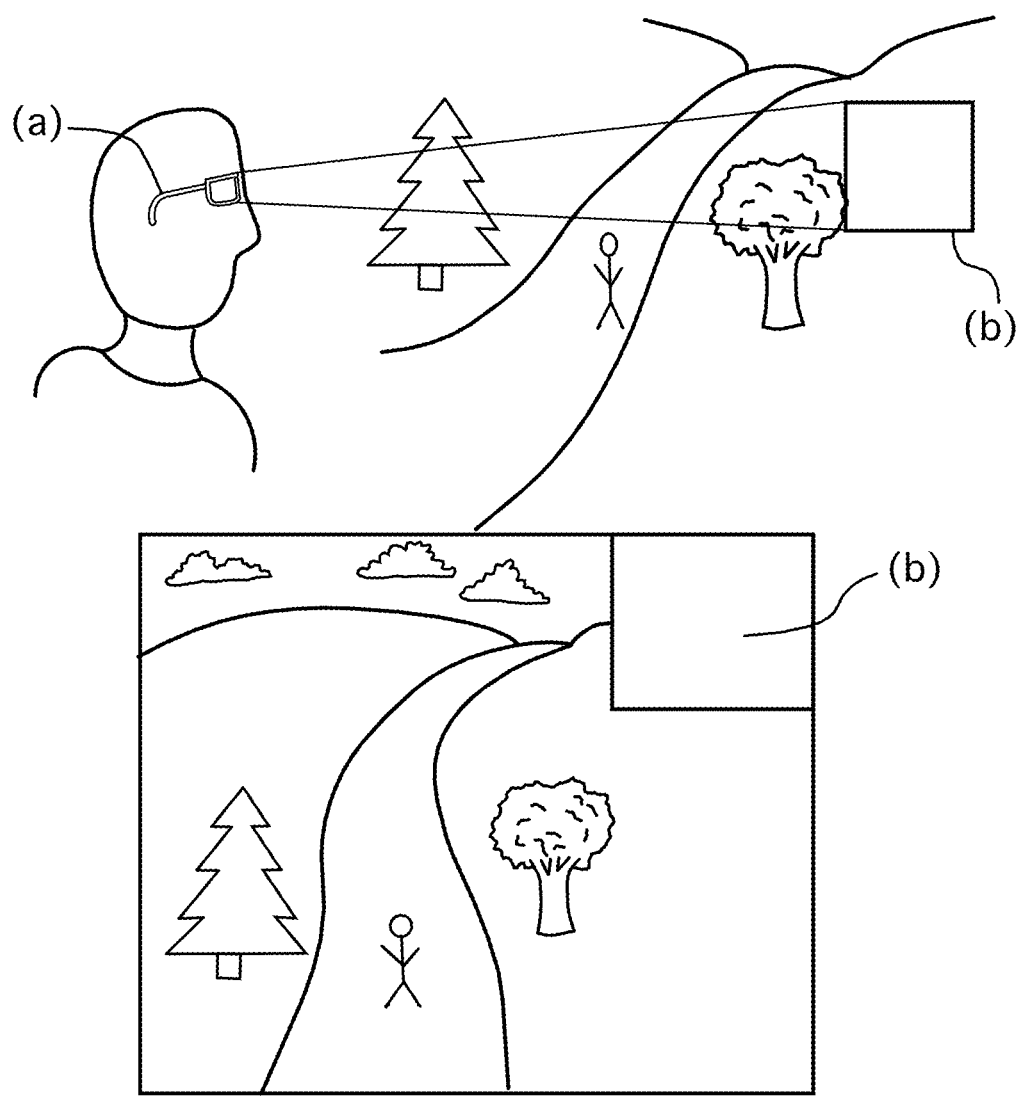
FIG. 15 illustrates a possible implementation of the present invention in use.

FIG. 15 shows a user in an environment wearing an implementation of the wearable computing device, reference (a), in glasses form. Reference (b) depicts where in the user's field of view, the display from the wearable computing device may be seen.

Figure 16:
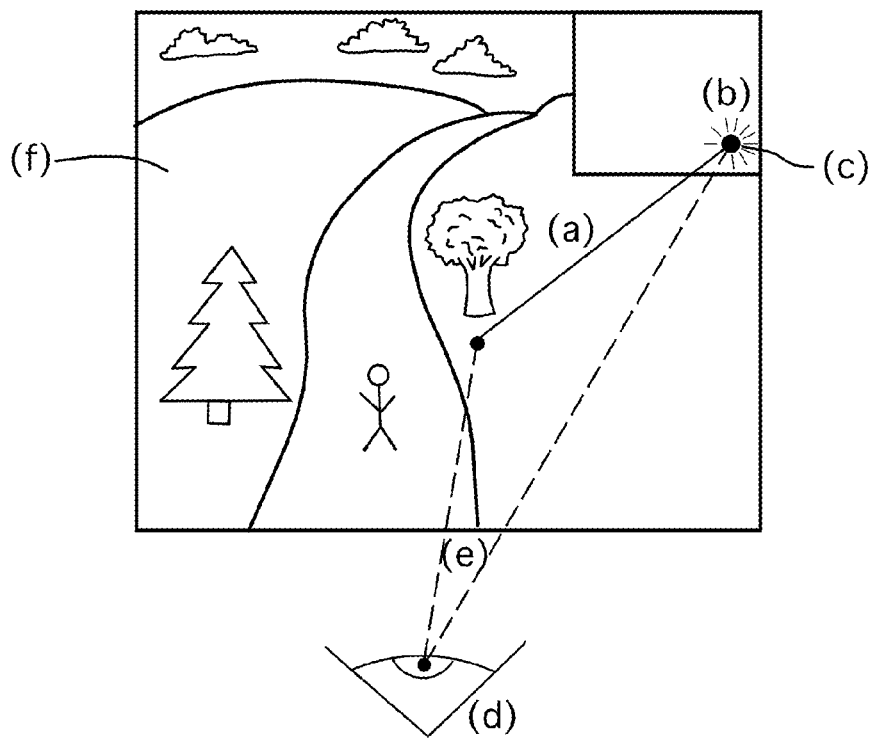
FIGS. 16 to 34, and 35A to 35B illustrate a selection of monitored user interactions and displayed interface elements, of at least one other possible implementation of the present invention.

FIGS. 16 to 34 and 35A to 35B show a selection of monitored user interactions and displayed interface elements of one or more possible implementations of the wearable computing device of the present invention. FIG. 16 shows the user's field of view (f) as seen from the user's eye (d) in a particular gaze direction (e). Reference (c) represents an indicator displayed on the display of the wearable computing device. The dotted lines represent directions in which the user's eye is looking. Reference (a) represents saccadic eye movement between points of fixation at the tree in the middle of the field of view, and at reference point (b).

Figure 17:
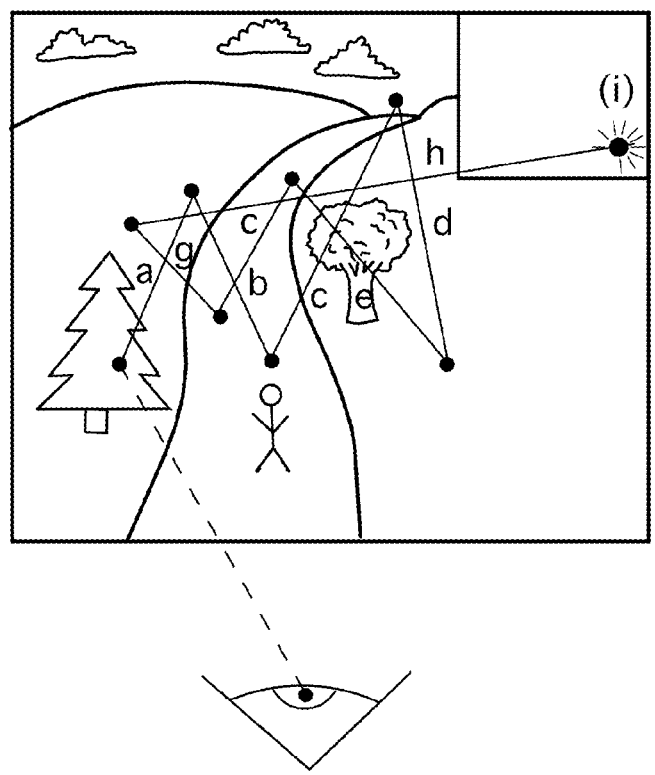

FIG. 17 shows the user's field of view and examples of saccadic eye movement (a) through (g) as the user's eye scans through the field of view. In an implementation, EOG sensors in the wearable computing device, possibly combined with input from video-based eye-tracking, may detect eye movement using the changes in measured electrical potential. When movement (h) is detected, such that the user's gaze is directed at interface (i), the wearable computing device may reduce the amount of time that the user must fixate on the interface at (i) in order for the interface to activate. If eye movement (h) is not detected and the wearable computing device determines that the user is fixated at a particular point for a prolonged period of time, not necessarily at point (i), the interface may activate.

Figure 18:
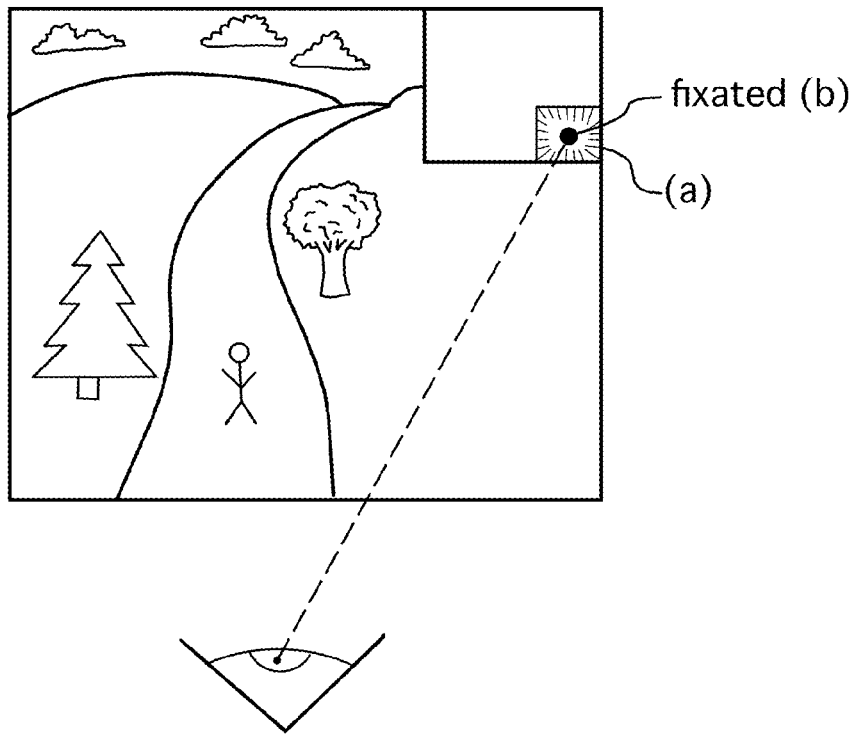

FIG. 18 shows user eye fixation on the interface (b) of the display of the wearable computing device. The wearable computing device may determine that the user is looking at the interface by measuring a lack of EOG signals over a prolonged period of time, indicating that the user's eye fixation is being held steady. Optionally, the user may fixate on an indicator in the display that is flashing, at reference (a). This state of the user may be measured in ERP or SSVEP events detected in the user's brainwaves by the wearable computing device's EEG sensors.

Figure 19:
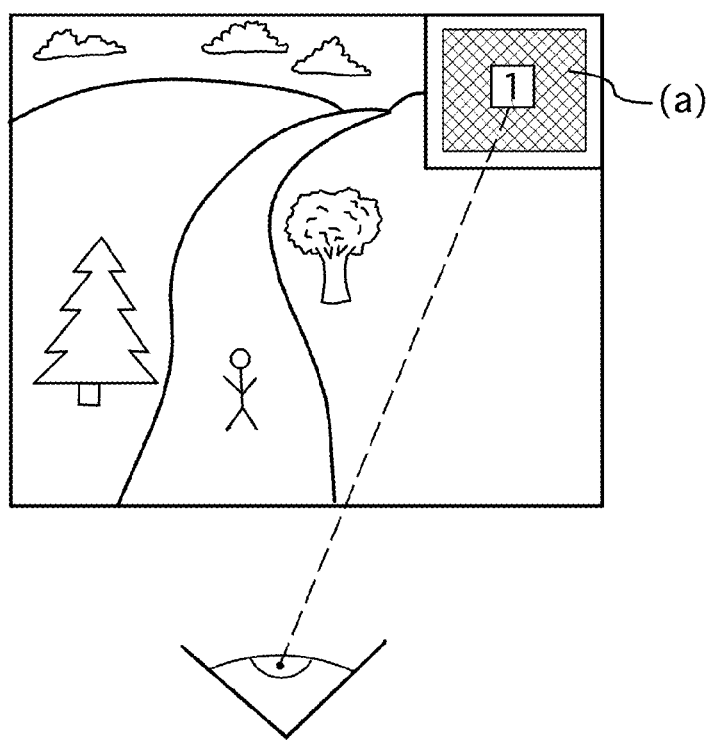

FIG. 19 shows the user looking at the display of the wearable computing device. The device may detect that the user is attending to the interface, or is waiting for the interface to respond and the device may cause an application interface to be displayed on the display.

Figure 20:
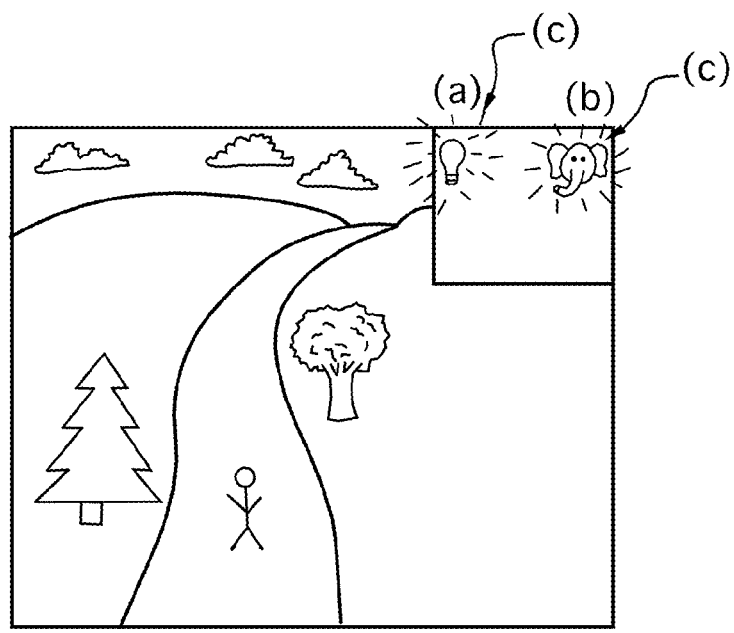

FIG. 20 shows examples of various icons that may appear on the display of the wearable computing device such that activating either icon by any of the means previously described would cause the wearable computing device to activate particular functionality. For example, indicators (a) and (b) are shown respectively corresponding to a light bulb representing the "inspire me" method, and an elephant indicator used to select the "memory jog" method. The selection may be made through continued focus on the indicator of choice using eye tracking or through the utilization of indicator flashing (c) where each indicator flashes at a different rate and a correlated signal (such as visual ERP or SSVEP) is measured in the user's brainwaves. Optionally, a combination of the two methods may also be used to improve performance. The "memory jog" method may comprise a set of flipbook-like interactions to attempt to help stimulate the mind of the user and attempt to aid the user in locating visual information that the user would like to see, drawing primarily from things the user has seen before. In comparison, "inspire me" and search methods may draw more things the user has not seen from a variety of sources, such as from Internet. The inspiration method or application may retrieve and display images from the Internet mixed with images from the user's personal library accessible to the wearable computing device. The recall or "memory job" method or application may retrieve and display older images from the user's library in addition to the most recent items that the interface has presented to the user such as text messages or other image content. Activating the "memory jog" or "inspire me" application or method may be done through user hand gesture, physically operated selectors or virtual selectors that the user may interact with using detected eye movements or eye gaze fixation. In the latter case, selection may be made by the method described above or through using indicators in the display that the user focuses on to select.

Figure 21:
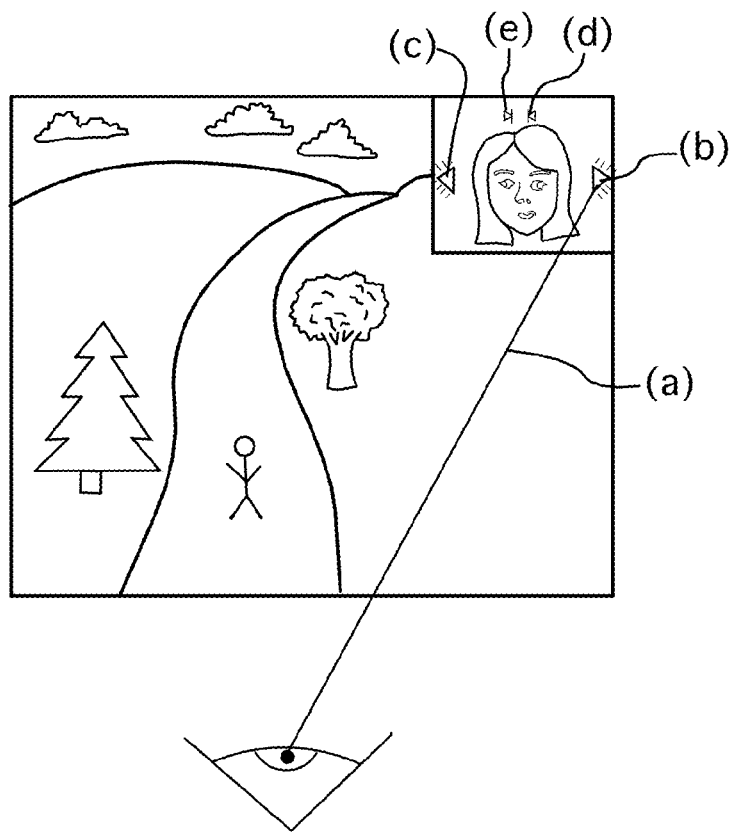

FIG. 21 shows an exemplary view of the display of the wearable computing device once the memory jog function is activated. A first image may appear on the interface. The user may fixate on arrows to the right or left of the image to change the direction (in time or order in an album) in which the images are changed or flipped-through. For example, if the images are organized and displayed by time of creation, time of viewing, or any other time data, then the user focusing on the left arrow (c) may cause the image to be changed such that each successive image displayed was created or acquired at an earlier time than the previously displayed image. If the user focuses on the right arrow (b), the order may reverse. Focusing on arrows may only change display ordering and may not be required to advance the images. The user's level of interest, measured by any of the methods described previously, may control how slowly or quickly the interface flips through pictures in that section of the timeline or album. The time scale between subsequently displayed pictures may be indicated with UI elements (d) and (e) where in this example the distance between the indicators (d) and (e) shows the scale. Where the elements (d) and (e) are further apart or closer together, different time scales may be indicated. Other ways of indicating this information may also be used such as embellishing the left and right arrow to indicate the size of time jump between pictures.

Figure 22:
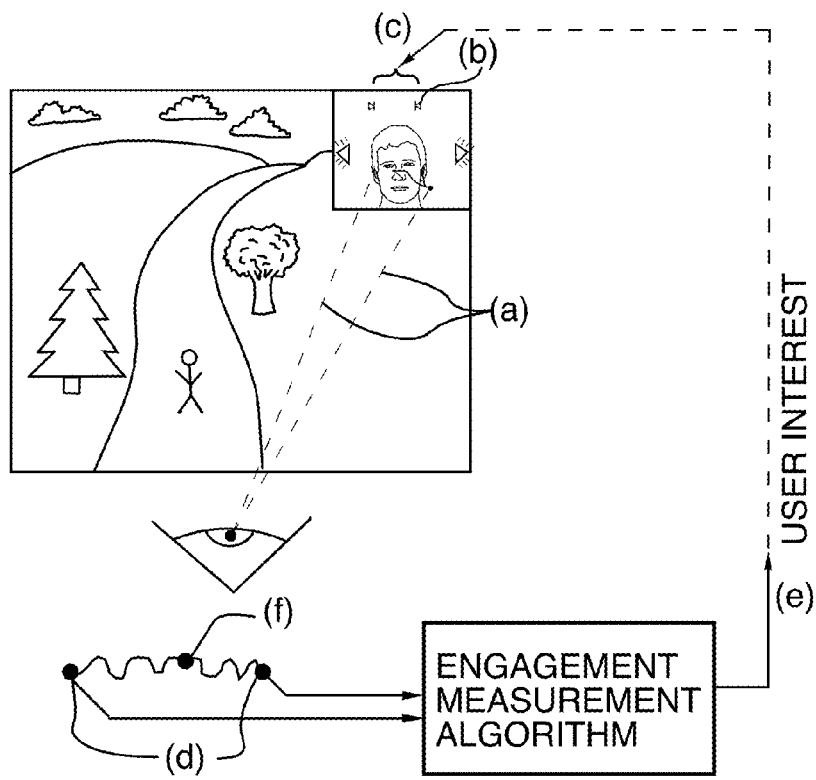

FIG. 22 shows another image in the memory jog sequence that may appear as the user continues to look at the interface. The sequence jump size (time scale) has been increased as compared to FIG. 21 since the user's brain state has been measured to be less engaged. This user interest measure (e) has been produced by bio-signal sensors (d) connected to the wearable computing device measuring the user's brainwaves (f) and corresponding algorithm, previously described. Low interest (e) may increase the jump size (shown by indicators (b) and (c)) between album entries in order to attempt to show the user images in the sequence closer to those useful to jog the user's memory. While the user is observing the images, the user may attend to different points on the interface (a). Image advancement direction will remain in the active forward or backwards direction until the user once again focuses on one of the arrows indicating that the user wishes for the presentation direction to change.

Figure 23:
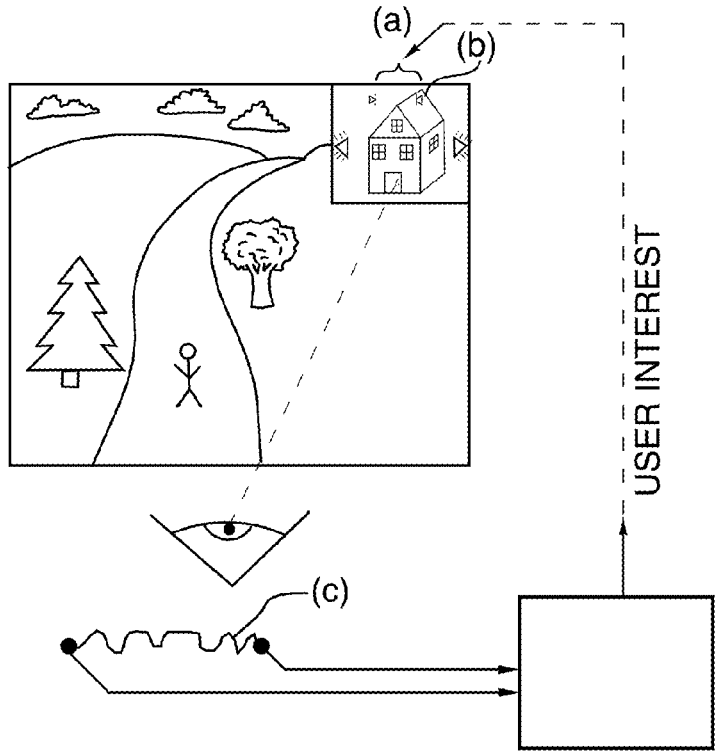

FIG. 23 shows another image in the sequence being displayed in the display of the wearable computing device. In this example, the user is more engaged as interpreted from the user's measured brainwaves (c). The wearable computing device alters the display of images so that the next image occurs at a closer proximity in time. This change is shown by the indicators (a) and (b).

Figure 24:
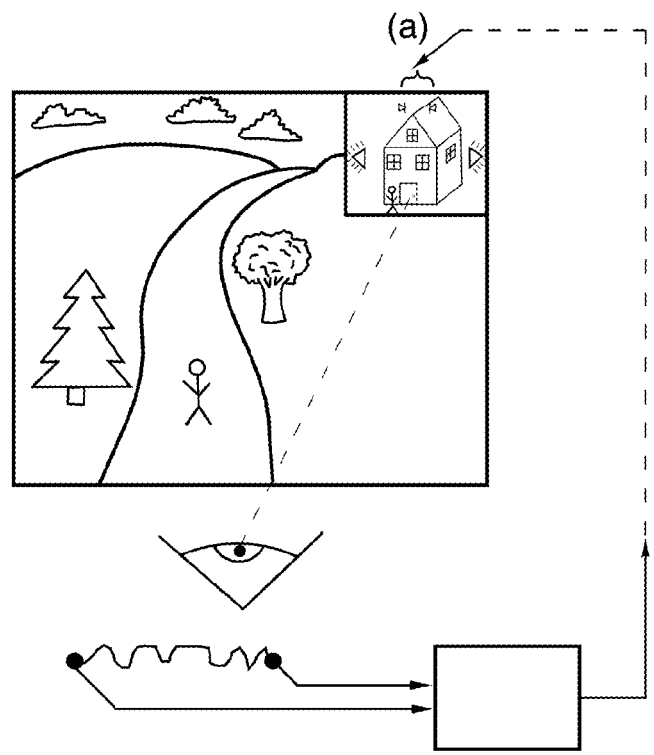
Figure 25:
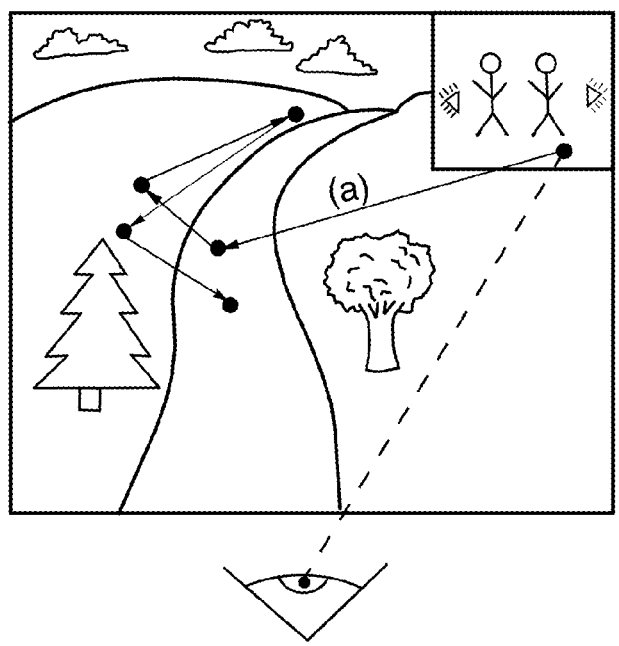
Figure 26:
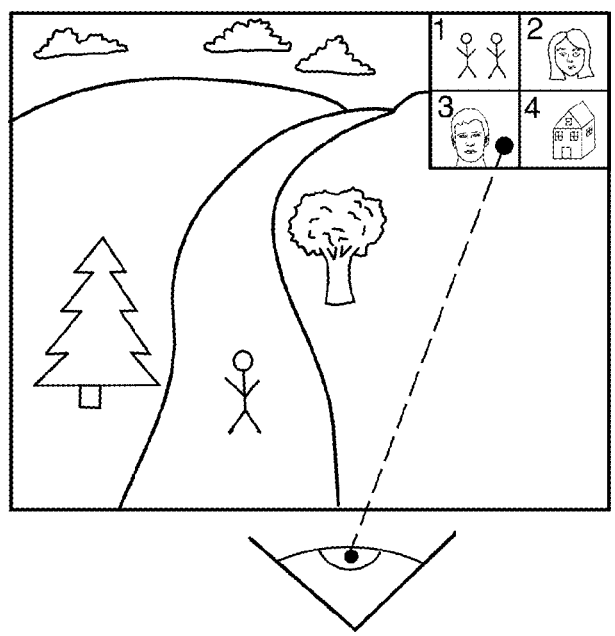

FIG. 24 shows another image in the sequence being displayed in the display of the wearable computing device. In this example, the user is measured to be even more engaged than in the example of FIG. 23, and the image sequence reflects this by causing an image to appear that was taken at nearly the same time as the previous image. The time scale indicators (a) reflect this change in time scale. The wearable computing device may continue to display images until the user looks away from the display, as shown in FIG. 25. In this case detection of (a) followed by a period of the user not attending to the interface will cause the images to stop advancing. The wearable computing device may then cease updating the display, fade out the display, go quiet, or turn off the display to allow the user to attend to the environment. Alternatively, the wearable computing device may then show a summary of the images that had the highest measured user interest levels during the image sequence displayed, as shown in FIG. 26.

Figure 27:
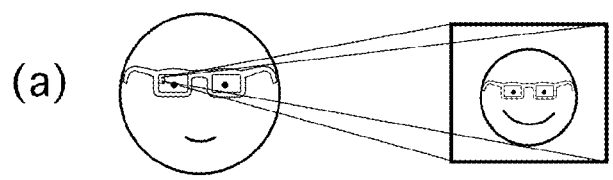
Figure 27:
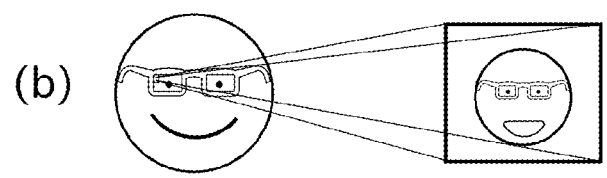
Figure 27:
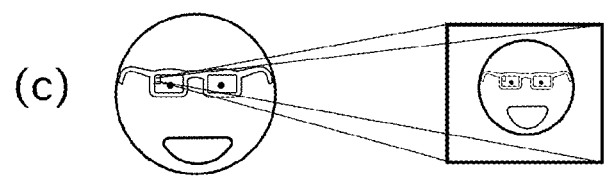
Figure 37A:
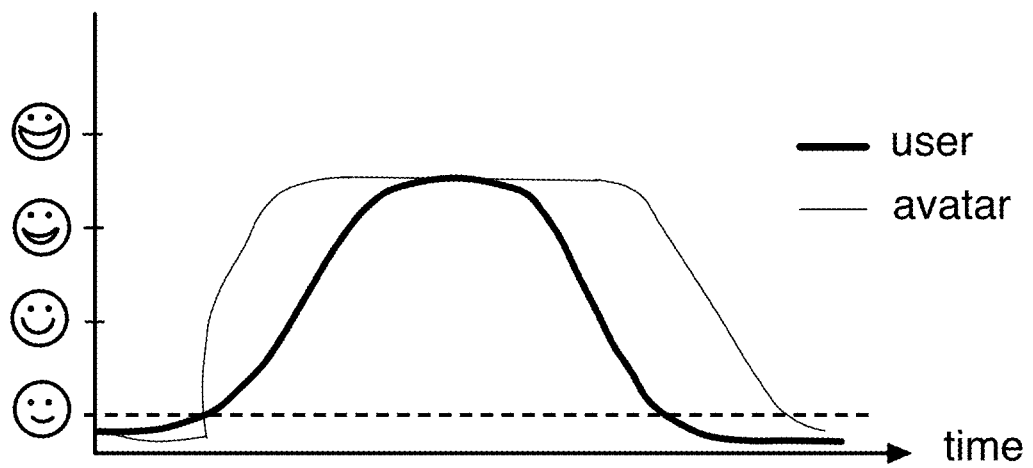
Figure 37B:
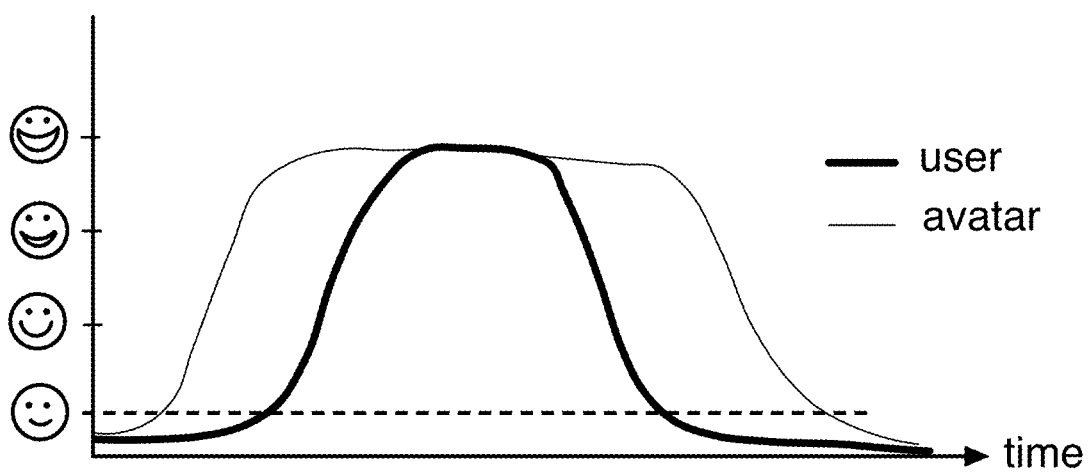
Figure 38:
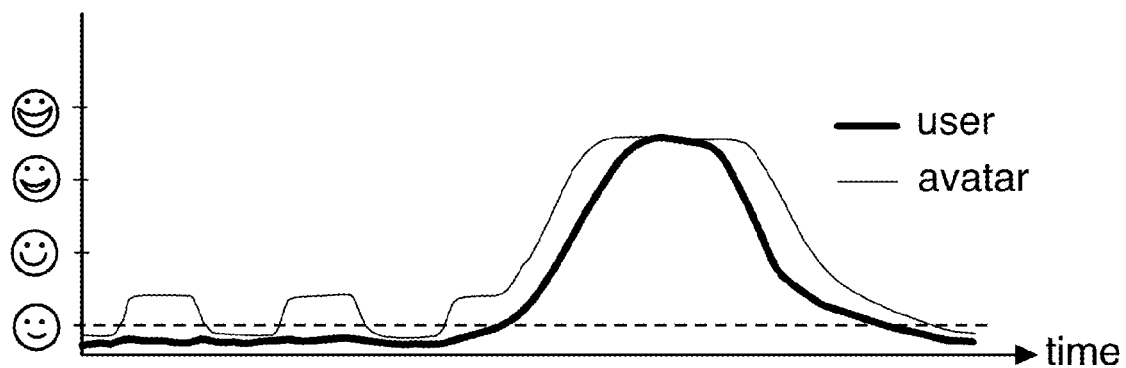
Figure 39:
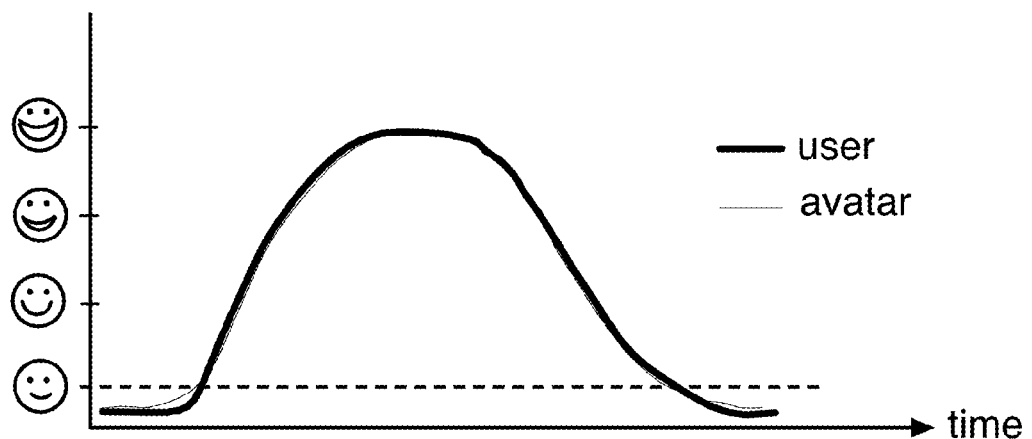
Figure 40A:
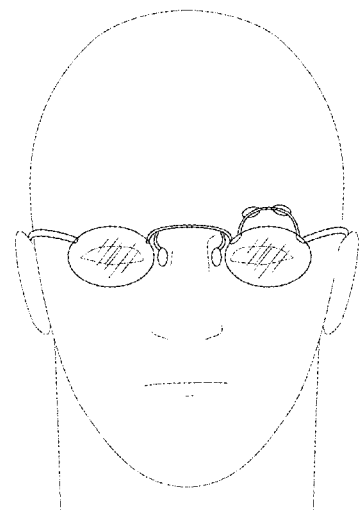
FIGS. 40A to 40C illustrate front elevation, side elevation, and perspective views, respectively, of another possible implementation of the invention.
Figure 40B:
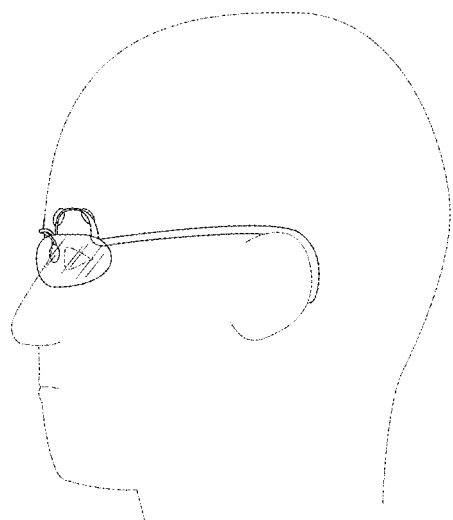
Figure 40C:
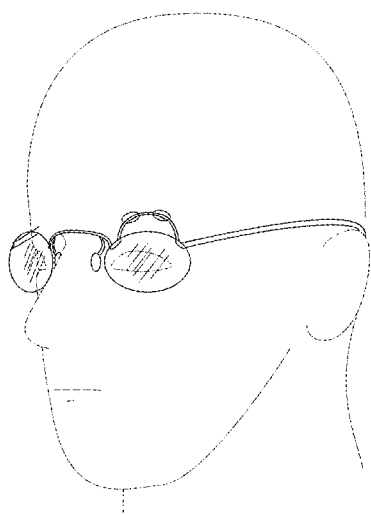
Figure 41A:
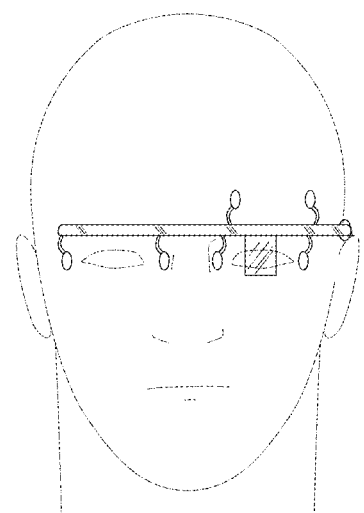
FIGS. 41A to 41C illustrate front elevation, side elevation, and perspective views, respectively, of another possible implementation of the invention.
Figure 41B:
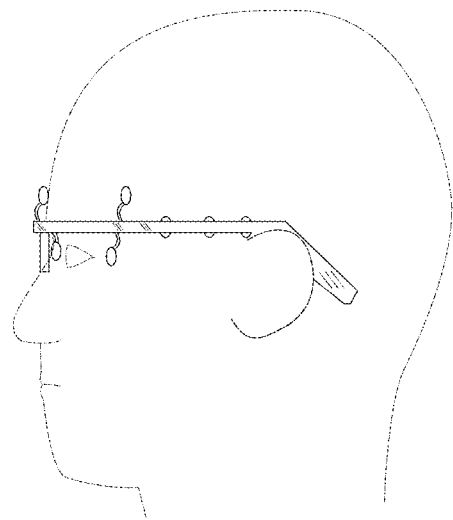
Figure 41C:
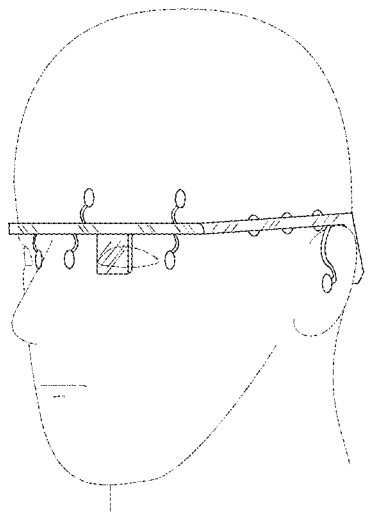
Figure 42A:
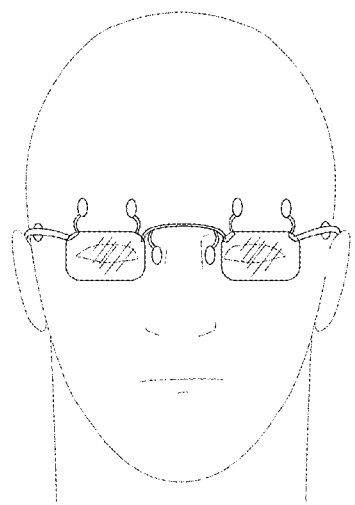
FIGS. 42A to 42C illustrate front elevation, side elevation, and perspective views, respectively, of another possible implementation of the invention.
Figure 42B:
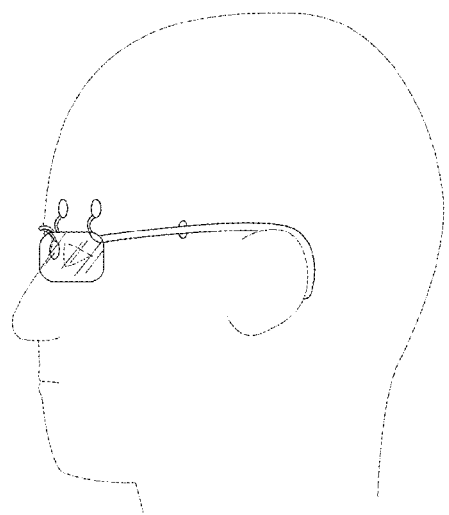
Figure 42C:
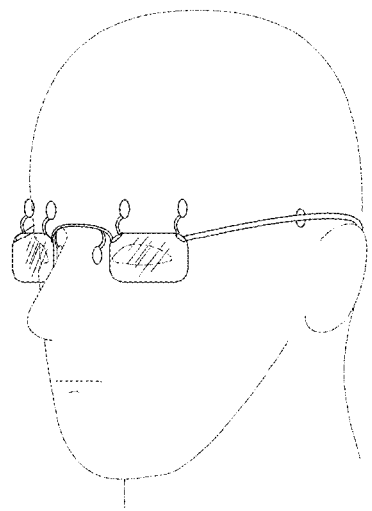
Figure 43A:
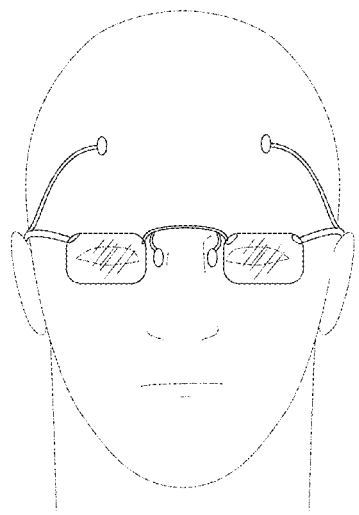
FIGS. 43A to 43C illustrate front elevation, side elevation, and perspective views, respectively, of another possible implementation of the invention.
Figure 43B:
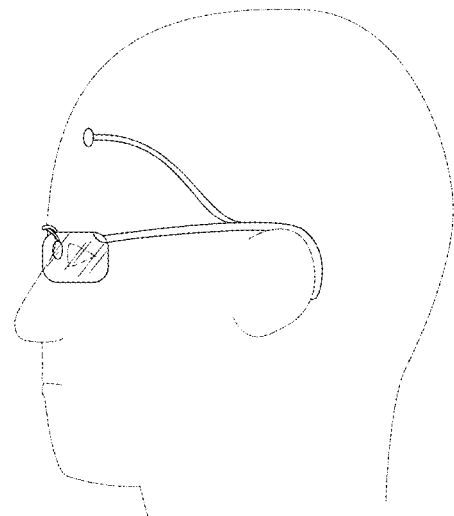
Figure 43C:
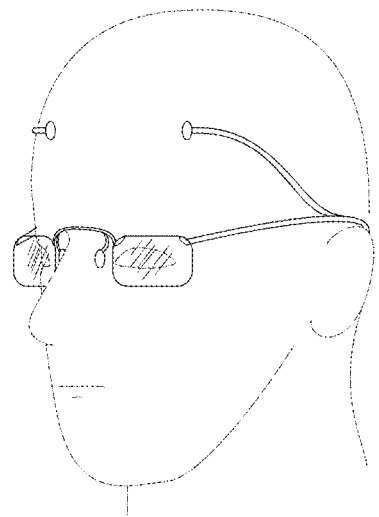
Figure 44A:
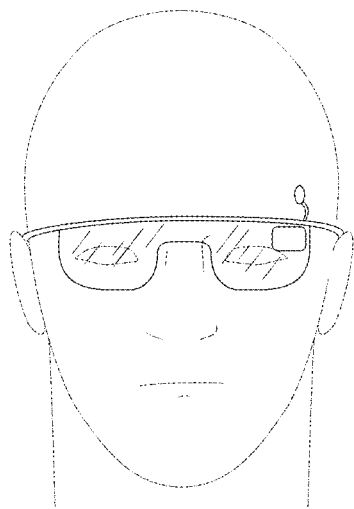
FIGS. 44A to 44C illustrate front elevation, side elevation, and perspective views, respectively, of another possible implementation of the invention.
Figure 44B:
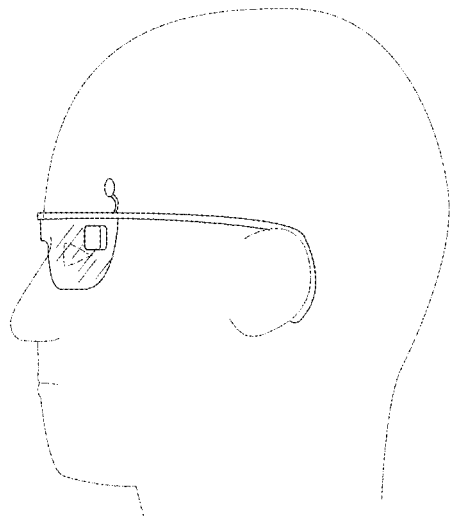
Figure 44C:
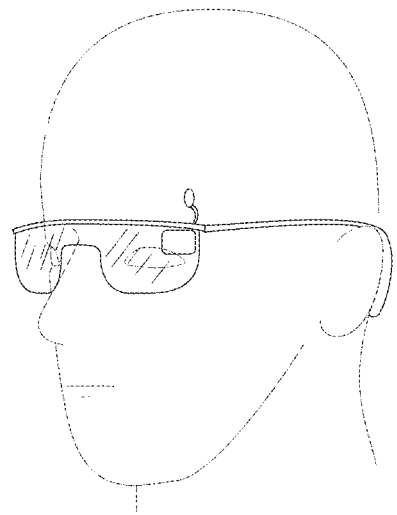
Figure 45A:
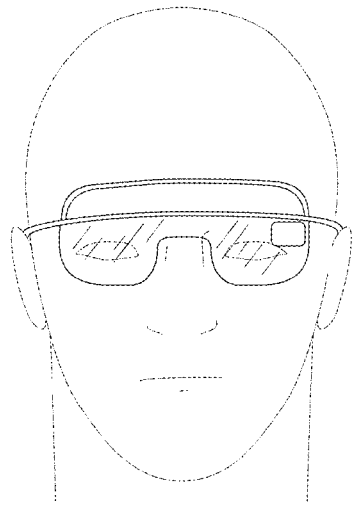
FIGS. 45A to 45C illustrate front elevation, side elevation, and perspective views, respectively, of another possible implementation of the invention.
Figure 45B:
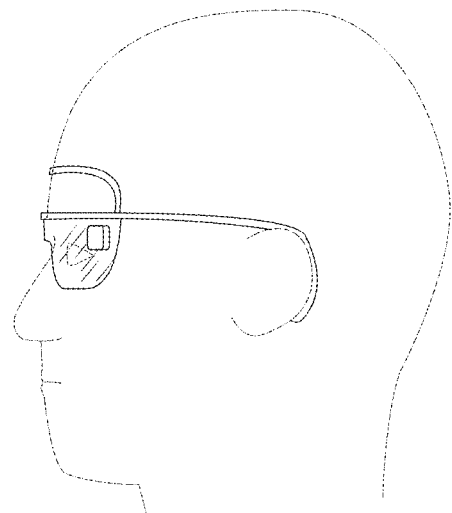
Figure 45C:
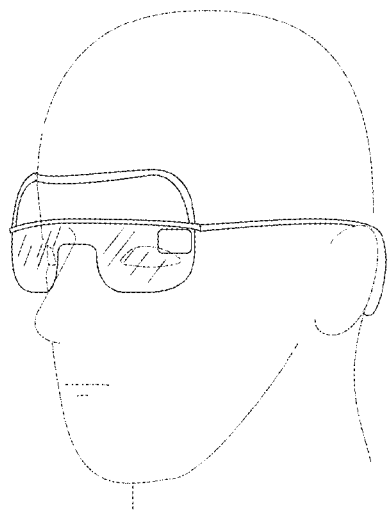

FIG. 27 shows an exemplary application or method of the wearable computing device, referred to as the "smile widener". This method may be used to encourage a user to smile and thus improve the user's mood. This method may include, at (a), the device measuring the user's degree of smile, the device causing an avatar shown on the display to smile wider than the user. At (b), the user may see a smile on the display that is wider than the user's own smile. The user's mirror neurons may register the wider smile and the user may attempt to try to match that smile, causing the user to smile wider. The interface may then display the avatar smiling even wider still. At (c), this process may continue as the user keeps trying to reflect the smile of the avatar until the user is smiling at or near maximum smile wideness for the user. FIGS. 36A to 36B, 37A to 37B, and 38 to 39 show various exemplary avatar smile intensities in response to particular measured user smile intensities, where the black line indicates the user's smile intensity over time, and the red line indicates the avatar's smile intensity over time in response. In "version 1" shown in FIG. 36A, the user begins to smile. As soon as the smile reaches a predetermined threshold, marked as reference (1), the wearable computing device may be configured to display an avatar that begins to smile or update an avatar already appearing on the display. The avatar's smile may be adjusted to always be slightly broader than the user's smile. At reference (2), the user imitates the avatar's smile until the maximum smile is reached at (3). As the user's smile decreases thereafter at (4), so does the avatar's smile but with a delay to prolong the user's smile. In "version 2", shown in FIG. 36B, the avatar begins smiling in advance of measuring a user smile. FIGS. 37A and 37B shows alternate response curves when compared to the graphs of FIGS. 36A and 36B, where the user is shown as taking longer to react to changes in the avatar's smile intensity. FIG. 38 shows further exemplary response curves where the wearable computing device is configured to attempt to illicit smiles from the user using changes in avatar smile intensity multiple times, before succeeding. Accordingly, the wearable computing device may be configured to cease attempting to encourage the user to smile when no user smile is measured for a predetermined period. Optionally, the wearable computing device may be configured to attempt to encourage the user to smile multiple times where no smile is measured for a predetermined time. FIG. 39 shows an exemplary response curve where the wearable computing device is configured to not employ any smile widening encouragement. Here, it can be seen that the avatar's smile intensity is adjusted to substantially align with the user's smile intensity as the user smiles at the user's own pace. This avatar response may be used for some fraction of the time to get the user accustomed to the avatar depicting the user's current facial state. Other avatar feedback expression methods similar to "smile widener" may be employed by the wearable computing device in order to encourage the user to change facial expression type or intensity in a variety of ways.

Figure 28:
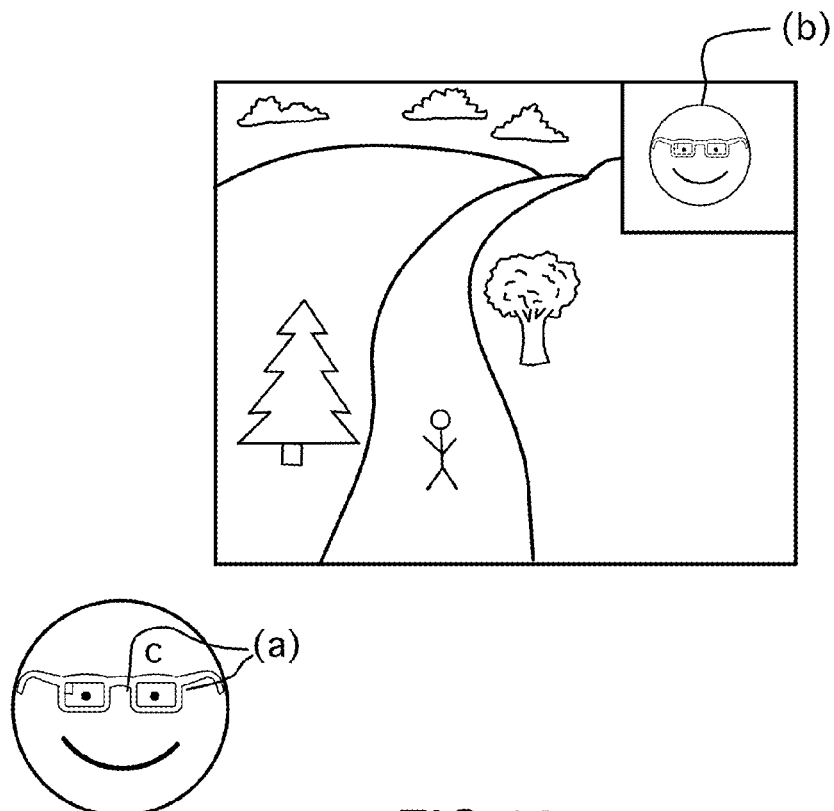

FIG. 28 shows the user's avatar (b) appearing on the display interface. In an exemplary implementation of the wearable computing device, this avatar may reflect the user's current facial expression or emotional state. The user's expression may be determined using electrical bio-signal sensors (a) that measure activation of the user's facial muscles. The avatar may be a simplified representation of the user or a more accurate or life-like representation.

Figure 29:
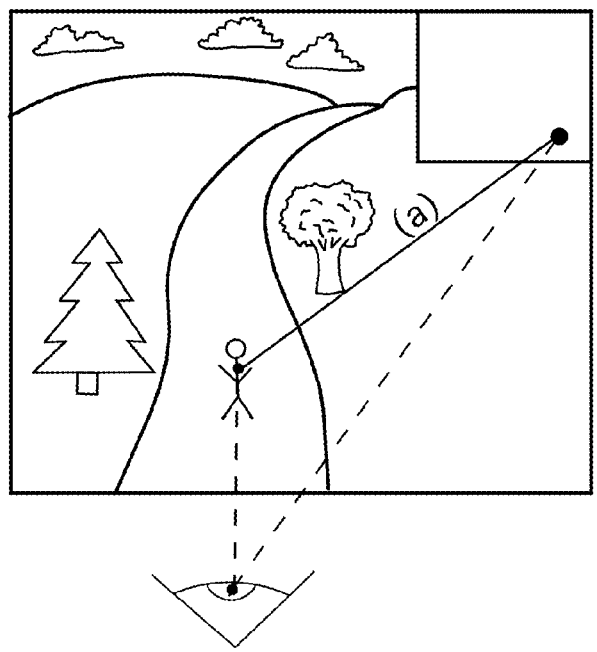
Figure 30:
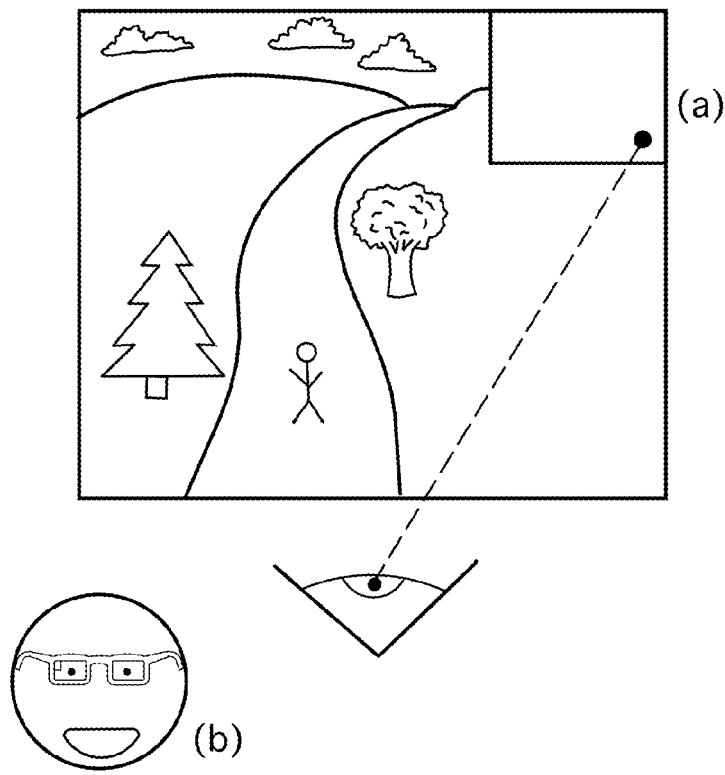
Figure 31:
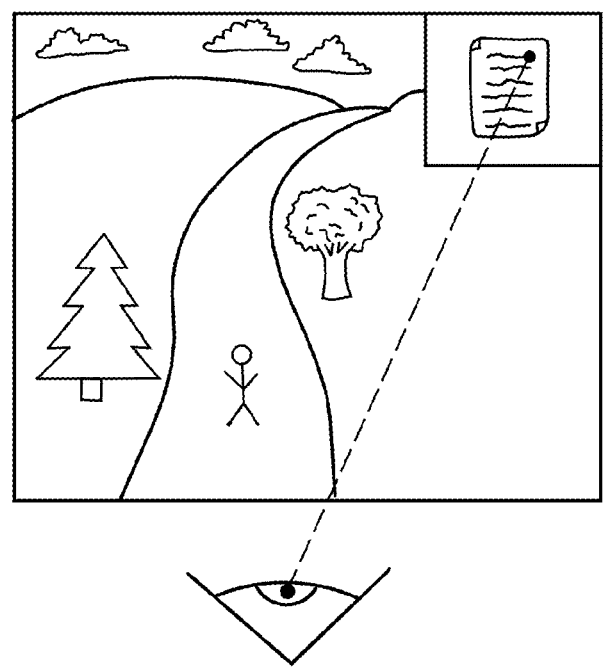
Figure 32:
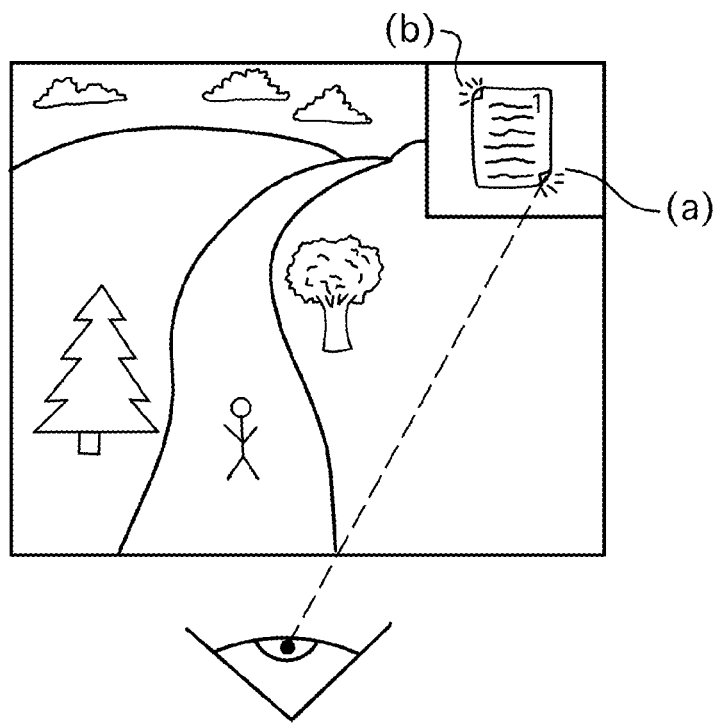
Figure 33:
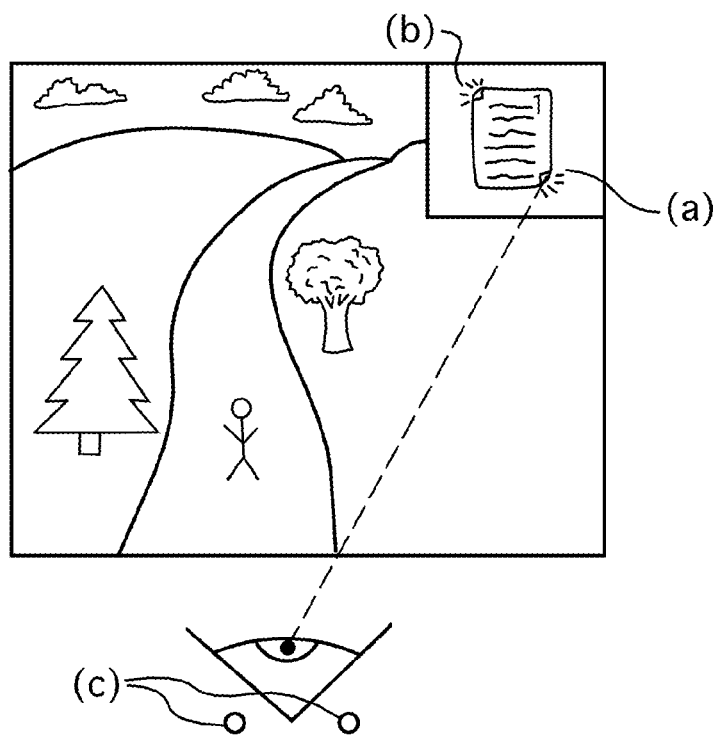
Figure 34:
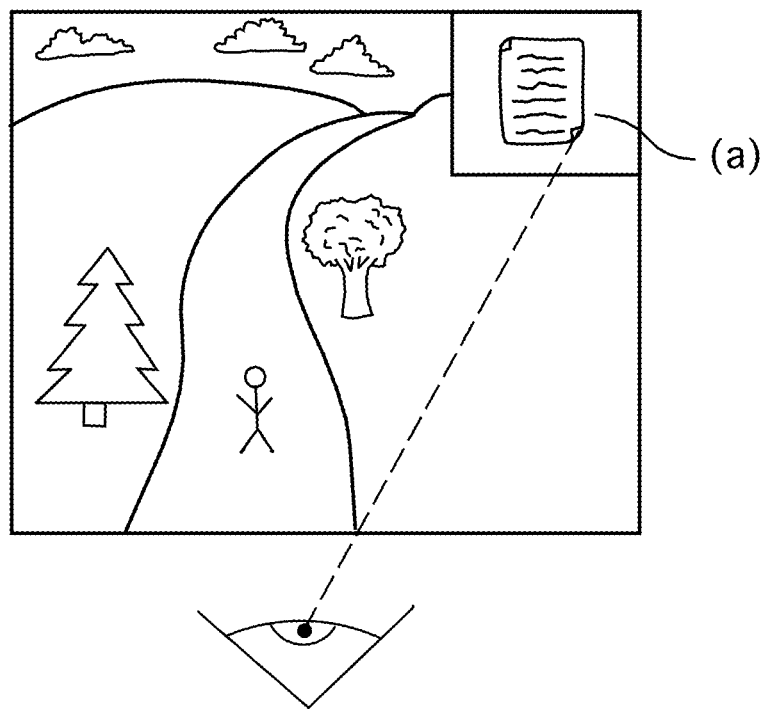

FIG. 29 shows an exemplary implementation of the wearable computing device where the user's focus is shifted by saccadic movement (a) from a point in space to being fixated on the interface. Next, as shown in FIG. 30, the wearable computing device may wait until a smile is detected on the user while the user is fixated on the interface. The wearable computing device may change what is displayed on the display in response. For example, the device may display a message upon measuring the user's smile. Messages "delivered with a smile" may be messages that are delivered to the user only when the user is smiling, either while looking at the display or elsewhere. Other similar methods may be used with other facial expressions such as "turn a frown upside down" messages that are delivered to users only when the user frowns, or when the user is attending to the interface and frowning. A friend or contact of the user optionally registered with the wearable computing device may deliver a message to the wearable computing device for display or delivery to the user only during particular modes of delivery, e.g. when the user is smiling, frowning, or emoting in any other predetermined fashion. In this way, the user's contact may attempt to cheer up the user with a personalized message when the wearable computing device determines that the user may be in need of cheering-up.

FIGS. 31 to 34 show exemplary non-limiting implementations of the wearable computing device of the present invention implementing a method (optionally referred to as "flicker flipper") for advancing through messages, multi-page documents, images, or other content on the display of the wearable computing device, without requiring the user to make any gestures other than with the user's eyes. For simplicity an example of reading a book on the display of the wearable computing device is used, but the same method can be used for sequencing though other information. At FIG. 31, the user is reading a book on the display interface. Here, forward and backward indicators are present, optionally shown at the top left and bottom right corners of the page that appears turned up. At FIG. 32, once the user stops reading and fixates on one spot of the display, the corners of the page may start blinking at different speeds to facilitate the use of visual ERP or SSVEP methods of determining selective user attention. At FIG. 33, the user fixates on one of the blinking corners and the blinking speed is registered in the user's brain. The wearable computing device measures the brain for this registered blinking speed and may cause the page of the book to turn to the page in accordance with the blinking corner having the registered blinking speed. At FIG. 34, once the page has been flipped, and the user is no longer attending to the indicator, the blinking subsides so that there is less visual distraction to the user.

Figure 35A:
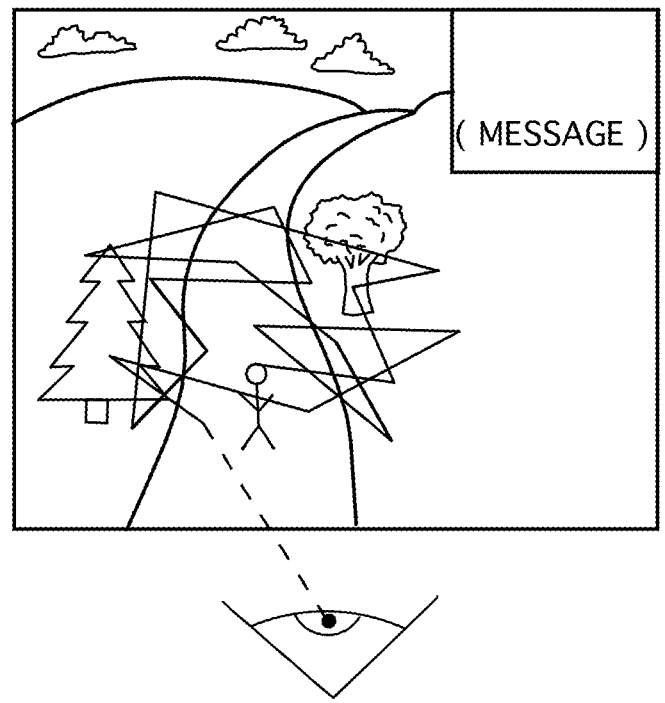
Figure 35B:
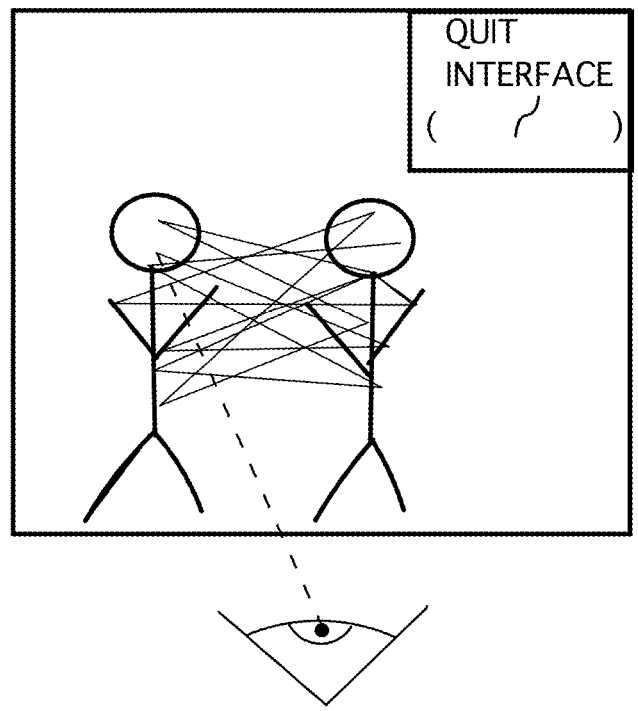
Figure 36A:
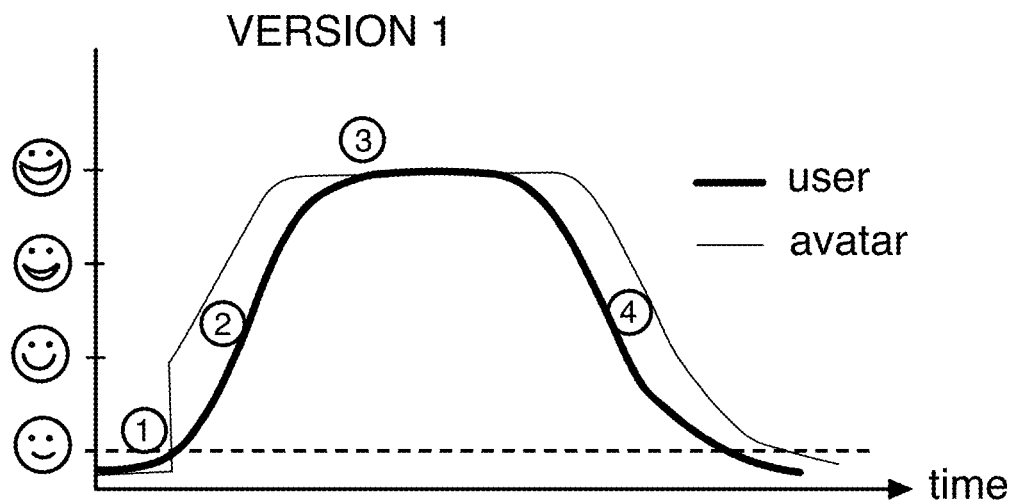
FIGS. 36A to 36B, 37A to 37B, and 38 to 39 illustrate graphs showing possible response values by possible implementations of the present invention with respect to possible measured input values.
Figure 36B:
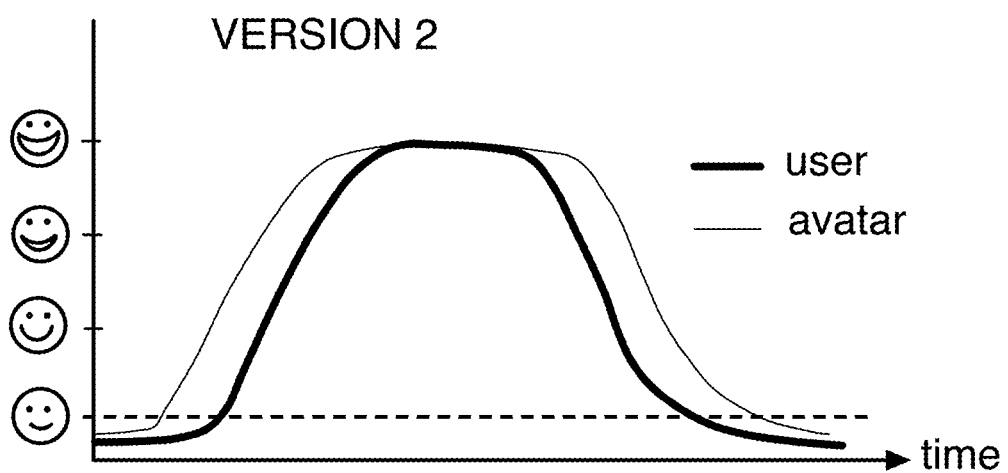

FIGS. 35A and 35B show an exemplary non-limiting implementation of the wearable computing device of the present invention implementing a method to determine X based on saccadic eye movement and the user's context within the environment. At the environment shown in FIG. 35A, the user scans a scene without any particular intention. The user's point of focus flits from one place to the next without any apparent pattern or structure. In this case the user is not very focused on what the user is seeing, and the user is likely to be in a good state to receive messages from the interface since the user is likely able to attend to it without being distracted from a task in which the user is engaged. In FIG. 35B, the user follows a conversation between two people. The user's point of focus flits from one point to the next and has apparent structure as the user is repeatedly looking between the two people, and not at seemingly random points all throughout the environment. The structure of the eye movements may indicate to the wearable computing device that the user is involved in what the user is seeing and may be significantly disrupted by having messages appear in the display of the wearable computing device at that time. The interface thus may remain quiet so as not to disturb the user. Eye movements may be determined by the wearable computing device using EOG measurements from corresponding bio-signal sensors of the device, since high accuracy is not required, but rather just apparent structure to the movements.

Application: Communication and Compatibility: Finding Love in Real Life (A.1)

The wearable computing device may use visual data, combined with sensory input, to gauge an "attractiveness factor" between a user and another individual. In particular, brainwave and heart rate sensors may be used to attempt to assist the user in finding or making a connection with another person based on the gauged attractiveness factor.

Figure 46:
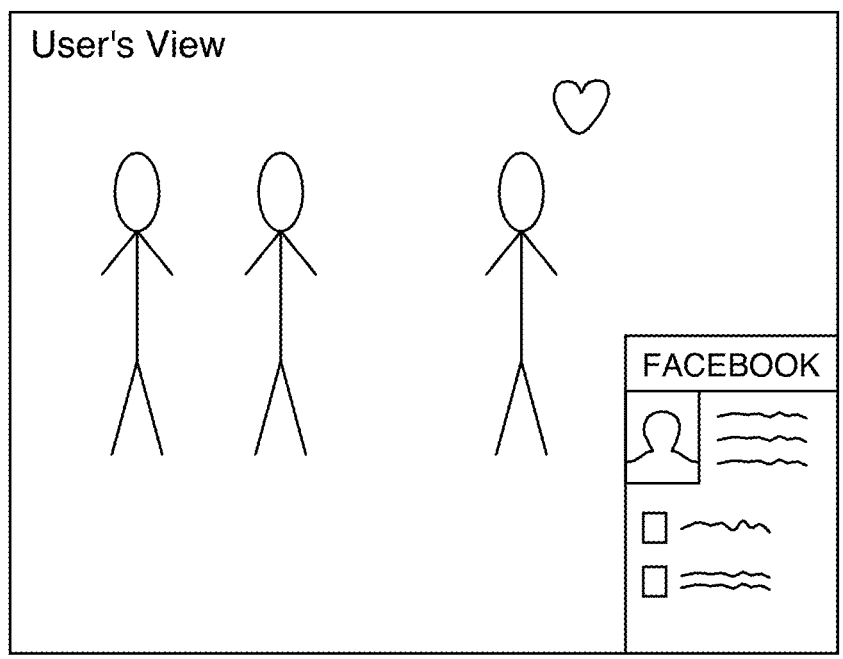
FIG. 46 illustrates a view in a display of the wearable computing device in accordance with an exemplary embodiment of the present invention.

To illustrate this application, the following example is provided, with reference to FIG. 46. In this example, a user, "Dan", is walking through a crowded train station. He scans the crowd waiting for trains, looking at the faces of his fellow passengers whilst wearing the wearable computing device of the present invention. A video-camera mounted on the wearable computing device is oriented in the same direction as the user's gaze (e.g. the video camera is aimed at the same field of view as the user is actually seeing through his eyes). This may be based on a vector perpendicular to the plane of an "eye-glass" portion of the wearable computing device. In addition, eye trackers may be used to fine tune the angle of the viewing camera from the vector perpendicular to the eyewear. The video camera vector of sight is adjusted to match the horizontal angle (theta) and the vertical angle alpha of the user's eye gaze.

After several minutes of scanning, Dan sees someone who he thinks is attractive. The attraction causes an increase in heart rate which is recognized by his heart-rate monitor. In a different example, the user's brainwaves are analyzed to determine that the brain state of the user is one of attraction towards another human being. Also, multiple sensors such as heart rate and predicted brain state may be combined to indicate that the user finds another attractive. The wearable computing device is constantly monitoring the user's field of view. When the algorithm pipeline determines that the user finds another attractive, the field of view being recorded by the wearable computing device's video camera is tagged with this information, or, optionally, the device display view may become tinted a particular color, such as rose-colored.

Accordingly, in at least one aspect, the wearable computing device may be configured to receive input from the wearer user indicating at least one object viewable in the wearer's field of view. The input may be received by a variety of means, including, but not limited to: the device cycling between various objects detected in the scene until the user selects one of the objects by speaking, eye movement, pressing a button on the device, or by any other input means; tracking the user's eye movement or eye focal point/area in the field of view using at least one eye-tracking sensor of the wearable computing device; or the device taking a picture of the field of view for the user to subsequently look at in order to identify the object being looked at in the eye focal area (e.g. the person that the user is looking at and attracted to). Other means of receiving input from the user indicating the person being looked are possible.

A still video of section of video is sent to the Cloud or sent locally on a computer the user is wearing or sent to the wearable computing device. Features from the face of the person that the user finds attractive are extracted from a still image. These features can include eye colour, distance from the centre of one eye to another etc. Using these features a search for a matching person is initiated through a database that resides in the Cloud such as social media (e.g. Facebook). Each person the user is looking at is subjected to a facial recognition scan. The data regarding who he is attracted to is stored locally on his device or sent to the cloud for later retrieval. Brainwaves corresponding to his heightened level of interest may also be detected. This input may also be sent to the cloud. In response to these sensory inputs, the wearable computing device hardware or software is instructed to run a facial recognition program on the "target's" face. This program can be stored on the cloud and executed when a request from the device is sent.

If the recognition search for the target of Dan's attraction is successful, Dan will see data from a third party (i.e. Facebook) overlaid on his "target's" image as shown in FIG. 46. The Information that the target is willing to share is presented overlaid in the viewing screen. The wearable computing device will also enquire if Dan wants to take a picture of the object of his affection to save for viewing later. If the "target" has a similar response to looking at Dan, a notification can be sent to each of their devices via the Internet signaling their mutual attraction.

A third party website notes that the user has found the target interesting. So a record in the third party web site notes the time and location and the target id of the target of interest. In addition, the target of interest may also be using a wearable computing device of the present invention. If she finds the user attractive then the same information is sent to Facebook with her ID and the ID of the user that was predicted from face recognition. A message is sent to both users that there is mutual attraction. They are asked if they want to share their contact information for follow up communication that notes the place and time that they saw each other.

Using the internet to find romantic partners is a hugely successful business model (e.g. Plenty of Fish, OKCupid, et al). People spend a lot of time and energy looking for love online, but are often disappointed because an online profile can represent a severe distortion of reality. By using the mode of interaction described above, a user can find out additional information about another person who they are attracted to. This attraction may be verified by the user's physiological responses to seeing the other person, which confirms the attraction as genuine. This represents an improvement over traditional online dating as the process of attractiveness-matching is based on objective factors.

If the device picks up a person that you do not find attractive then the user can alert the system that it is in error so the system can add this as a data point for the classification algorithm. In situations where there a lot of people the system may be overwhelmed with the number of faces that need to be processed so features as length of gaze, salience of brain state related to attractiveness, and other physiological measures can considered before the system takes any action.

A variant of this use case is that two adults consent to share their information with each other. Another case of this is to allow other person to experience their own world through their video feed by the way the other user of Glass experiences their world. One adult can ask the other adult "May I share with you what I am seeing?" or "May I share with you my visual perspective?" where one adult may share with the other adult their view of the world through their video camera. This view can be embellished by the device's interpretation of the sending user's brainwaves. Effects of Augmented Reality of the video may be to use soft focus (e.g. soft focus lens when feeling dreamy, warmth can be displayed as colour shift where certain things are accentuated), blurring and colour tinting, horizontal blur (e.g. top and bottom are blurred), radial blur plus colour tinting can add an emotional tone of the image. Other video effects that may be applied may include: motion blurs and trails, adjust contrast to be crisp, enhancing lines, and make things seem more dramatic by changing perspective. These effects can be linked to the user's emotional state. In addition audio effects can also be enhanced by the user's brainwaves and or physiology. Audio effects such as band pass filter sound, conversations around person can be scrambled, tune into a conversation by beam forming, learning voice model, and then scramble other noise in environment. For instance an adrenaline rush of the user can be accentuated by an audio effect.

One user can share with another user the user's own physiological data such as heart beat allowing the other person to see it, feel it, or hear it. Other measures include pupil dilation, muscle tone, breathing. These are intimate measures and increase ability to connect with another person. The wearable computing device of the present invention is an avenue to share this information privately with another person. I might be interested in how correlated my heart rate and breathing is synchronized with another person.

The wearable computing device may use the analysis and interpretation of brainwaves and brain physiology to control the functions such as camera, microphone, video-camera and onscreen display, etc., of the device of another device. The control of devices may take into account the context of the person such as the task they are doing, the media they are engaged with, emails, the status of their digital personal assistant, their current location, the environment they are in (e.g. temperature etc.). The devices can be controlled directly through the volition of the user or indirectly by interpreting the state of the user. Direct control requires conscious effort by the user. Indirect control could be done by something the user is consciously aware of or not consciously aware. In addition to devices already in a device such as Google Glass, other devices can be controlled by analysis of brain states where the status and information of the device being controlled can be displayed, felt or heard through a Google-Glass like interface. For instance, changing television channels can be done through brain computer interface (BCI). The current channel can be displayed in the display. Learning how to control a BCI can be difficult. Information displayed on the display can help a person learn how to use a BCI and give feedback as to the degree that their emitting of brainwave signals comes to tipping a threshold where a control activity will occur. The device may provide feedback to the user to let them know if the brainwaves that they are emitting will be close to tipping a threshold of control. Things that can be controlled through BCI may include: lighting; heating; entertainment electronics (e.g. television, radio, CD player etc., volume, and audio characteristics); wheel chair; prostheses; computer display such as pointer and cursor; robots; kitchen appliances; bed position; and bed hardness.

The device may need to know the external device that the user wants to control. For example, the user may specify what he/she wants to control by for instance staring at a QR code of a wheel chair. The user can train the Brain Computer Interface controlling the wheel chair to better understand his/her brainwaves as commands. Glass can provide in its display the classification of the user's brain state. Different control modes can be selected to drive the wheel chair: forward and back or left and right.

Another example of control is to use the video camera of the wearable computing device or Google Glass to understand what the user wants to do. The user may want a robot to get him/her a can of coke. The user can stare at the robot and then the can of coke. Tactile feedback can also be provided from the Brain Computer Interface using an analogy from the real world of tactile feedback. The BCI can tell the user to try harder or easier to control the BCI by giving the user a feeling if they should push harder or softer, by increasing or decreasing effort to control something.

Application: Communication and Compatibility: Photograph Triggered by Attraction (A.2)

The wearable computing device of the present invention may be configured to be able to "tag" photographs taken by or viewed on the wearable computing device with emotional data. The emotional data may include the user's data as measured by the wearable computing device upon taking or viewing the photo and/or data gleaned from other users' publicly-available profiles. This tagging may manifest as a heads-up-display (HUD) output within wearable computing device.

The wearable computing device may establish a contextual baseline Brain State based on the wearer's profile, and possibly other brainwave characteristics that are aggregated statistics from other users. It uses an Algorithmic Pipeline to determine changes to Brain State, and determines if the user is attracted to the person the user is looking at via brainwave characteristics that are associated with attraction. Using publicly-available user data and profile data, the wearable computing device may also determines if the person the user is looking at is attracted to them. The answer is output via the wearable computing device, which notifies the user of the other person's attraction or lack thereof as a heads-up-display.

The benefit of these aspects of the present invention may include providing users with instant but discreet access to knowledge about how other people feel about them, and also providing for users to share this same type of information with other users. App developers, social media platforms and networks, and advertisers may also benefit from this.

To illustrate this application, the following example is provided. In this example, a user, "Bob", is wearing the wearable computing device when he notices a person whom he finds attractive at the coffee shop. The wearable computing device detects him noticing her, because his Brain State has changed from his baseline to indicate attractiveness, and this activates the wearable computing device to take a picture of the person. An app built into the wearable computing device matches her photo with publicly-available photos on Facebook and other social network platforms. The wearable computing device uses Facebook to obtain data from her wearable computing device, and relays it to Bob via heads-up-display.

Application: Communication and Compatibility: Help Engaging in Conversation with Another Person (A.3)

One possible advantage of the wearable computing device of the present invention is that it can offer information discretely to its wearer without others around them being aware of the content or that any information at all is being displayed or heard. Only the wearer can see what is displayed on their screen unless the wearer grants permission for that content to be accessible to any other user(s) through a network. In addition, only the wearer can hear audio from the wearable computing device since audio is transmitted through bone conduction which is not audible to others nearby.

For example, the wearable computing device may monitor the emotional state of the wearer. The type of feedback and type of information can be tailored to, for instance, the energy level of the user. The user faces another person and engages them in conversation.

For example, a photograph of the person is taken by wearable computing device and sent to a facial recognition database for pattern matching. The person may or may not be known to the user. The facial recognition database returns the name of the other person with a percentage confidence of the facial recognition match. In addition, other publicly known details about the person are present in the display. These facts can help provide tidbits of information to inform the user during the conversation.

For example, the wearable computing device may infer the emotional state of the other person through voice stress analysis, facial expression, body language and other physiological information that can be inferred by analyzing video of the other person. For instance, heart rate can be inferred by doing "video amplification" For an example of this process see http://web.mitedu/newsoffice/2012/amplifying-invisible-video-0622.html, the entirety of which is incorporated by reference. This technology amplifies colour changes in the skin that are imperceptible to the human eye and displayed so that one can see colour changes in a person's skin that are related to change in blood flow as the heart beats. Machine Learning can make predictions about the emotional state of the user based on features extracted from this information. Predictions in emotional state can help inform the user.

Some conversations can be challenging depending on the context such as a police officer interviewing a person for information, a job interview, a therapist counselling a patient, offering condolences to a person facing loss. etc. The emotional state of the wearer can affect the quality of these interactions. The wearable computing device can offer advice to the user to improve the quality of the interaction based on the user's emotional state. For instance, if anxiety is detected then the wearable computing device can suggest to the user to slow down take some slow deep breaths and become more mindful of their breath to bring them more into the present moment. Also the wearable computing device may detect ERN's that the wearer made and reveal these to the wearer if the wearer needs to have an accurate discussion.

Application: Early Response and Risk Assessment: Monitoring Factory Workers for Errors (B.1)

In an aspect, the wearable computing device of the present invention may be used to monitor workers, such as factory workers, for errors. This application may rely on detecting one or more error-related negativity events in the brain(s) of the worker(s). An error-related negativity (ERN) is an event related potential that occurs in the brain of person when they commit an error. The ERN can occur whether or not the person is conscious or not of committing an error.

Figure 47:
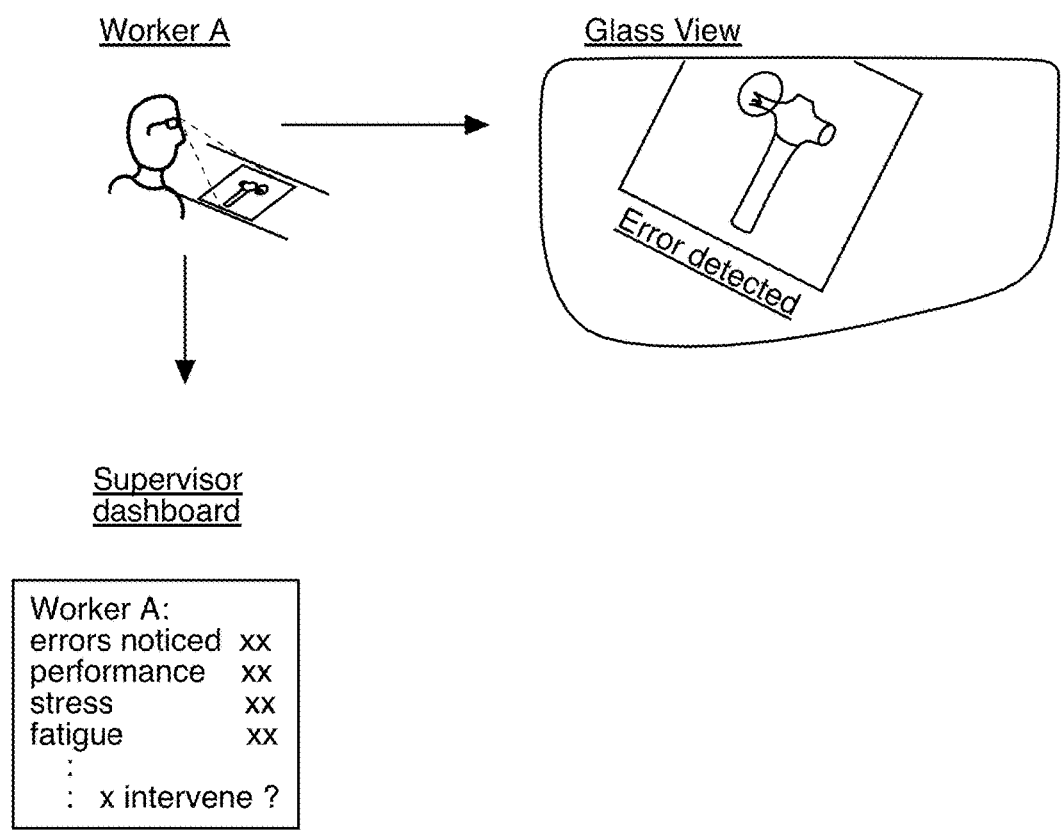
FIG. 47 illustrates a view in a display of the wearable computing device in accordance with an exemplary embodiment of the present invention.

In this scenario, with reference to FIG. 47, a line of workers on a factory line may be doing a set of repeated tasks. Each worker wears a wearable computing device of the present invention while they conduct their work. When an ERN is detected, the worker is alerted to the error (silently and out of notice of others around them) so that they may correct their error or scrap the work in progress. Glass can display the error using Augmented Reality where the part of the work that is in error is highlighted in color, as represented by the augmented reality encircling of an error detected as shown in FIG. 47. The device may optionally prompt the user to fix the error in a particular way. Also schematics, drawings and or assembly instructions may be quickly called in the worker's wearable computing device display to inform the work. The worker's supervisor can monitor the performance of the workers and suggest interventions or rewards tied to the level of error free work. Also the design of new manufacturing steps can be evaluated to determine which set of steps leads to the lowest number of ERN and therefore mistakes. In addition other brain states of the workers can be monitored for stress, fatigue, drowsiness that can impact their performance. Interventions such as suggested break times, change in the type of music, an office stretch break may be recommended.

Application: Early Response and Risk Assessment: Officer Pulling Over Motorist (B.3)

The wearable computing device may be used to provide an early alert and associated response to events witnessed by a wearer of the device. An emotional warning system implemented by the present invention may use sensors to determine Brain State, and triggers the wearable computing device to record visual evidence of conversations and altercations.

For example, the wearer of the wearable computing device or suite of devices establishes contextual baseline for the wearer's habitual Brain State and for workplace Brain State via Algorithmic Pipeline. Contextual baselines are dependent on context: location, occupation, activity, sleep, goals, desires, and other factors which help create a specific situation that is qualitatively differentiated from others. Contextual baseline user profiles can be stored in a variety of locations: within the device, in the cloud, on secure servers at the station house, or in all of these locations simultaneously. The device detects Brain State, with available Sensors. Available Sensors include: cameras, galvanic skin response, bone vibrations, muscle twitch sensors, accelerometers, pheromone and hormone detectors, gyrometers, and basic brainwave sensors. Analysis of EEG data indicates a brain state that requires additional processing. That feeds to a series of Processing Rules. Processing Rules determine how to proceed, and delivers an Output. Output could be a heads-up-display in the wearable computing device, a text message on a smartphone, or audio interaction via smartphone or earbuds.

One possible benefit of this implementation may include law enforcement and security personnel therefore having data on incidences of high-tension interactions, including both aggregate emotional/physical data and photographic/video evidence. Private security firms and military contractors may also similarly benefit.

Figure 48:
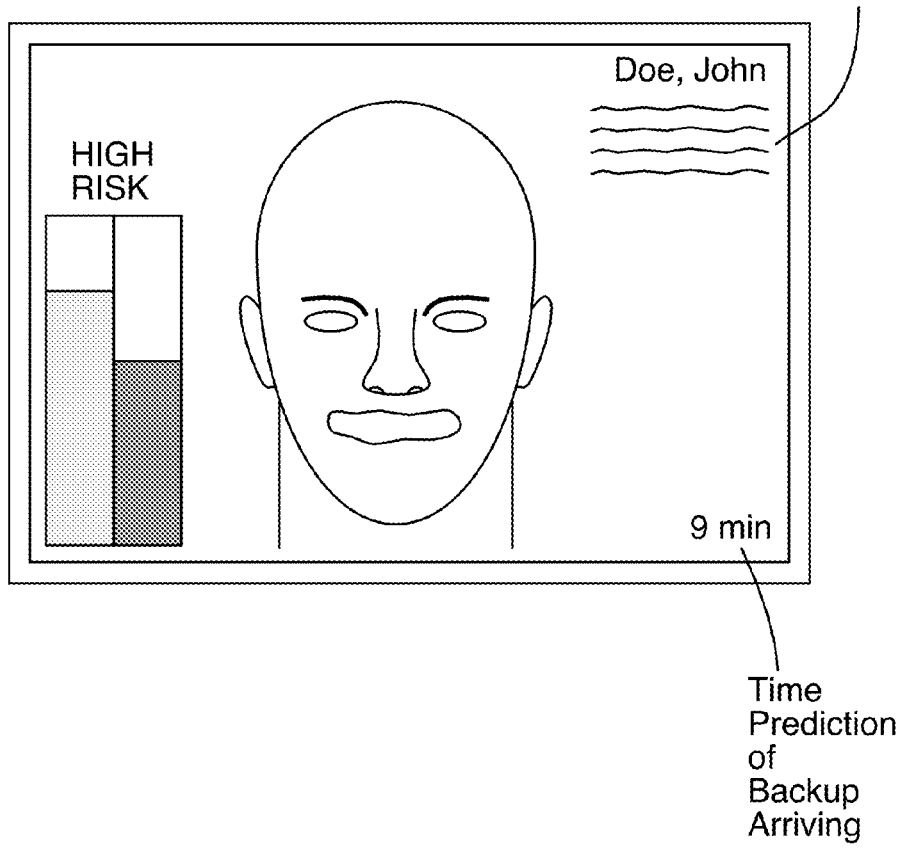
FIG. 48 illustrates a view in a display of the wearable computing device in accordance with an exemplary embodiment of the present invention.

In another example, with reference to FIG. 48, a law enforcement officer may pull over a speeding vehicle. The driver inside is stubborn and refuses to acquiesce. As tensions rise, sensors inside the officer's wearable computing device recognize his emotional response and warn him that he is in danger of changing his Brain State. The wearable computing device then begins recording the interaction between the officer and the driver. The wearable computing device may be set to operate in a state called "Officer on Duty". After he pulls over a speeding vehicle, the officer instructs the wearable computing device to alert Police Operations that he will be approaching a driver for speeding. The wearable computing device starts to video record the incident and to monitor the brainwaves of the user as well as the driver being pulled over, as shown in FIG. 48. The display of the device may present information to the officer including an identification of the driver using facial recognition; a list of the driver's prior criminal offences; a predicted time of backup arriving; and the officer's emotional state and overall situation assessment. The driver is subjected to video monitoring and audio monitoring looking for signs of stress and or deceit in their vocal responses. The wearable computing device recognizes that the officer is experiencing elevated levels of stress through physiological monitoring of brainwaves and other signs of stress from the officer such as levels of sweat through galvanic skin response, changes in heart rate variability, levels of gas associated with stress hormones etc. The algorithm pipeline ID predicts that the officer is in danger of losing his cool with the speeder. A message is sent to Police Operations where an officer in a remote control room is connected to the officer on the scene. The officer in the control room initiates a protocol of conversation that all officers have been trained to respond. The protocol may involve coaching tips through an audio feed or through the display to the officer. The coaching is intended to offer emotional and cognitive support to the officer in the field. In addition, a video record is also captured for future review and debriefing, the video record may also be used as evidence.

In addition, the feedback of the officer in the field and the control room may also be used during debriefing to fine-tune the algorithm that was used to detect elevated levels of stress. Additional factors may be brought into algorithm such as the officer having come from a very difficult and emotionally demanding previous incident that spilled over and was exacerbated by this incident. Information from the user's is used to improve the algorithm for future use. In this case it is decided that a baseline reading of the officer be taken to ensure that he is ready for active duty.

In another example, a driver is pulled over for speeding. He immediately turns on the wearable computing device to begin recording his interaction with the officer. The wearable computing device logs the driver's Brain State and delivers advice on how to proceed. While connected to the wearable computing device, the driver is able to contact his attorney and share the record with him.

In another example, a squad of riot police is kettling a group of students for arrest. The commander of the squad accesses her squad's Brain State profiles in the squad database. She begins monitoring the Brain State of the squad as they proceed. MUSE detects elevated tension in the group. The commander uses the wearable computing device to send helpful messages to the squad, reminding them of standard operating procedure before they begin.

In another example, a teacher is monitoring students for performance levels in learning. A school teacher or security guard may use a database to check which students are meeting normal brain state characteristics for their age. When a student's brainwave characteristics exceed a threshold, she refers them to the school guidance counselor. The wearable computing device alerts her to students who have persistent indicators of changes of Brain State that indicate a change in mental, physical, or emotional health. She can then begin monitoring these students for disruptive behaviors, signs of abuse at home, or possible violence at school. The monitoring of students can happen over a longer period of time and school teachers can see trends and associations with their brain state characteristics such as specific classes or times of day, etc.

Application: Emotagging: Mood Changes Tracked Using Video (C.1)

In another aspect, the wearable computing device may provide emotagging capabilities. Emotagging allows users to take photos of their surrounding environment each time the headband registers a mood change. Eventually, an emotional "album" of visual information is formed, which can help users sort through stimuli.

For example, as the user proceeds through her day, the wearable computing device logs each instance of a mood change and tells the wearable computing device to take a picture. The wearable computing device determines changes from contextual baseline Brain State using available Sensors. Possible Sensors include: cameras, galvanic skin response, muscle twitch sensors, accelerometers, pheromone and hormone detectors, gyrometers, and basic brainwave sensors. The photographs captured by the wearable computing device can go to a variety of locations: an onboard storage device, cloud storage, email or social networks, or they can be deleted. Within the scope of a mental health application, the pictures then become part of a private album along with emotional and environmental information, which can be shared with therapists or family members for discussion.

In a busy world full of stimuli, it can be difficult to know what exactly makes us feel the way we do. Collating stimuli based on emotion helps patients understand mental health "triggers" to mood changes and pursue evidence-based medicine in a way that can be shared with doctors, therapists, and family members. Rather than finding abstract metaphors for internal states, patients can discuss concrete moments in time that precipitated a mood swing with their support network and use them to decide on strategies for treatment. Users for this application may include mental health professionals and patients.

In an example of this aspect, "Chris" has been in therapy to deal with the grief of his wife's death, but finds it difficult to explain to his therapist exactly what he's feeling or why. His therapist suggests he wear a wearable computing device of the present invention or suite of wearable computing devices paired with a wearable display device, so that the visual and environmental stimuli can be logged for discussion. The device notes mood changes and changes in sleep patterns and distraction, via brainwave characteristics. When Chris differentiates from contextual baseline Brain State, the wearable computing device takes a photograph of what he is staring at, determining the object of his gaze via EOG/eye-tracking when the emotion is over a threshold. Over time, an iterative mood profile of Brain State plus visual information develops. At any point, Chris or his therapist can compare his Brain State to previous baselines, and determine how his therapy is progressing.

Some brainwaves are reactions to discrete stimuli and are called event related potentials which occur within a few milliseconds lasting to several seconds after a person consciously or unconsciously receives a stimuli. The stimuli may be an internal event such as a though or it may be an external event such as a sound, seeing an image, physical touch, sudden heat, or the feel of wind etc. Other brainwaves are not strongly associated with stimulus but are indicative of brain state of a person in terms of examples: mood, emotion, focus, drowsiness, sleep, attention, problem solving and, rumination, retrieving short term memory, retrieving long term memory and other thought processes. These brainwaves can be short lived or long lasting. This aspect of the invention uses brainwaves that are unusually strong for the person that exceed some threshold.

A calibration step may be provided prior to the performance of emotagging. For example, a pre-determined set of exercises may be conducted where brainwave data is collected from the individual. The exercises can include: math problems, focused attention on breath, just simply to relax, recall a painful memory, recall a happy memory, and recall a time that somebody made you angry, etc. In addition the calibration may also provide stimulus to the user in the form of normal tones interspersed randomly with tones that have distinct characteristics. The person may be asked to note when they perceive these oddball tones. The amplitude, duration and latency of a person's brainwave reaction i.e. event related potential is related to a number of cognitive processes in a person's brain such as attention and focus. In other cases asymmetries of the ERPs across different regions of the brain (example right hemisphere compared to left hemisphere) can be informative about a person. The EEG of the signal during the exercised are analyzed to determine a baseline of the person. They can be compared to EEG databases of normal population of individuals with the same age, gender and demographics as the person under calibration. The person's EEG can also be compared to databases of people with disorders such as anxiety or depression etc. In addition, a statistical model may be built with the data from these databases using machine learning methods. The machine learning methods create a predictive model which for instance can output the probability that a person has certain disorders or other characteristics of brain function. The predictive model may also supply the degree to which a person is believed to have a disorder or brain characteristic. The probability and or degree of a characteristic may be used to inform the treatment of a person. This information can be used to help focus on which environments and or situations should be examined more closely. It can also inform which brainwave characteristics should be the focus of attention during the investigative phase. However, the primary purpose of the calibration is used to establish a baseline statistics (mean, variance, histogram distribution etc.) for the brainwave characteristics measured during the calibration phase. In some cases, multivariate distributions may be built by considering the co-occurrence of brainwave characteristics. Thresholds for univariate or multivariate distributions of brainwave characteristics can be set using the person's data, or from statistics from across a population of people's EEG recordings. Note that the calibration phase may be done periodically to continue to update the statistical model of the person for different times of day, week, sleep quality, after eating, after exercise etc.

After calibration, the investigative phase may begin. With the wearable computing device and a statistical model of the person based on their calibration along with the thresholds the person goes through the motions of their daily life. When the person's brainwaves exceed a threshold, the devices' video camera starts recording the audio and video of what they are currently experiencing. In addition, biological signs in addition the person's EEG may also be recorded. The video recordings, EEG recordings and their brainwave characteristics, threshold that were exceeded and other data are recorded into the person's User Profile. This data may be used to create a prediction of the user's brain state at the time a threshold was triggered. Over time a number of recordings are made in this way. The data is analyzed to determine patterns of situations that are triggers to the person. These can be used to help determine a strategy to help the person deal with these situations.

Next, model improvement may occur with the person's feedback. During the investigative phase, thresholds were exceeded that prompted video-recordings. These also came with a prediction of the person's brain state at the time. The person can review this prediction, while it is happening or offline at a later time. The prediction may agree with the person's subjective opinion or the person may disagree and re-state what they think their brain state was. This information can be used to adjust the statistical model and make it more accurate.

In another example, Chris is having trouble sleeping. When he goes to a sleep clinic, the clinic finds no trouble with sleep apnea or other sleep disorders. However, the clinician advises that Chris wear a wearable computing device of the present invention paired with Glass to determine what he is looking at, eating, emotional state, exposure to stimulation like video games or online late at night, or other activities before bed that might be keeping him awake. Using Steady State observation paired with brightness detectors, cameras, and heart rate monitors, the wearable computing device logs that Chris is looking at too many bright, stimulating things before bed. Glass takes photos of what Chris is looking at before bed. Working with Chris as an individual user, the device develops its own personalized Process Rule to tell Chris when the things he's looking at are too bright.

In the use cases that involve video recording a circular buffer can be used to continuously video-record everything in view of the user. If the user experiences a salient brain state that is used to trigger a video-record then the current video-recording in the circular buffer can be tagged and uploaded starting from a few seconds to minutes in the past to capture the circumstances that led up to the salient brain state. If no salient brain state occurs then the content of the circular video buffer are overwritten.

Application: Emotagging: Apply More Scrutiny to People Triggering Brainwave Recognition (C.2)

In an aspect of the present invention, the wearable computing device may perform various actions when the person's brain recognizes a person. Therefore, a routine brain scan of the user may help security personnel identify and recognize persons of interest, including suspects and missing children, when the user might otherwise be inclined to ignore their instincts.

For example, the wearable computing device may determine the wearer's contextual baseline Brain State after time spent wearing the device in multiple contexts, via Algorithmic Pipeline. When a security guard or police officer scans a crowd and recognizes someone, the wearable computing device may log the recognition as a P300 and takes a photograph. Process Rules offer multiple options depending on location, jurisdiction, rank, and prior records. Depending on these factors, the photograph can be matched against local law enforcement databases, sex offender registries, or Amber Alerts. This may help personnel on the ground do their work faster; they can act on hunches and cross-reference conflicting information to rule out or upgrade persons of interest. Customer segments for this application may include law enforcement, security personnel, theme park and other attraction personnel.

In another example, a voice command from a security guard informs the wearable computing device that she is on active duty. The wearable computing device starts using rules and algorithm pipelines associated with her duties. The video camera line of sight is adjusted to align in the same direction as the user's eye gaze. A security is on patrol looking at people she passes. While on a college campus, a security guard sees a young girl she thinks she recognizes. A P300 recognition event is detected by the wearable computing device monitoring the security guards brainwaves. She is not sure, but the headband recognizes her P300 response. The process rules associated with the context of being on active duty sends a message to the wearable computing device to note in the video record the images associated with the P300 image and occurring at the same point in time as the P300 event. The wearable computing device sends that image to a local law enforcement database. The picture is similar to that of a kidnap victim from ten years ago. The match in the database automatically pops up in the jurisdiction that filed the kidnapping case, alerting the last-known detective on the case. Meanwhile, the match gives the security guard probable cause to follow the girl.

In an implementation, the video camera line of sight of the wearable computing device may be adjusted to align in the same direction as the user's eye gaze. The security guard sees someone and this consciously or unconsciously registers as a recognition brain state such as P300. The wearable computing device may be constantly monitoring the user's field of view. When the algorithm pipeline determines that the user recognizes somebody, the field of view being recorded by the video camera is tagged with this information. A video of section of video is sent to the Cloud or sent locally on a computer the user is wearing or sent to the wearable computing device. Features from the face of the person that the user is recognized are extracted from a still image. These features can include eye colour, distance from the centre of one eye to another etc. Using these features a search for a matching person is initiated through a database that resides in the Cloud.

This architecture could be used to recognize suspects in any crowded area, and match them against parole data. For example, if a woman who filed a restraining order on her ex-boyfriend recognizes him in a crowd, the wearable computing device can log the recognition response, take a picture and take note of the GPS coordinates, and the entire device can send the data to the woman's lawyer or local law enforcement.

Application: Evaluating Response to Stimuli: Evaluating People (D.1)

The wearable computing device of the present invention may determine Brain State changes that indicate a response to specific stimuli that is different from contextual baseline Brain State. The device may relay augmented reality information to the user through the display in those specific instances that will help them navigate situations in real time. This may be accomplished by the device establishing a contextual baseline Brain State (e.g. via an Algorithmic Pipeline) after filtering data from multiple sensor inputs. This sensor data may be indicative of a strong brainwave response (e.g. P300, ERN, Steady State, or otherwise) to specific stimuli in the outside world. The wearable computing device may use context-specific Process Rules to determine an output that will be contextually appropriate for the user, and relay the output information via display, text message, email, social network, or other suite of services. This may provide users with real-time access to meaningful information in context that has direct bearing on how they should behave within a specific situation, such as how to handle a social interaction, how to solve a problem, how other people are feeling in their general vicinity. This application may be of particular use to teachers, factory owners, manufacturers, police officers, law enforcement, hiring managers, marketers, advertisers, campaign managers, and/or security personnel.

In an example of this application, "Robert" is the dean of a prestigious all-girls private school. In the interest of security, and to maintain good relationships with parents and donors, Robert must find a way to vet potential hires that tests them for attraction to young girls in a measurable, scientifically-accurate way. At the same time, he wants to keep this data discreet so as to avoid a lawsuit. Robert asks candidates to wear a wearable computing device of the present invention as they tour the school. Potential hires are assessed to determine if an abnormal reaction occurs similar to pedophiles. The device logs changes in Brain State based on a profile in the cloud made publicly available from local law enforcement, that matches aggregate data culled from pedophiles in prisons who have volunteered their responses. The device collects data on what candidates spend time looking at, and how Sensors respond to changes in their Brain State. The data is stored locally, and Robert can review it as part of the hiring process.

In another example, "John" is a teacher. John uses data from the wearable computing device to learn about the mental and emotional states of his students in the classroom, based on changes to contextual baseline Brain State. The device regularly pings other devices of the present invention worn by students for ERNs, P300s, change in focus (beta to theta ratio) and other brainwave characteristics as well elevated heart rate. Changes to Brain State are relayed discreetly to John via the device. The data is stored locally in John's device, keeping data relatively private. In one day, John sees a student who is struggling with a new concept and exhibiting numerous ERNs, and rising levels of frustration and decides to introduce that student to a tutor. Then he sees another student who is making a determined effort to focus more intently on the subject matter, and he makes sure to take that student aside and praise her for making such an effort. With another student who is falling asleep, John makes sure to ask him if he ate breakfast that day and whether he's staying up too late at home.

For this application, calibration may occur first. In calibration, a pre-determined set of exercises are conducted where brainwave data is collected from the students. The exercises can include math problems, focused attention on breath, just simply to relax, recall a painful memory, recall a happy memory, recall a time that somebody made you angry etc. In addition the calibration may also provide stimulus to the students in the form of normal tones interspersed randomly with tones that have distinct characteristics. The student may be asked to note when they perceive these oddball tones. The amplitude, duration and latency of a student's brainwave reaction i.e. event related potential is related to a number of cognitive processes in a student's brain such as attention and focus. In other cases asymmetries of the ERPs across different regions of the brain (e.g. right hemisphere compared to left hemisphere) can be informative about a student. The EEG of the signal during the exercised are analyzed to determine a baseline of the student. They can be compared to EEG databases of normal population of individuals with the same age, gender and demographics as the student under calibration. The student's EEG can also be compared to databases of people with disorders such as anxiety or depression etc. In addition, a statistical model may be built with the data from these databases using machine learning methods. The machine learning methods create a predictive model which for instance can output the probability that a student has certain disorders or other characteristics of brain function. The predictive model may also supply the degree to which a student is believed to have a disorder or brain characteristic. The probability and or degree of a characteristic may be used to inform the treatment of a student. This information can be used to help focus on which environments and or situations should be examined more closely. It can also inform which brainwave characteristics should be the focus of attention during the investigative phase. However, the primary purpose of the calibration is used to establish a baseline statistics (mean, variance, histogram distribution etc.) for the brainwave characteristics measured during the calibration phase. In some cases, multivariate distributions may be built by considering the co-occurrence of brainwave characteristics. Thresholds for univariate or multivariate distributions of brainwave characteristics can be set using the student's data, or from statistics from across a population of people's EEG recordings. Note that the calibration phase may be done periodically to continue to update the statistical model of the student for different times of day, week, sleep quality, after eating, after exercise etc.

Next, the monitoring phase may begin. With the wearable computing device configured with a statistical model of the student based on their calibration along with the thresholds the student goes through their school day. When the student's brainwaves exceed a threshold Muse Glass video camera starts recording the audio and video of what they are currently experiencing. In addition, biological signs in addition the person's EEG may also be recorded. The video-recordings, EEG recordings and their brainwave characteristics, threshold that were exceeded and other data are recorded into the student's User Profile. This data may be used to create a prediction of the user's brain state at the time a threshold was triggered. Over time a number of recordings are made in this way. The data is analyzed to determine patterns of situations that are triggers to the student. These can be used to help determine a strategy to help the student deal with these situations. The student's teachers and guidance counselor can also be notified of thresholds being exceeded in real-time. This way they can help the student with a specific problem faced in a course or a systemic problem such as lack of focus because of inadequate sleep, nutrition etc.

Next the statistical model may be adjusted. During the investigative phase, thresholds were exceeded that prompted video-recordings. These also came with a prediction of the person's brain state at the time. The teachers can review this prediction, while it is happening or offline at a later time. The prediction may agree with the teacher's subjective opinion or the teacher may disagree and re-state what they think their brain state was. This information can be used to adjust the statistical model and make it more accurate.

In another example, a team of employees working on a project may each put on a wearable computing device of the present invention. The team lead, also wearing one of the devices may be presented with brain state information of each team member. The team lead may then use that information to change how the team lead communicates with the respective team member.

Application: Evaluating Response to Stimuli: Tracking Political Debates (D.2)

In this application, the wearable computing device may detect a user's response to a particular stimulus using brain state information. For example, "Daniel" is watching a televised debate between two candidates running for Prime Minister while wearing the wearable computing device of the present invention. During the debate, as the candidates speak, Daniel cycles through positive and negative mental states as he listens to the debating points. Daniel's instantaneous reactions from his brain scan are fed through to polling firms (or other interested third parties) over the Internet, who then aggregate data from other individuals who are watching the debate, producing a "realtime" graph of public perception of the candidates. Political parties and other interested organizations may purchase access to the raw data to tailor advertisements to the public. This information can be stored either in the cloud or on a company's local servers. Realtime data from Muse Glass can be easily sorted into demographic categories, allowing even greater optimization of marketing resources The subconscious opinions users hold about products or even people provide a much more valuable insight into their true opinions than what they are willing to say publicly. By deploying technology that allows third parties to capture instantaneous brainwave information directly from consumers, distortions from actual intentions are minimized.

Application: Mood Drive Recreation: Movie Recommendation Matched to Mood (E.1)

By analyzing biometric inputs, the wearable computing device, or another connected device, such as Google Glass, may be able to provide entertainment and leisure options to match the mood of the user. There is a theory that people like to listen to music that matches their mood, i.e. if one is angry, sad or happy then the music one listens to should match their mood (See: http://www.healthline.com/health-news/mental-listening-to-music-lifts-or-reinforces-mood-051713). It is believed that one will choose other forms of entertainment such as movies that match one's mood.

For example, "Othello" is at home early one evening and he decides he wants to head to the cinema and watch a film. He asks the wearable computing device to retrieve the film listings for the nearest cinema. Information is retrieved from film listing websites or an internal or externally-accessible database. The device consults his GPS location and finds listings for the multiplex nearest Othello's home using mapping tools. The device scans Othello's brain and determines he is feeling happy and excited. Information is derived from brainwave analysis. Based on this information, the device suggests that Othello see an upbeat film that is currently playing. The website that has film information has a label indicative of the type of emotional content of the movie or it may use current classification such as comedy, drama, action, horror etc. In addition the device may gather other information from the movies that the user has rated such as actors in the film, plot summary, director, and setting of movie. These features may be used to help make suggestions to the user based on machine learning of the features and their association with the rating the user gives the movie. In addition, the user may choose to wear the wearable computing device while watching the movie and it will learn the user's response to the movie moment by moment and also have aggregate statistics for the whole movie. The following are example brain states that could be inferred: like, dislike, emotional valence (i.e. positive or negative emotions) and arousal (low energy to high energy). Each film adds another record to the database of movies that the user has rated. Alternatively, the wearable computing device may scan Othello's brain and determines he is feeling sad and depressed, as determined through brainwave analysis.

Othello may also experience an ERN when presented with suggestion of a movie that he does not agree with. Or in another case, Othello disagrees, tells the device he's in the mood for a somber film to match his mood. Based on this input another record is added to the database of movies that the user has rated their preferences. In this case, this movie may have a stronger weight associated to with it in terms how it influences the statistics of the learned model of preferences and other movie features. It may also be coded as a rule such as "Do not recommend horror movies except during the month of October." The device may re-calibrate its search suggestions, and brings up another movie in line with Othello's indicated mood. Data about the film is again derived from film listings websites like rottentomatoes.com. Othello agrees with the recommendation and the device, or a connected device, like Google Glass enters navigation mode so Othello can navigate his way to the cinema.

Tools that try to suggest content based on the user's mood are helpful, but they are unlikely to make accurate, sensible recommendations 100% of the time. This is because someone who is in a certain emotional state may wish to remain that way (and have content delivered accordingly) or they may wish to change their emotional state by consuming content that opposes their thought patterns. Over time, the device may be able to learn which choice the individual prefers more, but as the learning curve is being built it is wise for the device to yield to the user's individual preferences.

Application: Evaluating Response to Stimuli: Mood Driven Walk (E.2)

Figure 49:
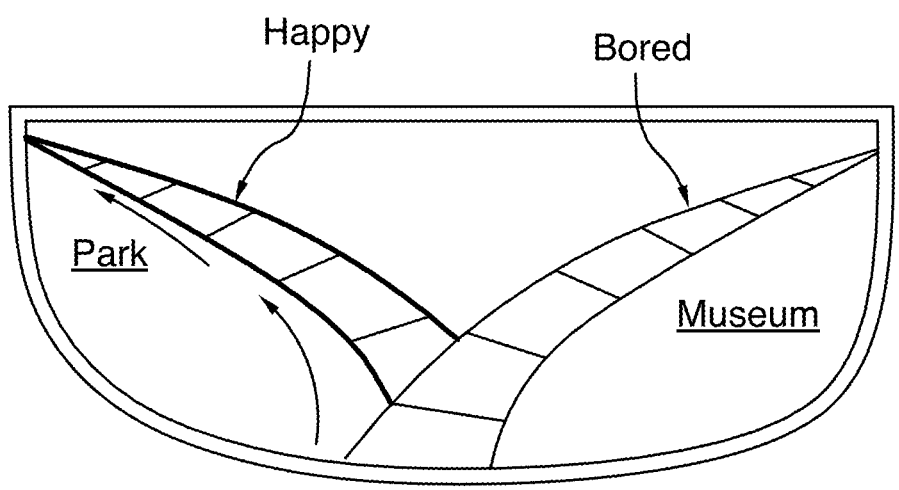
FIG. 49 illustrates a view in a display of the wearable computing device in accordance with an exemplary embodiment of the present invention.

In an application of the present invention, the wearable computing device may attempt to aid the user in achieving a sense of meditative focus through walking meditation and engaging in a space, based on feelings logged in the device. The device may curate an experience of a city, museum, shopping centre, or other space. The user may initiate a locative program that develops iterative directions and advice using some or all of GPS, Brain State, and visual information from a camera of the device. The device may establish contextual Brain State, and determine a pathway through a space based on sensor feedback. At different junctures or intersections, the wearer can "check in" with the device to decide where to go next, as shown in the augmented reality display view of the device of FIG. 49. This application may depend on a location database, route recommendation, and use preference update.

The location database may be populated over time with positive feelings associated with specific categories of locations. The user is running a background application in their device that keeps track of geographic locations that are associated with positive feelings. The application chooses an algorithm pipeline that analyzes the EEG signal from the sensors. The algorithm pipeline, as an example, can be one that analyzes asymmetries in the pre-frontal cortex for higher alpha in the right hemisphere which is associated with positive emotion. Another example of an algorithm pipeline that could be used to determine when positive feelings are occurring is through global increase in alpha power which is known to be associated with feelings of relaxation. While a user is wearing the device a score of their positive emotions may be continuously calculated (for example, at a rate of once per second) as an output from the algorithm pipeline. The score is proportional to the level of positive feeling that the user experienced. A rule residing in the rules engine is used to create a label of the user's emotional state—in this case a positive feeling. An example of a rule is: when a score of positive emotions exceeds a preset threshold for greater than two minutes continuously then label this period in time as a positive feeling. The latitude and longitude of the user's coordinates are captured using signals from GPS satellites received by the device when a positive emotion is predicted. The latitude and longitude is used to look up a location database, for example in Google Maps. The location may be associated with a category of location such as a specific type of business (e.g. Indian restaurant or book store or a movie theatre), or the location may be associated with a recreational activity such as a community centre or a trail in the country. The raw EEG data associated with this two minute period in time is labeled with a begin event and end event timestamps in the User's Profile. The type of event associated with this EEG signal is labeled "positive emotion". In addition, the GPS coordinates and the category of the location (e.g. country trail) along with other data such as photographs taken by the device or audio recordings made by the device during the two minute or longer period are also referenced. These photographs can also be uploaded to the user's Facebook account. In addition, the score of positive feeling is also stored. All of this information is stored in the User's profile to be referenced for a future time. Over time, the user develops a database of positive feelings associated with specific categories of locations.

The device may recommend a route to the user. When the user wants to have a positive experience and they are in a new location or want to experience familiar territory perhaps in a new way they ask the device to guide them on a walk. Other emotional goals may be possible (e.g. positive emotion). The wearable computing device determines the user's current GPS location. In one method the location database does the processing. A query is sent to a location database such as Google Maps with a list of preferred location categories such as: city park, library, coffee shop, etc. Each category also is ranked based on the history of positive emotional scores based on an average of these scores as found in the user's location database. Locations near the user's current location may be searched and ranked using a metric of distance weighted by the score of the positive emotion related to category of the location. The device, or the database, or connected remote server may select a route based on these metrics and sends a list of directions back to the wearable computing device for the user to follow.

As the user follows the path suggested they can add information as to the accuracy of the predictions offered by this application. Input from the user as a voice command such as "Sorry, Muse Glass, I don't like big chain book stores, please only send me information on boutique book stores". In this way, the accuracy of prediction and the nuances of the user's preferences can be updated in their User Profile.

This application may add value to existing spaces through emotionally-relevant curatorial function and may boost the personal and emotional value of going for a walk, especially in places the wearer might not be familiar with. This application may benefit curators, academics, designers, architects, and therapists.

For example, "Dean" is angry at his brother and needs to go out for a walk, but he doesn't know much about this area of town. He engages the service to help take him on a tour of the place. It takes him to locations that other people have marked as calming or peaceful, and soon he is able to approach his problems with his brother from a new emotional angle. The service helps guide him back to where he started using GPS, but he is in a much different frame of mind now.

For example, "Dean" is new in town and trying to find his way around the neighborhood surrounding his apartment. He has access to Yelp and other services, but he decides to create a map of the area based solely on how each spot makes him feel. Using the wearable computing device, and optionally, other connected device(s), he can tag different streets, alleys, eateries, and parks with how they made him feel. He can also do this for exercise, creating a meditative running or walking trail to get him ready for the day.

Application: Pattern Recognition for Individuals: (F)

The device responds to an external event or an internal state, processes the information and provides an output, as a form of pattern recognition. The device may recognize a connection between internal brain states and external events or environmental stimuli. It then outputs suggestions based on these patterns via a display.

The wearable computing device may establish a contextual baseline Brain State based on prior brainwave patterns in the user, and aggregate user data from other users made publicly available in the cloud, via server, or on local devices with onboard storage. By filtering inputs through the Algorithm Pipeline, the device may notice changes to baseline Brain State via multiple sensors, such as camera eye tracking/EOG, Beta:Theta ratio changes, P300s, ERNs, galvanic skin and temperature changes, and changes to heart rate. The device turns to processing rules for each input to determine an output that is context-dependent. The device can pattern match these changes to Brain State against external inputs, stimuli, or events. The device then presents heads-up-display suggestions at the display, creating a feedback loop of information between the wearer and the device.

This application may be able to identify a relationship between internal Brain State changes and external events and environmental stimuli. This allows the device to make meaningful suggestions in context, in real time. Over time, the device may build more profile data for individual users and aggregate users, and make smarter predictions about their desires and behaviour that in turn create smarter, better targeted outputs. This application may be of benefit to developers, advertisers, marketers, and designers.

Application: Pattern Recognition for Individuals; Example: Finding the Right Restaurant when You're Hungry (F.1)

For example, "Kevon" is driving along the highway in his car, wearing the wearable computing device of the present invention. Kevon sees a billboard advertising a restaurant he has been to before. Image recognition in the device flags this restaurant. A database of restaurants is maintained on the cloud and is sent to Kevon's mobile device on request. A measure of Kevon's brainwaves reveals he is hungry now.

Since his wearable computing device is aware that Kevon has been to the restaurant before, it performs a Google search or consults a 3rd party app to locate the nearest branch of the restaurant and to see if the store is having any offers/specials. This data is stored remotely on the cloud/Internet and is delivered to Kevon's mobile device upon request The device then provides a Google map overlay (or similar) pointing towards the restaurant, then will display relevant sale/coupon information once Kevon arrives. Sale and coupon information is either stored on the Cloud or is stored on a retailer's servers and is delivered to Kevon's mobile device on demand.

While Kevon is at the restaurant and enjoying his meal the AR device will connect with his nutrition management software to ensure he's eating according to his diet plan. Kevon's dietary plans may be stored remotely on the cloud.

As a user's emotional and physiological states are constantly changing, the device may continually monitor the individual's internal state and may be ready to deploy novel strategies based on that information.

Application: Pattern Recognition for Individuals: Example: Nicki has Trouble Sleeping (F.2)

For example, "Nicki" decides to use a stress tracker provided by the wearable computing device. The device detects Beta:Theta ratio changes in Nicki's sleep patterns, and uses other Sensors to detect ERNs, P300s, and other changes to Nicki's Brain State. The device, or another connected device, may uses brightness detection to see if Nicki's environment is too bright. Based on patterns in Nicki's profile, the wearable computing device makes suggestions via heads-up-display to help Nicki sleep better over time.

Application: Pattern Recognition for Individuals: Example: Roger Gains a Great Deal of Enjoyment from Music (F.3)

For example, "Roger" may see or experiences music that he greatly enjoys, and he generates a strong P300. The device takes note of this response, and photographs what he's looking at when he feels it. The device may use an algorithm to match images, and learn the context in which Roger experiences his feelings of anticipation. Over time, the device is able to send Roger information pertinent to his tastes and Brain States based on having pattern-matched his responses with the images that are saved via a heads-up-display of the device or a connected device.

Application: Pattern Recognition for Individuals: Example: Joanne is a Bargain Hunter (F4)

For example, "Joanne" is a bargain hunter. Based on the negative brainwave reactions to prices she sees, the wearable computing device develops a sense for when she is looking at prices above her desired threshold. Then, it begins guiding her to prices she is most likely to take advantage of, optionally in connection with another device like Google Glass, and sending her offers from online. Over time, the wearable computing device learns how to guide Joanne through multiple shopping experiences, including those in stores in which she has never visited before. The wearable computing device can learn the preferences of its users and help guide them in their daily tasks.

Application: Pattern Recognition for Individuals: Example: While Planning New Developments to a Run-Down Neighborhood (F.5)

A council on urban development may use aggregate data from the local population to help identify matches between internal feelings and external stimuli, such as new developments, green spaces, or transportation. For example, "Scott" is planning a barbecue party. The wearable computing device may know he is planning one because he has placed the event in his calendar, accessible to the device. The device may immediately begin scraping the Internet for online ads that are related to barbecues, like meat, fuel, and drinks. The device may interpret his reactions to these ads based on changes to his contextual baseline Brain State. The wearable computing device responds to P300s for the cuts of meat he wants, and saves the information for future use. Over time, Scott's profile is built within the device, to be shared with third-party vendors.

The device may be aware of the web site that is currently being displayed on-screen. The user's brainwaves are being monitored for P300 waves almost on a continuous basis. P300 is one example of an event related potential associated with recognition or novelty. The P300 wave needs to be associated and time locked to a stimulus source such as a particular photo or sound. One example of how to synchronize events detected in EEG is to use SSVEP. SSVEP requires an object on the screen (such as image or photograph) to vibrate at a specific frequency. The brainwaves of the occipital region of a user looking at an object on-screen that is vibrating at a specific frequency will also vibrate at the same frequency as the on-screen object. The algorithm pipeline looks for co-occurrences of the P300 wave and a detected SSVEP. The frequency of the SSVEP will be uniquely associated with the on-screen object. The strength (usually amplitude) of the P300 will be calculated along with the time of its occurrence will be time-stamped as a recognition or novelty event. Features of the on-screen object that triggered the recognition or novelty event will also be extracted. These features can include text included with the image, information about the web site where the image resides and other meta information about the image—example of features—"web site: www.buyBBQ.com", "picture: a cast-iron barbeque", "manufacturer: Broil-King", "six burner model", etc. Data mining and machine learning can be used to determine preferences of a user as they navigate through the internet.

Application: Pattern Recognition for Individuals: Example: Emeril Wants to Eat Healthily (F.7)

For example, "Emeril" has made a public goal within his calendar and social media platforms, accessible to the wearable computing device, so the device, or a connected device knows what he would like. But Emeril's Brain States change when he looks at unhealthy foods; he has strong attractions (P300s) for foods high in sugar. Over time, the wearable computing device recognizes the way his pulse quickens and how his Brain States change when looking at these unhealthy foods. To assist him in his goal, the wearable computing device begins to screen out search results and visual inputs related to the unhealthy foods.

Application: Pattern Recognition for Individuals: Example: Jim Eats Gluten (F.8)

For example, "Jim" slowly loses focus and feels sleepy (generating multiple ERNs related to work while also changing his Beta:Theta ratio) whenever he eats gluten. Over time, the wearable computing device learns the pattern between Jim's consumption of gluten and his change in Brain State. From then on, Glass helps Jim remember that gluten has a negative impact on his performance at work, via heads-up displays, text messages, emails, and colour changes within his visual field.

A user's diet and its relationship to performance and mood may be analyzed by the wearable computing device. The device may detect that the user is eating because chewing has very strong and distinctive patterns of electromyographic signals produced by his jaw muscles and picked up by EEG and or EMG sensors of the device. Note that EEG and or EMG surface sensors can easily pick up muscle contraction from the users face. The device may take a picture of the food the user is looking at corresponding to the same time the device has detected jaw muscle contraction. This photograph is analyzed for caloric content using visual pattern recognition. Note that this is currently done using human eyes but it is expected that future functionality will be able to analyze the content of food from photographs. In this case, the analysis of the food reveals that is high in fat content, and high in carbohydrates. In addition, the weight of the food consumed may be estimated directly by a scale under the user's food (i.e. a pressure sensors in the mat underneath the plate). The user's goal is to maintain high levels of energy and mental focus lasting for hours after a meal. For several hours after the meal, the device may analyze the user's brainwaves for signs of focus. A continuous estimate of focus is predicted from the user. In addition, accelerometers in the wearable computing device are used to detect signs of sluggish movement and sudden head bobs that may be indicative of "sleep jerks" common to many people as they catch themselves drifting to sleep but suddenly wake-up when the realization is made that they are falling asleep. Over time, data about the relationship of the food consumed by the user and the consequences in their focus, drowsiness and energy and can be distilled into a set of rules. These rules can suggest best times to eat and menu choices and portion sizes that allow the user to optimize their performance.

Application: Pattern Recognition for Individuals: Example: Judy is Distracted at Work (E.9)

For example, "Judy" is distracted at work and the wearable computing device uses multiple Sensors to determine what is distracting her, based on her ERNs and her levels of anxiety (e.g. determined by Algorithmic Pipeline). The device works to help her find Steady State focus, and achieve a more meditative frame of mind while at work, by providing her alternative stimuli and screening out other distractions. The device can give her literal "tunnel vision" so she focuses on the task at hand, and its sound inputs can play soothing music for her.

The user may be assigned a task with a deadline by her boss. The user's work environment and computing resources are controlled to help the user maintain focus and motivation towards the task. Factors such as stress and ease of distraction can be inferred from the user's brainwaves and can be related to the level of information that the user is ready to process.

First, a calibration step may be performed. The user may go through a set of calibration exercises that determine associations of her brainwaves to example distractions, stress, and focus.

Next, visual and audio distractions are removed to allow focused work. The user's brainwaves are being monitored for characteristics associated with focus and distraction. The wearable computing device can apply noise cancellation, insert audio or music helpful to the task at hand. In addition, Augmented Reality can be applied to help focus the user to help prevent visual distractions from entering the user's field of vision. The user's peripheral vision can be darkened of made diffuse to help prevent visual distractions reaching the user. The level of noise cancellation applied through headphones or through bone conduction can be modulated by the level of focus and or distraction experienced by the user. In addition, the level of distracting emails other than those required by the task are filtered out of the user's inbox and are not displayed until after the deadline or when the person's analysis of brainwaves reveal a readiness to get more information.

Next, offline strategies that help improve focus are provided to help the user reduce stress and focus on their work including mindfulness breaks. The user engages in an APP that helps them relax and maintain focus based on neurofeedback and guided voice instruction. After this, the guided instructions ask the user to visualize what needs to be done and think of any obstacles that are in the way. After this exercise, a discussion is held with the team that the user is working with to finish this task. Obstacles and plans are discussed. The work team is more focused after bringing a more mindful approach to their work.

The wearable computing device may suggest different exercises that help her focus by decreasing any physical mental or emotional challenges she may be facing. The user would then take a break from current activity to reset her level of focus to come back more energized and attentive.

The wearable computing device may determine when the wearer's attention is wandering and make a visual aspect in the wearer's field of view more visible on the display, possibly by highlighting it, or modifying brightness or contrast of all or a selected portion of the display.

Feedback may also be presented on the display regarding how much time was spent in a state of lacking focus. The length of time on-task, extent of distraction, time wasted due to distraction may each be displayed.

In a sports activity such as golf, the wearable computing device may provide a "blinder" feature where dynamic feedback is provided to help one get into the groove of the shot. For example, an environment familiar to the user may be displayed on the display in combination with the golf view. The familiar environment may be comforting because the user may be able to more readily remember being in a practice state, and may perform better.

In any environment, the user may request a "calm break" and the wearable computing device may present a calm and focused environment to the user. The device may adjust the visual and aural environment to help somebody improve performance. It can help us to regulate ourselves based on mood with continuous feedback.

Application: Pattern Recognition, Data Harvesting, Across Population: (G)

In an application, a data mining or surveillance contractor may uses the wearable computing device of the present invention, optionally with one or more connected devices, such as Google Glass, to passively gain information on mood changes and brainwave trends in large populations like cities or neighborhoods. The wearable computing device may passively collect Brain State data using multiple Sensors to generate contextual baselines for both individual users and general populations. Possible Sensors include: cameras, eye-tracking EOG, galvanic skin response, bone vibrations, muscle twitch sensors, accelerometers, pheromone and hormone detectors, gyrometers, and basic brainwave sensors. All Brain State data can be stored in a variety of ways: clouded, on secure servers, within onboard storage, or in communication networks or social network platforms. A surveillance contractor writes an algorithm to sift through publicly available Brain State data to determine changes in a population's Brain State. This data can be used to find trouble spots in traffic flow via locative data, to determine whether a population is experiencing continual ERNs or P300s or whether they are sad or happy, how a population is sleeping, their level of focus using example using Beta: Theta ratio detection, or whether they pay attention to ads or marketing campaigns using eye-tracking detection. The process rules involved in this scenario determine whether data is freely available or freely shared or not. This is baked into the individual user profile, in much the same way that Facebook or Google logs and shares user data based on iterative opt-in/opt-out choices from the user.

In this application, users may be able to determine Brain States of large populations in general and notice trends in Brain States. This may be of benefit to surveillance contractors, data harvesters, national marketing advertising agencies, social media strategists, and/or political campaign managers.

Application: Pattern Recognition, Data Harvesting, Across Population: Example: Don Wants to Know if his Billboard Ad for Baked Beans is Working (G.1)

For example, "Don" contracts with a passive Brain State surveillance firm to use the wearable computing device to track eye-movements and Brain State changes among cities where his national marketing campaign is being run. Over time, Don begins to see which populations are paying attention to his campaign, based on trends analysis from the contractor.

The wearable computing device may have a digital compass to tell compass direction and an accelerometer to know its orientation angle relative to the force of gravity. With compass direction, direction of gravity, and GPS coordinates an algorithm can determine the direction that a user wearing the device is looking. An advertising agency wants to know if a billboard campaign is effective. The device can count the number of eyeball impressions its billboard ad is receiving. In addition, the emotional impact of a billboard ad can be estimated by analyzing the brainwaves of a user at the time they are known to be facing the billboard.

A user's positive reaction to a billboard ad can prompt a message from the ad agency to provide incentives to the user to purchase or further engage with additional product information. Through analysis of the user's brainwaves, the content of an ad being displayed may be altered, blocked out or changed to a different ad altogether.

If one sees an ad then it can be embellished customized to the preferences of the user. For example, a car company displays an ad in Glass and the device knows that the does not like overt ads by previous reactions of the user's brainwaves to overt ads. Instead of the overt car ad the user sees a nature scene such that the car is added to the person's experience. Or the user may be presented with a beautiful nature scene with a symbol representing the car company. This allows brand placements tuned to user and more pleasant to user but something that builds the brand. In this way all ads may be customized. Since the wearable computing device may know the user's preferences. If the user reacts badly or well that can be fed back to the advertiser. Advertisers can customize the experience to particular people. Avoiding annoying customers can work to an advertiser's advantage. For example, an advertisement may be skipped after a predetermined amount of time, such as 5 seconds, to allow the advertiser the opportunity to advertise without annoying the user.

Ads may be driven privately to each user. For example, if somebody enters a store, the store may drive ads to the individual's wearable computing device. If the customer is known then customer appreciation deals may be offered.

A billboard could be blank space and could be customized to individual. If an ad wins the placement but the user does not like it, the advertiser may receive feedback from the user's wearable computing device. The ad could be modified based on the feedback. For example, if a large ERN is generated then the ad could fade out. If user is paying attention then ad is kept. If the user looks away then ad could disappear. Ads could be synchronized to a user's physiology (e.g. if one is sleepy then ad is at a slower pace. For example, the ad may be linked to breathing such as for an allergy medication—as the user breathes then the view of the field moves.

For example, the wearable computing device may measure the user's heartbeat or mental state and communicate with a dating service to update a profile picture based on the measurements.

The wearable computing device may allow altering the content the user is viewing in ways to help alleviate stress and or anger of the user. For instance, if the user sees an ad for a product they do not like the plot of the ad could be changed into a humorous version so the user gets retribution and have humor at the same time.

Application: Pattern Recognition, Data Harvesting, Across Population: Example: Josh Wants to Know how Voters within Swing States Feel about Candidate for President (G.2)

For example, "Josh" is managing a campaign for public office. Josh contracts with a passive Brain State surveillance contractor. He develops a process rule that uses the wearable computing device and, optionally, connected devices such as Google Glass, to take note of when the general population above the voting age in those states is exposed to ads featuring Josh's candidate, and to immediately detect Brain State in that moment. This acts as a "snapshot poll" for the candidate. The contractor reports on the results of these Brain State polls for Josh.

Application: Skill Development: Improving Videogame Performance (H.1)

In an application, the wearable computing device may respond with positive reinforcement when a task is performed correctly by reading the user's emotional state to reinforce learning behaviour.

In an example, "Jermaine", is a big fan of particular videogame, which he plays at least every day against other competitors over the internet using a proprietary gaming network. Jermaine plays the videogame while wearing the wearable computing device, which may provide him with additional in-game value, like a heads-up display, and chat capabilities. Chatting may be accomplished via the internet or the proprietary gaming network. When Jermaine has difficulty in a particular part of the videogame, brainwave sensors of the wearable computing device detect an ERN or similar, detecting Jermaine's anger or frustration at losing. A mini in-game training exercise may be launched designed to help him progress past the impasse. The data for the minigame may be stored on the gaming console itself or on the Internet, which is then downloaded to the user. The wearable computing device may track his progress and offer him incentives and rewards by brainwave-reading applications on the wearable computing device monitoring his mental state for positive and negative emotional signals. The wearable computing device may, or may direct another device, to offer encouragement to the user when negative-state brainwaves are detected, like an ERN (or similar). When Jermaine exits the mini-game and proceeds past the impasse in the videogame, the wearable computing device may optionally communicate with the videogame either directly through WiFi or over an Internet connection to reward him with in-game options (e.g. new weapon choices, etc.).

Human performance in a number of tasks is closely tied to a user's emotional state. If someone is angry or frustrated, they are less likely to achieve good results in a task. In a non-limiting aspect of the present invention, by monitoring these mental states and tying the monitoring process into the wearable computing device of the present invention, the system can be made to reinforce positive modes of behaviour to improve performance at a task or to steer the user towards a desirable emotional state. This system may also help the user improve his or her state of mindfulness by encouraging the user to be conscious of their emotional state.

Application: Skill Development: Learning a Sport (H.2)

Figure 50:
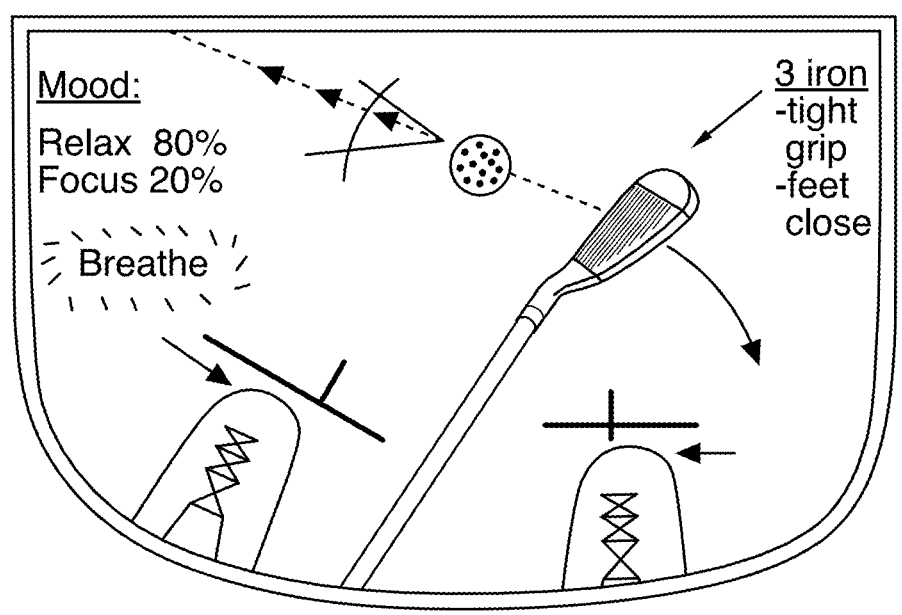
FIG. 50 illustrates a view in a display of the wearable computing device in accordance with an exemplary embodiment of the present invention.

In an example of wearable computing device-assisted skill development, consider a person being taught how to play golf while wearing the device, as shown in the view of the display of the device of the present invention as shown in FIG. 50. The user stands over the ball with a club in hand. The wearable computing device analyzes the position of the golfers feet, relative to the position of the golf ball. The wearable computing device uses the type of golf club (e.g. 3-iron) to determine the golfer's optimal position. Augmented Reality is overlaid on what the user is actually seeing to show an image of where the user should place their feet to the correct position based on the type of club being used. The user aligns the ball in the screen with the actual ball on the ground. Then an image of AR feet are shown set to guide the user to correct placement. This same approach may be used for hand grip as well.

The user's emotional state may be determined prior to an attempt to hit the golf ball. The wearable computing device may analyze the user's brainwaves to determine the user's current emotional state. The wearable computing device may suggest a brief focused breathing exercise for the user to do to get the user into the right frame of relaxed but focused attention necessary for golf.

The wearable computing device may also attempt to analyze the user's swing and expected ball trajectory. Accelerometer data in the device plus an analysis of the trajectory and speed of head motion can also be used to provide feedback to the user on the mechanics of their golf swing.

Application: System Adaptation to User Response: Changing Grocery Store Preferences (I.1)

In an application of the present invention, the wearable computing device may self-adjust its notification systems to reflect the changing preferences of the user For example, "Kwame" is at the grocery store on Tuesday night to do his weekly shop, as is his usual custom. Data collected from the wearable computing device during his previous shopping excursions shows that Kwame has purchased chocolate ice cream three out of the last four times he visited the grocery store. This information is stored on a remote server, or in the cloud, and is retrieved by the device over the internet. As he approaches the store, the device, or another service in communication with the device (e.g. Google Now), may predict that he will buy chocolate ice cream again. The device may remind Kwame to add chocolate ice cream to his grocery list, which he is viewing through the device's display. The software overlays a map to the frozen foods section and displays information about brands of chocolate ice cream that are on sale. Kwame may have an ERN (or similar) because he has promised his wife that he will eat healthier desserts. In irritation, Kwame tells the device that he doesn't want to buy ice cream this time around; he asks for a healthier alternative. The device may present an representation of an apology and adjust its algorithm to match Kwame's new preference. The device may then suggest a healthier option—fruit salad—and asks Kwame if he agrees with the suggestion. Kwame agrees and the device displays a map (from Google Maps or similar) guiding him to the produce section of the store. The device may ask Kwame if he'd like to try the "Fruit Salad Spectacular" recipe from recipes.com. Content is delivered from this website (or from another third party) to the user's mobile device. Kwame agrees and the device shows him the recipe and tells him where to find the items necessary for making the dessert.

Tools like Google Now are very useful for predicting consumer behaviour, but people's tastes can change rapidly and the prediction software needs to be able to nimbly adapt to the new circumstances of the user. The wearable computing device can therefore be a valuable adjunct to Google's predictive capabilities, using sensor-derived feedback to tailor the Google's predictions more precisely to the user's habits when they diverge substantially from their previous behaviour.

Application: System Adaptation to User Response; Cultivating Mindfulness Based Dietary Choices (I.2)

Many human behaviors are motivated by underlying emotions that the user is not fully aware and that can unconsciously influence choices that the user makes. An example is emotional eating which occurs for reasons other than hunger. Instead of feeling hunger as a motivation to eat, an emotion triggers the eating.

In an application, a goal may be to make the user aware that they are about to eat based on an emotional trigger rather than hunger. Often the food choices for emotional eating are very specific to the user and can vary depending on the mood of the user, and what you reach for when eating to satisfy an emotion may depend on the emotion. People in happy moods tended to prefer foods such as pizza or steak while sad people may prefer ice cream and cookies, and bored people may prefer potato chips.

First, the wearable computing device may learn the user's patterns of emotional eating. Emotional eating patterns are usually associated with time, location, and an emotion or thought. The device may gather data about the situations and conditions that lead to emotional eating. The device may analyze the emotional state of the user on an almost continuous basis. The device may use its video camera to determine the type of food that the user has eaten. Alternatively the user could provide this information to the device, or another connected device, using a voice command that may be processed using voice recognition to determine the command spoken by the user. The output is a set of rules or conditions that lead to emotional eating. A rule could be "When user is bored and they are at home in the evening then the user eats potato chips."

Next, the device may monitor the brainwaves of the user to alert the user to the onset of emotional eating. After the device learns a set of rules then it can monitor the emotions of the user, their location, time of day to determine the probability that the user will engage in emotional eating.

Next, the device may attempt to help the user become more self-aware and suggests strategies. If the probability of emotional eating is high then the device may make the user aware of its prediction. Increased self-awareness is key to helping the user discover these patterns on their own. The device can also suggest alternatives to combat emotional eating such as taking part in an stress reduction exercise or doing a different activity.

Over time, the device may build a profile of information for the user, and adapt the Algorithmic Pipeline to fit the user's habits. Based on how the user responds to calendar prompts via the device, the device may establish contextual baseline Brain States based on calendar events. The device may display calendar alerts and suggestions to the display.

This application may be of benefit to end users, calendar developers, and developers.

Application: System Adaptation to User Response: Training Google Now User's Preferences (1.3)

In an application, the wearable computing device may train an application such as Google Now based on brainwave measurements. For example, assume the user has a squash game on the same day two weeks in a row and Google Now adds another game to the user's calendar. When the user registered an ERN looking at the new calendar entry, the wearable computing device may remove the item from the calendar.

Google Now allows one to access information that is personalized to a user like Weather, Sports, Traffic. Google Now can also provide personalized services such as notifying you of your next appointment in a timely way allowing you enough time to get to your next appointment. It does this by knowing your next appointment, your current location, current traffic conditions and a route to your next appointment. In addition to your calendar, you can set reminders in Google Now that have conditions set to the reminder. For instance, one can say "Remind me to pick up milk next time I am at the grocery store". Google Now can pop up suggestions based on one's preferences. For instance, it can say there is an Irish Pub down the block and around the corner. To make these suggestions Google Now needs to learn your preferences. In the present invention, data produced by or available to the wearable computing device may be mined to learn user preferences. It can take into account, web page history, emails, text messages, past Google Now commands, etc. and learn one's preferences by data mining the text across these interactions. The new functionality that the wearable computing device adds is the ability to add brain state to the information to help Google Now have a more accurate and better set of knowledge about one's preferences and habits so that it can be a more effective assistant. In addition, brain state can detect errors and it is through error detection that the rules that Google Now uses to do its tasks can be updated.

For example, the user enters that they have a squash game with a friend on the same day and time two weeks in a row. Google Now assumes that this is a pattern and automatically creates the suggestion and asks the user if they would like to have Google Now enter this as a recurring appointment. The wearable computing device detects that this suggestion is met with irritation by the user as they say no to Google Now's suggestion. In addition to the user's rejection of the suggestion, the wearable computing device knows that this suggestion is met with irritation. Over time the device learns that any suggestions it makes to automatically populate the user's calendar is met with irritation and stops this practice. By adding brain state this allows Google Now to make better predictions about the user's preferences. The wearable computing device may ask, "I note irritation. Do you want me to stop automatically filling in your calendar?" By detecting brain state response and asking the user to confirm an action based on the detection, the present invention may allow for a more natural learning process that relies on less information for data mining. In addition to actions the wearable computing device may also learn to optimize its interface to the user.

In addition to monitoring salience of the real-world, the salience of information on the device's display to the user may also provide useful information. The display of the wearable computing device may provide a stimulus that generates a salient brain-state to the user. The system can know when the user is engaged with on-glass information by SSVEP, eye-tracking, blink rate or by other methods. Methods for determining a user's visual interest in what is being displayed on the device may use a combination of inputs including: Visual Evoked Potentials, eye movements (dynamic tracking of eyes—camera or EOG), GSR, cognitive load, patterns of muscle tension (EMG) indicative of movement of head, neck, and eye in addition to accelerometer, brainwaves.

Analysis of brainwaves such as Error Related Negativity (ERN) can be used to help control the display. These rules can be modified by classifying the reaction or perception of the user to Process Rules that the wearable computing device executes. A reaction or perception by the user to an action taken by the display can be classified by the device. The classification may be for instance a positive or negative reaction. A positive reaction can reinforce the weight of the data used by machine learning to build a model from which Process rules are derived. In addition to brainwaves, the device may use facial expression, muscle tension, eye movement to build a model of when the user approves or disapproves of actions the device takes.

Take the example of when wearable computing device turns itself on or off. The device may have Process Rules that govern when it turns itself on or turns itself off. When the display comes on then a recognizable tone, as an example, can be sounded to call attention to the user. This tone provides a strong correlation with display and provide a precise time for the stimulus. Precise time for stimulus allows the device to improve the signal to noise ratio of event related potentials (ERP) in the user's brainwaves. This improves the accuracy of classification. The ERP may be classified for instance as approval from the user or disapproval. Also incoming text messages could have a tone to alert the user that an incoming message has arrived. If device classifies the user's ERP as negative the device may turn its display off. This instance of disapproval of a Process Rule by the device can be used by the device to change this Process Rule. Process Rules are dependent upon the context in which the device is being used. This instance can be added to the set of instances associated with this context to change the model the Process Rules are built upon to help improve the accuracy of the devices' Process Rules.

The wearable computing device can operate in different modes depending on the needs and context of the user. A mode of operation is a set of Process Rules that are used in a specific context. Examples of modes can include: on duty, relaxing, in conversation with a worker. Different Process Rules may apply to different device operations. Examples of context are: the current task or activity that the user is currently doing, the user's current location, time of day or day of week, presence of other people. In addition context can include the state of the user's body and brainwaves that includes arousal, emotional state, body temperature, body fatigue, Galvanic Skin Response, heart rate, what the user is seeing, hearing or odors present in the environment.

The device may turn its display on or off based on various determined situations. For example, the device detects that the user wants the display to be active or inactive. A gesture is used by the user to turn the display on. Examples of gestures can be winks, rapid sequence of blinks, tip or flip of the head etc.

The device may use rules to infer when to turn the display on or off. The device needs to learn the set of rules used to turn the display on or off. It can use the instances of when the user gestured to activate/deactivate the display plus the context at the time of gesture to build a set of data that machine learning can use to build a set of Process Rules associated with activation/deactivation of display. Once a set of Process Rules has been built then the device can display which Process rules it used associated with an action. This tells the user why the device took the actions. The device can get the user's reaction from his/her brainwaves to help train the device and modify the Process Rules. The display is information words, pictures, and presents at same time. Both visual and auditory feedback helps user understand what device is thinking and the user can give the device constructive feedback to improve its responsiveness and accuracy. The devices actions are made transparent to the user.

The device can get help on deciding user settings, such as preferences input from the user or including manual override, or override based on ERPs detected by the device that are associated with a user's preference. For example, the display may turn on and the device detects that the user does not like this based on ERP. Then the device can say "device turning off because I see you didn't like device turning on at this time". Alternatively, or in addition to, a tone may sound which is associated with an error detection. In this way a familiar tone may sound whenever the device performs an action and in response detects an ERP from the user, and undoes or cancels the action in response. The user can then reverse the decision taken by this Process Rule and reactivate the display by predefined gestures. For instance if the user wants to come back then the user could be offered choices including: (i) ignore my disapproval in this case as it was not important in this case; and (ii) this is an important case, please modify Process rules to comply with this context. The user can also provide a feedback mechanism which can include a learning strength such as this is an important example, not important, mediocre, example, assigning weights to each data point on a 5 point scale where, for example 1=poor job, 3=neutral, 5=great job, etc. when giving system feedback on its performance. This can also be associated with the strength of the ERN. Also the device may notice increased engagement of the user as a sign of the device correctly applying a Process rule. The device may therefore have the ability to differentiate something the device should learn from and things it should not learn from. Similar logic can be used to turn device off. The device could be biased to correct itself to turn itself on quicker than turning itself off.

Another situation of the display turning itself on or off can occur when an event happens such as message comes in. A similar method can be used by the device to learn the user's preference. For example an email comes in and the display turns on. The device detects that the user is annoyed and hence the display can be turned off. The device takes into account the context such as the user is nervous as they are having a conversation with a person the device has identified as the user's boss. Pop ups can create annoyance and hence disappear more quickly because device detects brain state of annoyance.

Another situation is where the device always turns on because of the context of the user. An example is when a factory worker is on-duty it always turns on.

The device can use measures of cognitive workload and situation awareness to adjust the amount of information presented on the display. One can use cognitive workload to adjust the complexity from novice to expert. Augmented reality may help focus one in on what is important. This may also be used during an emergency. For example, in a cockpit the pilot may be guided to focus on what instruments they should be focusing on such as direction of horizon indicating the airplane is upside from what they expect. Elements of the display not relevant to the current situation may be greyed out. Accordingly, the device may guide to help pilot focus on what is important—grey out what is not important.

Application: System Adaptation to User Response: Personalized Content Delivery Based on P300 (I.4)

In another application, the wearable computing device may personalize use the Algorithmic Pipeline to determine that the user experiences P300 responses for example, when looking at sports news, but not celebrity gossip. As a consequence, the device sends the user more sports news in general.

The wearable computing device may automatically discount visual search results that cause ERN or other negative responses within the wearer.

The wearer may use the wearable computing device of the present invention to establish a contextual baseline Brain State. Certain elements of the visual field cause ERNs and other negative Brain State responses within the wearer. Using an onboard application, the wearer develops her own Process Rule to personally tailor her visual field to avoid "triggers" for negative Brain State responses. The output of these responses is a blurred or mosaic pattern in place of clear vision, rendered using the Computational Ability of the device.

This may be of value for the ability to personally tailor the visual field based on Brain State. Individual users who have reason to exclude various elements from their visual field may benefit.

Application: System Adaptation to User Response: Block People from View that One does not Like (I.5)

In another application, the wearable computing device may detect when the wearer of the device does not like another person. When this occurs, Process Rules exclude from his vision everyone that the device has detected that this user does not like. When he sees people whose looks he doesn't like, he dismisses them from his vision. Over time, the device learns who to exclude from his vision. Optionally, he still "sees" these people via, but only as mosaics, blurs, or otherwise obfuscated forms.

Application: System Adaptation to User Response: Excluding Objects from Visual Field (I.6)

In another application, the wearable computing device may exclude particular detected objects from the wearer's visual field on the display of the device. For example, assume "Russ" is in recovery for alcohol abuse. To aid his recovery, Russ uses the device to write a Process Rule that cuts labels for alcoholic products and advertisements out of his visual field. He no longer sees them while wearing the devices. For example, whenever he passes an ad for alcohol or sees it on television or at a party, he experiences an ERN related to the mistakes alcohol has helped him make. Over time, the device learns from his Brain State and tailor his locative data and Maps to give him driving directions that take him away from liquor stores, bars, and certain neighborhoods.

Glossary of Terms: Brainwave Signals and their Characteristics

Brainwave characteristics are divided into two categories. One type is Event Related Potentials (ERP) that are usually associated with an external stimuli. The Glossary: Alpha Power An increase in alpha power in the occipital and parietal regions is associated with increased relaxation.

Glossary: Audio Evoked Potential

Auditory information is processed in several different areas of the cochlea, the brainstem, probably the midbrain, thalamus and cortex.

The potentials arising from higher order processing are also the ones with the greatest latency, and they are described separately (P300, N400).

Research has shown that it is possible to record brainstem potentials in response to high density clicks from electrodes close to the ear, referenced to a central location (e.g. Cz). The sampling rate should be at least 2000 Hz. Under these conditions, several peaks of -1 microvolt can be detected approx. 1 ms apart. (The first peak is generated by the auditory nerve, the third to fifth are generated in the brain stem). These components are affected by the subject's auditory sensitivity and state of arousal. Another factor to control for is whether a tone is presented to one or both ears as there are neurons for monaural processing (separate neurons for the left and right ear) and neurons for binaural processing.

The middle latency potentials (MLP) are once again a series of peaks occurring about 10-50 ms after stimulus onset. The most consistent component has been labeled 'Pa' and is assumed to be generated by the auditory cortex (located in the temporal lobes) and ascending subcortical activations as the signal still occurs when with bilateral lesions to the primary auditory cortex.

Long latency potentials with respect to auditory stimuli are the earliest auditory ERPs, beginning at a latency of 50 ms (P50).

The P50 is assumed to be generated in the primary auditory cortex but depends heavily on sensory, cognitive and motor processing, i.e. the current state of an individual or disorders affecting these modalities. The P50's generators are very similar to those of the N100, which shows whenever there is an acoustic change in the environment, i.e. it can be generated both in response to a stimulus onset as well as offset.

Glossary: Beta Power

An increase in beta waves (e.g. "focus", or "active mind", or work, or thinking, or cogitation) is used when attempting to control something.

Glossary: Beta-Theta Ratio

This measure is reinforced as part of Neurofeedback in ADHD therapy. In addition, it has been found that it can be used for diagnosing this disorder—in fact, the FDA has approved this technology to help diagnosing it. The feedback is typically based on measurements from central locations. See ref: Monastra V J, Lubar J F, Linden M, et al: Assessing attention-deficit hyperactivity disorder via quantitative electroencephalography: an initial validation study. Neuropsychology 1999; 13:424-433

Glossary: Contingent Negative Variation (CNV)

CNV occurs in situations where there is a warning stimulus announcing a second imperative stimulus with some delay. The location depends on the type of required reaction (e.g. perceptual or motor), and whether mental effort or timing play an important role. See ref: Luck S J, Kappenman E S, editors. The Oxford Handbook of Event-Related Potential Components. New York: Oxford University Press; 2012. pp. 441-473.

Glossary: Dynamical Neural Signature (DNS)

Synchronous patterns correlate with ongoing conscious states during a simple visual task. This can be used to detect anesthetic state, or drowsiness.

Glossary: Electrooculography (EOG) Based Eye Tracking

EOG may records direction of the gaze using electricity detected from sensors on the skin near the eyes. This is not as accurate as with video based eye tracking.

Glossary: Error Related Negativity (ERN)

This negative potential begins when an error is made or when observing someone else making an error, and it peaks approximately 100 ms later. It originates in frontocentral areas of the brain. Some studies have observed this potential even when the subject is not aware of his/her mistake, but it is not yet clear whether this is a reliable effect. See ref: Luck S J, Kappenman E S, editors. The Oxford Handbook of Event-Related Potential Components. New York: Oxford University Press; 2012. pp. 441-473. See ref: Wessel, J. R. (2012). Error awareness and the error-related negativity: evaluating the first decade of evidence. Frontiers in human neuroscience, 6.

Glossary: Facial Expression Tracking

Facial expression tracking detects electromyographic activity (EMG) (i.e. muscle activity). This can tell whether a user is frowning/raising eyebrows/clenching teeth/smiling/looking left right etc.

Glossary: Frontal-Midline Theta

Frontal-midline theta is defined as a distinct frontal-midline theta rhythm at 6-7 Hz and 30-60 uV lasting seconds during mental tasks such as continuous arithmetic addition.

Glossary: Novelty P3 (ERP)

The novelty P3 has a similar polarity and latency as the P300, and it occurs in response to novel sounds, e.g. to an animal sound within an experimental setting where beeps are expected. If this novel sound occurs repeatedly, the response in terms of EEG will turn into a P300. It is localized more frontally than the P300. See ref: Luck S J, Kappenman E S, editors. The Oxford Handbook of Event-Related Potential Components. New York: Oxford University Press; 2012. pp. 441-473.

Glossary: N400 (ERP)

The N400 is related to semantic processing (i.e. understanding language). It is a negative potential occurring approximately 400 ms after reading an unexpected word, e.g. "I like coffee with milk and dog". The latency is usually 400 ms but resulting negative potential can have a duration of several hundred milliseconds. See ref: Luck S J, Kappenman E S, editors. The Oxford Handbook of Event-Related Potential Components. New York: Oxford University Press; 2012. pp. 441-473.

Glossary: P300 (ERP)

P300 occurs as a positive peak in the EEG signal between 200 ms to 700 ms after a person has sensed an external or internal stimulus such as a sound, image, word, person etc. Its amplitude correlates negatively with how frequent the stimulus is experienced, i.e. the amplitude of the potential is especially large for rare stimuli. This potential originates in centroparietal regions of the brain. See ref: Luck S J, Kappenman E S, editors. The Oxford Handbook of Event-Related Potential Components. New York: Oxford University Press; 2012. pp. 441-473.

A special case of the P300 is the Auditory ERP. It occurs for salient auditory stimulus.

Glossary: P300 Asymmetry

P300 asymmetry is a predictor of depression and occurs as an asymmetry in P300 potential of left versus right central regions. See ref: Bruder G E, Tenke C E, Towey J P, Leite P, Fong R, Stewart J E, McGrath P J, Quitkin F M. Brain ERPs of depressed patients to complex tones in an oddball task: relation of reduced P3 asymmetry to physical anhedonia. Psychophysiology. 1998 January; 35(1):54-63.

Glossary: Sleep Monitoring

Sleep monitoring refers monitoring duration and occurrence of different stages of sleep by recording the dominant power bands. Considers delta, theta, alpha and beta EEG bands. Deeper sleep is correlated with higher delta power. Increase in power bands progress in the following order as one goes from light to deeper sleep: theta to delta. Alpha power increase when one is drowsy but still awake. Rapid eye movement (REM) occurs when one is dreaming and can have similar brainwaves as when one is awake (e.g. more eye movement, higher alpha and beta waves than when in deep sleep).

Glossary: Sensorimotor Rhythm (SMR)

SMR is activity in the higher alpha frequency range that is expressed in the sensorimotor cortex. It occurs when the respective sensory-motor areas are idle. i.e. when no motor activity is planned or being executed, or when no sensory information is being processed. Some people have found it beneficial to increase SMR through neurofeedback in patients with learning disabilities, AD(H)D, and epilepsy.

Glossary: Steady State Visual Evoked Potential (SSVEP)

When looking at a light stimulus that is flashing at a certain constant frequency, this same frequency is reflected in EEG data. SSVEPs can best be detected at the back of the head, where the visual cortex is located. It may also be detected behind the ears or on the neck, but the optimal locations in these areas differ between people. SSVEPs are sometimes used in BCIs where two available options flash at different frequencies. By analyzing EEG data it is possible which option the user is focusing on. See ref: Wang, Y. T., Wang, Y., Cheng, C. K., & Jung, T. P. (2012, August). Measuring Steady-State Visual Evoked Potentials from non-hair-bearing areas. InEngineering in Medicine and Biology Society (EMBC), 2012 Annual International Conference of the IEEE (pp. 1806-1809). IEEE.

Glossary: Mismatch Negativity (MMN)

Mismatch negativity is a brain response to change irrespective of tasks or instructions., i.e. it occurs even when the subject is not paying attention. It usually refers to the auditory modality including speech, but can also be elicited through other sensory input. It is strongest at central and frontal locations. See ref: Luck S J, Kappenman E S, editors. The Oxford Handbook of Event-Related Potential Components. New York: Oxford University Press; 2012. pp. 441-473.

Glossary: Auditory Nerve and Brainstem Potentials (ABR)

ABR occurs within 10 ms after stimulus onset.

Glossary: Readiness Potential (RP)

The RP is a slowly increasing negative potential prior to a voluntary movement. It can begin as early as 2 seconds before the movement is executed and it is larger in the contralateral hemisphere, i.e. when planning to move the right finger, the RP is larger in the left hemisphere. The cortical areas it originates from include the motor & somatosensory cortex as well as the supplementary motor area. See ref: Luck S J, Kappenman E S, editors. The Oxford Handbook of Event-Related Potential Components. New York: Oxford University Press; 2012. pp. 441-473.

Glossary: N170

Evidence for this effect is not very strong but previous research suggests that processing faces involves some face-selective clusters in addition to cortical areas processing visual object shapes in general. Their activation results in a negative potential around 170 ms after presentation of the face. See ref: Luck S J, Kappenman E S, editors. The Oxford Handbook of Event-Related Potential Components. New York: Oxford University Press; 2012. pp. 441-473

Glossary: Somatosensory Evoked Potentials (SEP):

In research, only specific kinds of stimuli are applied to record SEPs because the resulting EEG signals can vary depending on the kind of stimulus: E.g., a stimulus to the lower extremities will result in SEPs with larger latencies than to the upper extremities. Also, different types of stimuli (e.g. pressure, heat, electrical impulses) are processed differently and different types of tissues can vary in the time they take for processing a stimulus and passing it on to the spinal cord. SEPs can be measured from the parietal cortex, close to the somatosensory cortex. This ERP seems to be very difficult to identify in EEG unless the stimulation is very well controlled. See ref: Luck S J, Kappenman E S, editors. The Oxford Handbook of Event-Related Potential Components. New York: Oxford University Press; 2012. pp. 441-473.

Glossary: Early Left Anterior Negativity (ELAN)

This is an EREP that occurs 200 ms or less after the stimulus. It occurs when a person hears a sequence of words that violates the rules of phrase structure. An example is Max's of proof (as opposed to Max's proof). In addition to language processing, it may also be associated with other kinds stimulus.

Glossary: Late Positive Component (LPC):

This is what some researchers call the P300. See ref: Luck S J, Kappenman E S, editors. The Oxford Handbook of Event-Related Potential Components. New York: Oxford University Press; 2012. pp. 441-473.

General

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

What is claimed is:

1. A method, performed by a wearable eyeglass frame comprising at least one bio-signal measuring sensor and a display, the at least one bio-signal measuring sensor including at least one electrophysiological sensor, the at least one electrophysiological sensor including at least one EOG sensor and at least one EEG sensor, comprising:
displaying at least one item on the display;
acquiring bio-signal data from a user using the at least one bio-signal measuring sensor, the bio-signal data comprising electrophysiological data from the at least one electrophysiological sensor;
processing the bio-signal data, in accordance with a profile associated with the user to compute at least one brainwave state measurement and at least one eye activity measurement, the at least one eye activity measurement computed using the electrophysiological data from the at least one EOG sensor, the at least one eye activity measurement based on changes in an electrical potential of the bio-signal data from the at least one EOG sensor, wherein the processing comprises detecting, within the at least one brainwave state measurement, an event related potential associated with the display of the at least one item;
determining, using the at least one eye activity measurement, positions and times of eye movements between points of focus on elements in a scene, the scene including the display, and positions and times of eye gaze fixations on points of focus on elements in the scene;
identifying a pattern of saccadic eye movement based on the eye movements and the eye gaze fixations;
upon identification of the pattern, associating the pattern with a condition of saliences of elements of the scene to the user;
determining a correspondence between the at least one brainwave state measurement, the eye movements, the eye gaze fixations, the saliences of elements of the scene to the user, and at least one predefined device control action; and
in accordance with the determined correspondence, controlling operation of at least one component of the eyeglass frame by modifying or initiating the modification of an image displayed on the display.

2. The method of claim 1 further comprising establishing the profile by calibration using a pre-determined set of exercises and acquiring baseline bio-signal data from the user using the at least one bio-signal measuring sensor.

3. The method of claim 1 further comprising establishing the profile using historical bio-signal data from the user.

4. The method of claim 1 wherein the eye activity measurement is based on at least one of EOG, EEG, event related potentials, and steady state visual evoked potential.

5. The method of claim 1 further comprising:
displaying an application interface on the display with at least one indicator;
detecting a selection of the at least one indicator using the at least one brainwave state measurement, the eye movements and the eye gaze fixations;
upon detecting the selection, activating a memory method for the application interface, the memory method comprising a set of electronic interactions to attempt to stimulate the user and aid the user in locating visual information based on items that the user has seen before on the display.

6. The method of claim 1 further comprising:
displaying an application interface on the display with at least one indicator;
detecting a virtual selection of the at least one indicator using the at least one brainwave state measurement, the eye movements and the eye gaze fixations;
upon detecting the selection, activating an inspiration method for the application interface, the inspiration method comprising a set of electronic interactions to attempt to stimulate the user and aid the user in locating visual information based on items that the user has not seen before on the display.

7. The method of claim 1 further comprising:
generating the profile associated with the user by configuring settings and pipeline parameters tuned to optimize the user's experience.

8. The method of claim 1 further comprising:
generating an instance of a pipeline with pipeline parameters;
processing the bio-signal data using the instance of the pipeline with the pipeline parameters;
updating the profile associated with the user with the pipeline parameters.

9. The method of claim 1 further comprising:
determining a level of user interest based on the at least one brainwave state measurement, the eye movements and the eye fixations.

10. The method of claim 1 wherein each of the at least one item flashes, independently, at a respective predetermined frequency, wherein the processing comprises detecting, within the at least one brainwave state measurement, for a steady state visually evoked potential having a frequency associated with any of the respective predetermined frequencies.

11. The method of claim 1 further comprising displaying an application interface on the display with at least one indicator, wherein the determining of the correspondence between the at least one brainwave state measurement, the eye movements, the eye gaze fixations, the saliences of elements of the scene to the user, and at least one predefined device control action includes:
detecting a selection of the at least one indicator using the at least one brainwave state measurement and a fixation in the eye gaze fixations.

12. The method of claim 1, wherein the eyeglass frame further comprises at least one orientation sensor selected from an accelerometer, a gyroscopic sensor, and a compass;
wherein the method further comprises determining a head orientation using the at least one orientation sensor; and
wherein the determining a correspondence between the at least one brainwave state measurement, the eye movements, the eye gaze fixations, the saliences of elements of the scene to the user and the at least one predefined device control action further comprises determining a correspondence between the at least one brainwave state measurement, the eye movements, the eye gaze fixations, the saliences of elements of the scene to the user, the head orientation, and the at least one predefined device control action.

13. A non-transitory computer program product tangibly embodying code that, when executed by a processor, causes the processor to:
    display at least one object on a display of a wearable eyeglass frame;
    acquire bio-signal data from a user using at least one bio-signal measuring sensor, the at least one bio-signal measuring sensor including at least one electrophysiological sensor, the at least one electrophysiological sensor including at least one EOG sensor and at least one EEG sensor, the bio-signal data comprising electrophysiological data from the at least one electrophysiological sensor;
    process the bio-signal data in accordance with a profile associated with the user to compute at least one brainwave state measurement and at least one eye activity measurement, the at least one eye activity measurement computed using the electrophysiological data from the at least one EOG sensor, the at least one eye activity measurement based on changes in an electrical potential of the bio-signal data from the at least one EOG sensor, wherein the processing comprises detecting, within the at least one brainwave state measurement, an event related potential associated with the display of the at least one object;
    determine, using the at least one eye activity measurement, positions and times of eye movements between points of focus on elements in a scene, the scene including the display, and positions and times of eye gaze fixations on points of focus on elements in the scene;
    identify a pattern of saccadic eye movement based on the eye movements and the eye gaze fixations;
    upon identification of the pattern, associate the pattern with a condition of saliences of elements of the scene to the user;
    determine a correspondence between the at least one brainwave state measurement, the eye movements, the eye gaze fixations, the saliences of elements of the scene to the user, and at least one predefined device control action; and
    in accordance with the determined correspondence, control operation of at least one component of the wearable eyeglass frame by modifying or initiating the modification of an image displayed on the display.

14. A wearable eyeglass frame comprising:
    at least one bio-signal measuring sensor, the at least one bio-signal measuring sensor including at least one electrophysiological sensor, the at least one electrophysiological sensor including at least one EOG sensor and at least one EEG sensor;
    a display;
    at least one data processor coupled to the at least one bio-signal measuring sensor; and
    a non-transitory computer-readable medium or media comprising computer-executable instructions configured to cause the at least one data processor to:
    display at least one item on the display;
    acquire bio-signal data from a user using the at least one bio-signal measuring sensor, the bio-signal data comprising electrophysiological data from the at least one electrophysiological sensor;
    process the bio-signal data in accordance with a profile associated with the user to compute at least one brainwave state measurement and at least one eye activity measurement, the at least one eye activity measurement computed using the electrophysiological data from the at least one EOG sensor, the at least one eye activity measurement based on changes in an electrical potential of the bio-signal data from the at least one EOG sensor, wherein the processing comprises detecting, within the at least one brainwave state measurement, an event related potential associated with the display of the at least one item;
    determine, using the at least one eye activity measurement, positions and times of eye movements between points of focus on elements in a scene, the scene including the display, and positions and times of eye gaze fixations on points of focus on elements in the scene;
    identify a pattern of saccadic eye movement based on the eye movements and the eye gaze fixations;
    upon identification of the pattern, associate the pattern with a condition of saliences of elements of the scene to the user;
    determine a correspondence between the at least one brainwave state measurement, the eye movements, the eye gaze fixations, the saliences of elements of the scene to the user, and at least one predefined device control action; and
    in accordance with the determined correspondence, control operation of at least one component of the eyeglass frame by modifying or initiating the modification of an image displayed on the display.

15. The eyeglass frame of claim 14 further comprising at least one eye-tracking sensor, the non-transitory computer-readable medium or media comprising the computer-executable instructions configured to cause the at least one data processor to:
    acquire at least one eye-tracking measurement from the user using the at least one eye-tracking sensor, the at least one eye-tracking measurement including at least one of an eye blink frequency and an eye blink duration;
    process the at least one bio-signal data, the eye-tracking measurement and the displayed location of one of the at least one displayed item; and
    in accordance with the determined at least one predefined device control action, control operation of the at least one display by modifying or initiating the modification of at least one displayed item.

* * * * *